US010640545B2

(12) United States Patent
Oudit et al.

(10) Patent No.: US 10,640,545 B2
(45) Date of Patent: May 5, 2020

(54) APELIN PEPTIDES AND USES THEREOF

(71) Applicant: THE GOVERNORS OF THE UNIVERSITY OF ALBERTA, Edmonton (CA)

(72) Inventors: Gavin Oudit, Edmonton (CA); John Vederas, Edmonton (CA); Shaun McKinnie, Edmonton (CA); Conrad Fischer, Edmonton (CA)

(73) Assignee: THE GOVERNORS OF THE UNIV OF ALBERTA TEC EDMONTON, Edmonton (CA)

( * ) Notice: Subject to any disclaimer, the term of this patent is extended or adjusted under 35 U.S.C. 154(b) by 0 days.

(21) Appl. No.: 16/027,237

(22) Filed: Jul. 3, 2018

(65) Prior Publication Data

US 2019/0010202 A1 Jan. 10, 2019

Related U.S. Application Data

(60) Provisional application No. 62/528,379, filed on Jul. 3, 2017.

(51) Int. Cl.

| | |
|---|---|
| ***A61K 38/00*** | (2006.01) |
| ***C07K 14/575*** | (2006.01) |
| ***A61K 38/22*** | (2006.01) |
| ***A61K 47/54*** | (2017.01) |
| ***A61P 9/10*** | (2006.01) |
| ***A61K 9/00*** | (2006.01) |
| ***A61P 9/00*** | (2006.01) |
| ***A61P 9/12*** | (2006.01) |
| ***A61K 47/60*** | (2017.01) |
| ***C07K 14/47*** | (2006.01) |

(52) U.S. Cl.

CPC .......... *C07K 14/575* (2013.01); *A61K 9/0019* (2013.01); *A61K 38/22* (2013.01); *A61K 47/542* (2017.08); *A61K 47/60* (2017.08); *A61P 9/00* (2018.01); *A61P 9/10* (2018.01); *A61P 9/12* (2018.01); *C07K 14/47* (2013.01)

(58) Field of Classification Search

None

See application file for complete search history.

(56) References Cited

FOREIGN PATENT DOCUMENTS

| | | | |
|---|---|---|---|
| CA | 2918077 | A1 | 1/2015 |
| WO | 2011047215 | A1 | 4/2011 |
| WO | 2014081702 | A2 | 5/2014 |

OTHER PUBLICATIONS

Murza et al. ChemMedChem 2012, 7, 318-325.*

Patent Cooperation Treaty, International Search Report for PCT/IB2018/000837, dated Dec. 7, 2018, pp. 1-4.

Almenoff, J., et al., Membrane-bound kidney neutral metalloendopeptidase: Interaction with synthetic substrates, natural peptides, and inhibitors. Biochemistry 1983, vol. 22(3), 590-599.

Attané, C., et al., Apelin treatment increases complete fatty acid oxidation, mitochondrial oxidative capacity, and biogenesis in muscle of insulin-resistant mice, Diabetes, Feb. 2012, vol. 61, 310-320.

Baker, T. J., et al., Preparation and use of N,N'-di-Boc-N"-triflylguanidine, Org. Synth., 2002, vol. 78, pp. 91.

Barnes, G. D., et al., Sustained cardiovascular actions of APJ agonism during renin-angiotensin system activation and in patients with heart failure, Circ.: Heart Failure, 2013, vol. 6, pp. 482-491.

Bateman, Jr., R. C., et al., Identification of the active-site arginine in rat neutral endopeptidase 24.11 (enkephalinase) as arginine 102 and analysis of a glutamine 102 mutant, J. Biol. Chem., 1989, vol. 264, pp. 6151-6157.

Belokon, et al., Improved procedures for the synthesis of (S)-2-[N-(N'-benzyl-prolyl)amino]benzophenone (BPB) and Ni(II) complexes of Schiff's bases derived from BPB and amino acids, Tetrahedron: Asymmetry 1998, vol. 9, pp. 4249-4252.

Betts, V., et al., Aggregation and catabolism of disease-associated intra-Aβ mutations: reduced proteolysis of AβA21G by neprilysin, Neurobiol. Dis., 2008, vol. 31, 442-50.

Boucher, J.; et al., Apelin, a newly identified adipokine up-regulated by insulin and obesity, Endocrinology, 2005, vol. 146, pp. 1764-1771.

Bourguet, C. B., et al., Solution-phase submonomer diversification of aza-dipeptide building blocks and their application in aza-peptide and aza-DKP synthesis, J. Pept. Sci., 2010, vol. 16, pp. 284-296.

Brame, A. L., et al., Design, characterization, and first-in-human study of the vascular actions of a novel biased apelin receptor agonist, Hypertension, 2015, vol. 65, pp. 834-840.

Ceraudo, E., et al., Biased signaling favoring Gi over β-arrestin promoted by an apelin fragment lacking the C-terminal phenylalanine, J. Biol. Chem., 2014, vol. 289, pp. 24599-24610.

Chen, H.; et al., Apelin alleviates diabetes-associated endoplasmic reticulum stress in the pancreas of Akita mice, Peptides, 2011, vol. 32, pp. 1634-1639.

Cheng, X., et al., Venous dilator effect of apelin, an endogenous peptide ligand for the orphan APJ receptor, in conscious rats, European Journal of Pharmacology, 2003, vol. 470, pp. 171-175.

Choe, H.; et al., The orphan seven-transmembrane 1255 receptor Apj supports the entry of primary T-cell-line-tropic and dualtropic human immunodeficiency virus type 1, J. Virol., 1998, vol. 72, pp. 6113-6118.

De Mota, N., et al., Apelin, a potent diuretic neuropeptide counteracting vasopressin actions through inhibition of vasopressin neuron activity and vasopressin release, Proc. Natl. Acad. Sci. U.S.A., 2004, vol. 101, pp. 10464-10469.

Dion, N., et al., Evidence that Asn542 of neprilysin (EC 3.4.24.11) is involved in binding of the P2' residue of substrates and inhibitors, Biochem. J., 1995, vol. 311, pp. 623-627.

(Continued)

*Primary Examiner* — Jeanette M Lieb

(74) *Attorney, Agent, or Firm* — Pillsbury Winthrop Shaw Pittman, LLP

(57) ABSTRACT

The disclosure relates to modified apelin polypeptides having increased stability against kallikrein, NEP and ACE2 degradation and/or potency relative to the native apelin-13 and apelin-17 polypeptides. Embodiments also disclose methods of using the polypeptides for treating cardiovascular disorders.

41 Claims, 22 Drawing Sheets

Specification includes a Sequence Listing.

(56) References Cited

OTHER PUBLICATIONS

El Messari, S., et al., Functional dissociation of apelin receptor signaling and endocytosis: implications for the effects of apelin on arterial blood pressure, J. Neurochem., 2004, vol. 90, pp. 1290-1301.
Fan, X., et al., Structural and functional study of the apelin-13 peptide, an endogenous ligand of the HIV-1 coreceptor, APJ. Biochemistry, 2003, vol. 42, pp. 10163-10168.
Gafford, J. T., et al., Human kidney "enkephalinase", a neutral metalloendopeptidase that cleaves active peptides, Biochemistry, 1983, vol. 22, pp. 3265-3271.
Garcia-Ramos, Y.; Lubell, W. D., Synthesis and alkylation of aza-glycinyl dipeptide 1354 building blocks, J. Pept. Sci., 2013, vol. pp. 19, pp. 725-729.
Gerbier, R., et al., Development of original metabolically-stable apelin-17 analogs with diuretic and cardiovascular effects, FASEB J, 2017, vol. 31, pp. 687-700.
Gerbier, R., et al., New structural insights into the apelin receptor: identification of key residues for apelin binding, FASEB J., 2015, vol. 29, pp. 314-322.
Gu, X., et al., Large scale enantiomeric synthesis, purification, and characterization of ω-unsaturated amino acids via a Gly-Ni(II)-BPB-complex. Tetrahedron, 2004, vol. 60, pp. 8233-8243.
Heinonen, M. V., et al., Apelin, orexin-A and leptin plasma levels in morbid obesity and effect of gastric banding, Regul. Pept., 2005, vol. 130, pp. 7-13.
Iturrioz, X., et al., By interacting with the C-terminal Phe of apelin, Phe255 and Trp259 in helix VI of the apelin receptor are critical for internalization, J. Biol. Chem., 2010, vol. 285, pp. 32627-32637.
Japp, A. G., et al., Acute cardiovascular effects of apelin in humans: potential role in patients with chronic heart failure, Circulation, 2010, vol. 121, pp. 1818-1827.
Japp, A. G., et al., Vascular effects of apelin in vivo in man, J. Am. Coll. Cardiol., 2008, vol. 52, pp. 908-913.
Kehoe, K., et al., Prolyl carboxypeptidase purified from human placenta: its characterization and identification as an apelin-cleaving enzyme, Biochim Biophys Acta, 2016, vol. 1864, pp. 1481-1488.
Kidoya, H., et al., Spatial and temporal role of the apelin/APJ system in the caliber size regulation of blood vessels during angiogenesis, EMBO J., 2008, vol. 27, pp. 522-534.
Langelaan, D.N., et al., Structural features of the apelin receptor N-terminal tail and first transmembrane segment implicated in ligand binding and receptor trafficking, Biochim. Biophys. Acta., 2013, vol. 1828, pp. 1471-1483.
Langelaan, D. N., et al., Structural insight into G-protein coupled receptor binding by apelin., Biochemistry, 2009, vol. 48, pp. 537-548.
Lee, D. K., et al., Characterization of apelin, the ligand for the APJ receptor, J. Neurochem., 2000, vol. 74, pp. 34-41.
Maguire, J. J., et al. [Pyr1]apelin-13 identified as the predominant apelin isoform in the human heart: vasoactive mechanisms and inotropic action in disease, Hypertension, 2009, vol. 54, pp. 598-604.
McKinnie, S. M., et al., The metalloprotease neprilysin degrades and inactivates apelin peptides, ChemBioChem, 2016, vol. 17, pp. 1495-1498.
McMurray, J. J.; Investigators, P.-H.; Committees, Angiotensin-neprilysin inhibition versus enalapril in heart failure, N. Engl. J. Med., 2014, vol. 371, pp. 993-1004.
Medhurst, A. D., et al., Pharmacological and immunohistochemical characterization of the APJ receptor and its endogenous ligand apelin, J. Neurochem., 2003, vol. 84, pp. 1162-1172.
Murza, A., et al., Elucidation of the structure-activity relationships of apelin: influence of unnatural amino acids on binding, signaling, and plasma stability, ChemMedChem, 2012, vol. 7, pp. 318-325.
Murza, A., et al., Stability and degradation patterns of chemically modified analogs of apelin-13 in plasma and cerebrospinal fluid, Peptide Science, 2014, vol. 102(4), pp. 297-303.
Nalivaeva, N. N., et al., Neprilysin, Handbook of Proteolytic Enzymes, 3rd Edn., Chapt. 127, 2013, Elsevier Ltd., pp. 612-619.
Narayanan, S., et al., Regulation of the apelinergic system and its potential in cardiovascular disease: Peptides and small molecules as tools for discovery, J. Med. Chem., 2015, vol. 58, pp. 7913-7927.
O'Dowd, B. F., et al., A human gene that shows identity with the gene encoding the angiotensin receptor is located on chromosome 11, Gene, 1993, vol. 136, pp. 355-360.
Pascal, R.; et al., Preservation of the Fmoc protective group under alkaline conditions by using CaCl2. Applications in peptide synthesis, Tetrahedron Lett., 1998, vol. 39, pp. 5031-5034.
Perjes, A., et al., Apelin increases cardiac contractility via protein kinase C epsilon- and extracellular signal-regulated kinase-dependent mechanisms, PLoS One, 2014, vol. 9(4), e93473, pp. 1-10.
Pitkin, S. L., et al., International Union of Basic and Clinical Pharmacology. LXXIV. Apelin receptor nomenclature, distribution, pharmacology, and function, Pharmacol. Rev., 2010, vol. 62, pp. 331-342.
Reaux-Le Goazigo, A., et al., Physiological role of a novel neuropeptide, apelin, and its receptor in the rat brain, J. Neurochem., 2001, vol. 77, pp. 1085-1096.
Rice, G. I., et al., Evaluation of angiotensin-converting enzyme (ACE), its homologue ACE2 and neprilysin in angiotensin peptide metabolism, Biochem. J., 2004, vol. 383, pp. 45-51.
Szokodi, I., et al., Apelin, the novel endogenous ligand of the orphan receptor APJ, regulates cardiac contractility, Circ. Res., 2002, vol. 91, pp. 434-440.
Tatemoto, K. et al., Isolation and characterization of a novel endogenous peptide ligand for the human APJ receptor, Biochem. Biophys. Res. Commun., 1998, vol. 251, pp. 471-476.
Traore, M., et al., Diversity-oriented synthesis of azapeptides with basic amino acid residues: aza-lysine, aza-ornithine, and aza-arginine, Org. Lett., 2014, vol. 16, pp. 3588-3591.
Vickers, C., et al., Hydrolysis of biological peptides by human angiotensin-converting enzyme-related carboxypeptidase, J. Biol. Chem., 2002, vol. 277, pp. 14838-14843.
Vijayaraghavan, J., et al., Hydrolysis of endothelins by neutral endopeptidase 24.11 (enkephalinase), J. Biol. Chem., 1990, vol. 265, pp. 14150-14155.
Wang, W., et al., Angiotensin converting enzyme 2 metabolizes and partially inactivates pyr-apelin-13 and apelin-17: Physiological effects in the cardiovascular system, Hypertension, 2016, vol. 68, pp. 365-377.
Wang W. et al., Loss of apelin exacerbates myocardial infarction adverse remodeling and ischemia-reperfusion injury: therapeutic potential of synthetic apelin analogues, J. Am. Heart Assoc., 2013, vol. 2, e000249, pp. 1-17.
Watanabe, Y., et al., Comparison of the hydrolysis of the three types of natriuretic peptides by human kidney neutral endopeptidase 24.11, Biochem. Mol. Med., 1997, vol. 61, pp. 47-51.
Yang, P., et al., Apelin, Elabela/Toddler, and biased agonists as novel therapeutic agents in the cardiovascular system, Trends Pharmacol. Sci., 2015, vol. 36, pp. 560-567.
Yue, P., et al., Apelin is necessary for the maintenance of insulin sensitivity, Am. J. Physiol.: Endocrinol. Metab., 2010, vol. 298, pp. E59-E67.
Zhang Y. et al. Identifying structural determinants of potency for analogs of apelin-13: integration of C-terminal truncation with structure-activity, Bioorg. Med. Chem., 2014, vol. 22, pp. 2992-2997.
Zhong, J.-C., et al. Targeting the apelin pathway as a novel therapeutic approach for cardiovascular diseases, Biochem. Biophys. Acta, 2019, vol. 1863, pp. 1942-1950.
Witteloostuijn, et al., Half-Life Extension of Biopharmaceuticals using Chemical Methods: Alternatives to PEGylation, ChemMedChem, 2016, vol. 11, pp. 2474-2495.
Schonauer, et al., Adrenomedullin 2.0: Adjusting Key Levers for Metabolic Stability, J. Med. Chem. 2016, vol. 59(12), pp. 5695-5705.
McKinnie, et al. , Synthetic Modification within the "RPRL" Region of Apelin Peptides: Impact on Cardiovascular Activity and

(56) References Cited

OTHER PUBLICATIONS

Stability to Neprilysin and Plasma Degradation, J. Med. Chem., 2017, vol. 60(14), pp. 6408-6427.
Gozzo, et al., Heparin modulation of human plasma kallikrein on different substrates and inhibitors, Biol. Chem., Aug. 2006, vol. 387(8), pp. 1129-1138.
Lima, et al., S(1)' and S(2)' Subsite Specificities of Human Plasma Kallikrein and Tissue Kallikrein 1 for the Hydrolysis of Peptides Derived from the Bradykinin Domain of Human Kininogen, Biol. Chem., Dec. 2008, vol. 389, pp. 1487-1494.
Kaur, J.A., A comprehensive review on metabolic syndrome, Cardiol. Res. Pract., Mar. 11, 2014, vol. 2014, pp. 1-21.
Malik, et al., Impact of the metabolic syndrome on mortality from coronary heart disease, cardiovascular disease, and all causes in United States adults, Circulation, 2004, vol. 110, pp. 1245-1250.
World Health Organization (WHO), Silent Killer, Global Public Health Crisis, WHO; Geneva, USA: 2013, A global brief on hypertension; pp. 1-40.
Guo, et al., Targeting apelinergic system in cardiometabolic disease, Curr. Drug Targets, 2017, vol. 18, pp. 1785-1791.
Bertrand, et al., Apelin and energy metabolism, Front. Physiol., 2015, vol. 6(115). pp. 1-5.
Dalzell, et al., The emerging potential of the apelin-APJ system in heart Failure, J. Card. Fail, 2015, vol. 21(6), pp. 489-498.
Folino, et al., Effects of apelin on the cardiovascular system, Heart Fail. Rev., 2015, vol. 20, pp. 505-518.
Ma, et al., Structural basis for apelin control of the human apelin receptor, Structure, 2017, vol. 25, pp. 858-866.
Tran, et al., A systematic exploration of macrocyclization in apelin-13: impact on binding, signaling, stability, and cardiovascular effects, J. Med. Chem., 2018, vol. 61, pp. 2266-2277.
Juhl, et al., Development of potent and metabolically stable APJ ligands with high therapeutic potential, ChemMedChem, 2016, vol. 11, pp. 2378-2384.
Pathak, et al., Structure of plasma and tissue kallikreins, Thromb. Haemost, 2013, vol. 110, pp. 423-433.
Abid, et al., Kinetic study of neuropeptide Y (NPY) proteolysis in blood and identification of NPY3-35: a new peptide generated by plasma kallikrein, J. Biol. Chem., 2009, vol. 284, pp. 24715-24724.
Kaplan, et al., Bradykinin formation. Plasma and tissue pathways and cellular interactions, Clin. Rev. Allergy Immunol., 1998, vol. 16, pp. 403-429.
Tang, et al., Expression, crystallization, and three-dimensional structure of the catalytic domain of human plasma kallikrein, J. Biol. Chem., 2005, vol. 280, pp. 41077-41089.
Pankow, et al., Structural Substrate conditions required for neutral endopeptidase-mediated natriuretic peptide degradation, J. Mol. Biol., 2009, vol. 393, pp. 496-503.

* cited by examiner pyr-1-apelin-13 (1) R = pGlu-
apelin-17 (2) R = KFRRQ-
apelin-36 (3) R = LVQPRGSRNGPG
PWQGGRRKFRRQ- R = pGlu- pyr-1-apelin-13 A2 (4)
R = KFRRQ- apelin-17 A2 (5)

D-Leu5-pyr-1-apelin-13 A2 (8)
D-Leu9-apelin-17 A2 (9)

*N*MeLeu5-pyr-1-apelin-13 A2 (10)
*N*MeLeu9-apelin-17 A2 (11)

αMeArg4-pyr-1-apelin-13 A2 (12)
αMeArg8-apelin-17 A2 (13)

αMeLeu5-pyr-1-apelin-13 A2 (14)
αMeLeu9-apelin-17 A2 (15)

azaArg4-pyr-1-apelin-13 A2 (16)
azaArg8-apelin-17 A2 (17)

azaLeu5-pyr-1-apelin-13 A2 (18)
azaLeu9-apelin-17 A2 (19)

$R_1$ = pyrGlu- pyr-1-apelin-13 A2 analogue
$R_2$ = Lys-Phe-Arg-Arg-Gln- apelin-17 A2 analogue 40 41 42 43 44 45

1 4 8 10
12 14 16 18

2 5 9 11
13 15 17 19

2

SEQUENCE LISTING

```
<160> NUMBER OF SEQ ID NOS: 54

<210> SEQ ID NO 1
<211> LENGTH: 12
<212> TYPE: PRT
<213> ORGANISM: Homo sapiens

<400> SEQUENCE: 1

Arg Pro Arg Leu Ser His Lys Gly Pro Met Pro Phe
1               5                   10


<210> SEQ ID NO 2
<211> LENGTH: 17
<212> TYPE: PRT
<213> ORGANISM: Homo sapiens

<400> SEQUENCE: 2

Lys Phe Arg Arg Gln Arg Pro Arg Leu Ser His Lys Gly Pro Met Pro
1               5                   10                  15

Phe


<210> SEQ ID NO 3
<211> LENGTH: 36
<212> TYPE: PRT
<213> ORGANISM: Homo sapiens

<400> SEQUENCE: 3
```

Leu Val Gln Pro Arg Gly Ser Arg Asn Gly Pro Gly Pro Trp Gln Gly
1 5 10 15

Gly Arg Arg Lys Phe Arg Arg Gln Arg Pro Arg Leu Ser His Lys Gly
20 25 30

Pro Met Pro Phe
35

<210> SEQ ID NO 4
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is p-Glu
<220> FEATURE:
<221> NAME/KEY: MISC_FEATURE
<222> LOCATION: (11)..(11)
<223> OTHER INFORMATION: Xaa is Norleucine
<220> FEATURE:
<221> NAME/KEY: MISC_FEATURE
<222> LOCATION: (12)..(12)
<223> OTHER INFORMATION: Xaa is alpha-aminoisobutryic acid
<220> FEATURE:
<221> NAME/KEY: MISC_FEATURE
<222> LOCATION: (13)..(13)
<223> OTHER INFORMATION: Xaa is paraBrPhe

<400> SEQUENCE: 4

Xaa Arg Pro Arg Leu Ser His Lys Gly Pro Xaa Xaa Xaa
1 5 10

<210> SEQ ID NO 5
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (15)..(15)
<223> OTHER INFORMATION: Xaa is Norleucine
<220> FEATURE:
<221> NAME/KEY: MISC_FEATURE
<222> LOCATION: (16)..(16)
<223> OTHER INFORMATION: Xaa is alpha-aminoisobutryic acid
<220> FEATURE:
<221> NAME/KEY: MISC_FEATURE
<222> LOCATION: (17)..(17)
<223> OTHER INFORMATION: Xaa is paraBrPhe

<400> SEQUENCE: 5

Lys Phe Arg Arg Gln Arg Pro Arg Leu Ser His Lys Gly Pro Xaa Xaa
1 5 10 15

Xaa

<210> SEQ ID NO 6
<211> LENGTH: 77
<212> TYPE: PRT
<213> ORGANISM: Homo sapiens

<400> SEQUENCE: 6

Met Asn Leu Arg Leu Cys Val Gln Ala Leu Leu Leu Leu Trp Leu Ser
1 5 10 15

Leu Thr Ala Val Cys Gly Gly Ser Leu Met Pro Leu Pro Asp Gly Asn
20 25 30

```
Gly Leu Glu Asp Gly Asn Val Arg His Leu Val Gln Pro Arg Gly Ser
        35                  40                  45

Arg Asn Gly Pro Gly Pro Trp Gln Gly Gly Arg Arg Lys Phe Arg Arg
    50                  55                  60

Gln Arg Pro Arg Leu Ser His Lys Gly Pro Met Pro Phe
65                  70                  75


<210> SEQ ID NO 7
<211> LENGTH: 13
<212> TYPE: PRT
<213> ORGANISM: Homo sapiens

<400> SEQUENCE: 7

Gln Arg Pro Arg Leu Ser His Lys Gly Pro Met Pro Phe
1               5                   10


<210> SEQ ID NO 8

<400> SEQUENCE: 8

000


<210> SEQ ID NO 9

<400> SEQUENCE: 9

000


<210> SEQ ID NO 10
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pGlu
<220> FEATURE:
<221> NAME/KEY: MISC_FEATURE
<222> LOCATION: (4)..(4)
<223> OTHER INFORMATION: Xaa is NMeArg
<220> FEATURE:
<221> NAME/KEY: MISC_FEATURE
<222> LOCATION: (11)..(11)
<223> OTHER INFORMATION: Xaa is Norleucine
<220> FEATURE:
<221> NAME/KEY: MISC_FEATURE
<222> LOCATION: (12)..(12)
<223> OTHER INFORMATION: Xaa is alpha-aminoisobutryic acid
<220> FEATURE:
<221> NAME/KEY: MISC_FEATURE
<222> LOCATION: (13)..(13)
<223> OTHER INFORMATION: Xaa is paraBrPhe

<400> SEQUENCE: 10

Xaa Arg Pro Xaa Leu Ser His Lys Gly Pro Xaa Xaa Xaa
1               5                   10


<210> SEQ ID NO 11
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa is NMeLeu
```

```
<220> FEATURE:
<221> NAME/KEY: MISC_FEATURE
<222> LOCATION: (15)..(15)
<223> OTHER INFORMATION: Xaa is Norleucine
<220> FEATURE:
<221> NAME/KEY: MISC_FEATURE
<222> LOCATION: (16)..(16)
<223> OTHER INFORMATION: Xaa is alpha-aminoisobutryic acid
<220> FEATURE:
<221> NAME/KEY: MISC_FEATURE
<222> LOCATION: (17)..(17)
<223> OTHER INFORMATION: Xaa is paraBrPhe

<400> SEQUENCE: 11

Lys Phe Arg Arg Gln Arg Pro Arg Xaa Ser His Lys Gly Pro Xaa Xaa
1               5                   10                  15

Xaa


<210> SEQ ID NO 12
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is D-Leu
<220> FEATURE:
<221> NAME/KEY: MISC_FEATURE
<222> LOCATION: (10)..(10)
<223> OTHER INFORMATION: Xaa is Norleucine
<220> FEATURE:
<221> NAME/KEY: MISC_FEATURE
<222> LOCATION: (11)..(11)
<223> OTHER INFORMATION: Xaa is alpha-aminoisobutryic acid
<220> FEATURE:
<221> NAME/KEY: MISC_FEATURE
<222> LOCATION: (12)..(12)
<223> OTHER INFORMATION: Xaa is paraBrPhe

<400> SEQUENCE: 12

Arg Pro Arg Xaa Ser His Lys Gly Pro Xaa Xaa Xaa
1               5                   10


<210> SEQ ID NO 13
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is NMeLeu
<220> FEATURE:
<221> NAME/KEY: MISC_FEATURE
<222> LOCATION: (10)..(10)
<223> OTHER INFORMATION: Xaa is Norleucine
<220> FEATURE:
<221> NAME/KEY: MISC_FEATURE
<222> LOCATION: (11)..(11)
<223> OTHER INFORMATION: Xaa is alpha-aminoisobutryic acid
<220> FEATURE:
<221> NAME/KEY: MISC_FEATURE
<222> LOCATION: (12)..(12)
<223> OTHER INFORMATION: Xaa is alpha-aminoisobutryic acid

<400> SEQUENCE: 13

Arg Pro Arg Xaa Ser His Lys Gly Pro Xaa Xaa Xaa
1               5                   10
```

<210> SEQ ID NO 14
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is alphaMeArg
<220> FEATURE:
<221> NAME/KEY: MISC_FEATURE
<222> LOCATION: (11)..(11)
<223> OTHER INFORMATION: Xaa is Norleucine
<220> FEATURE:
<221> NAME/KEY: MISC_FEATURE
<222> LOCATION: (12)..(12)
<223> OTHER INFORMATION: Xaa is alpha-aminoisobutryic acid
<220> FEATURE:
<221> NAME/KEY: MISC_FEATURE
<222> LOCATION: (13)..(13)
<223> OTHER INFORMATION: Xaa is paraBrPhe

<400> SEQUENCE: 14

```
Arg Pro Xaa Arg Leu Ser His Lys Gly Pro Xaa Xaa Xaa
1               5                   10
```

<210> SEQ ID NO 15
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is azaArg
<220> FEATURE:
<221> NAME/KEY: MISC_FEATURE
<222> LOCATION: (10)..(10)
<223> OTHER INFORMATION: Xaa is Norleucine
<220> FEATURE:
<221> NAME/KEY: MISC_FEATURE
<222> LOCATION: (11)..(11)
<223> OTHER INFORMATION: Xaa is alpha-aminoisobutryic acid
<220> FEATURE:
<221> NAME/KEY: MISC_FEATURE
<222> LOCATION: (12)..(12)
<223> OTHER INFORMATION: Xaa is paraBrPhe

<400> SEQUENCE: 15

```
Arg Pro Arg Xaa Ser His Lys Gly Pro Xaa Xaa Xaa
1               5                   10
```

<210> SEQ ID NO 16
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is azaArg
<220> FEATURE:
<221> NAME/KEY: MISC_FEATURE
<222> LOCATION: (10)..(10)
<223> OTHER INFORMATION: Xaa is Norleucine
<220> FEATURE:
<221> NAME/KEY: MISC_FEATURE
<222> LOCATION: (11)..(11)
<223> OTHER INFORMATION: Xaa is alpha-aminoisobutryic acid
<220> FEATURE:
<221> NAME/KEY: MISC_FEATURE
<222> LOCATION: (12)..(12)

<223> OTHER INFORMATION: Xaa is paraBrPhe

<400> SEQUENCE: 16

Arg Pro Xaa Leu Ser His Lys Gly Pro Xaa Xaa Xaa
1 5 10

<210> SEQ ID NO 17
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is azaLeu
<220> FEATURE:
<221> NAME/KEY: MISC_FEATURE
<222> LOCATION: (10)..(10)
<223> OTHER INFORMATION: Xaa is Norleucine
<220> FEATURE:
<221> NAME/KEY: MISC_FEATURE
<222> LOCATION: (11)..(11)
<223> OTHER INFORMATION: Xaa is alpha-aminoisobutryic acid
<220> FEATURE:
<221> NAME/KEY: MISC_FEATURE
<222> LOCATION: (12)..(12)
<223> OTHER INFORMATION: Xaa is paraBrPhe

<400> SEQUENCE: 17

Arg Pro Arg Xaa Ser His Lys Gly Pro Xaa Xaa Xaa
1 5 10

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is D-Leu

<400> SEQUENCE: 18

Arg Pro Arg Xaa Ser His Lys Gly Pro
1 5

<210> SEQ ID NO 19
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is NMeLeu

<400> SEQUENCE: 19

Arg Pro Arg Xaa Ser His Lys Gly Pro
1 5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is alphaMeArg

<400> SEQUENCE: 20

Arg Pro Xaa Leu Ser His Lys Gly Pro
1 5

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is alphaMeLeu

<400> SEQUENCE: 21

Arg Pro Arg Xaa Ser His Lys Gly Pro
1 5

<210> SEQ ID NO 22
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is azaArg

<400> SEQUENCE: 22

Arg Pro Xaa Leu Ser His Lys Gly Pro
1 5

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is azaLeu

<400> SEQUENCE: 23

Arg Pro Arg Xaa Ser His Lys Gly Pro
1 5

<210> SEQ ID NO 24
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pGlu
<220> FEATURE:
<221> NAME/KEY: MISC_FEATURE
<222> LOCATION: (5)..(5)
<223> OTHER INFORMATION: Xaa is D-Leu
<220> FEATURE:
<221> NAME/KEY: MISC_FEATURE
<222> LOCATION: (11)..(11)
<223> OTHER INFORMATION: Xaa is Norleucine
<220> FEATURE:

<221> NAME/KEY: MISC_FEATURE
<222> LOCATION: (12)..(12)
<223> OTHER INFORMATION: Xaa is alpha-aminoisobutryic acid
<220> FEATURE:
<221> NAME/KEY: MISC_FEATURE
<222> LOCATION: (13)..(13)
<223> OTHER INFORMATION: Xaa is paraBrPhe

<400> SEQUENCE: 24

Xaa Arg Pro Arg Xaa Ser His Lys Gly Pro Xaa Xaa Xaa
1               5                   10

<210> SEQ ID NO 25
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa is D-Leu
<220> FEATURE:
<221> NAME/KEY: MISC_FEATURE
<222> LOCATION: (15)..(15)
<223> OTHER INFORMATION: Xaa is Norleucine
<220> FEATURE:
<221> NAME/KEY: MISC_FEATURE
<222> LOCATION: (16)..(16)
<223> OTHER INFORMATION: Xaa is alpha-aminoisobutryic acid
<220> FEATURE:
<221> NAME/KEY: MISC_FEATURE
<222> LOCATION: (17)..(17)
<223> OTHER INFORMATION: Xaa is paraBrPhe

<400> SEQUENCE: 25

Lys Phe Arg Arg Gln Arg Pro Arg Xaa Ser His Lys Gly Pro Xaa Xaa
1               5                   10                  15

Xaa

<210> SEQ ID NO 26
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pGlu
<220> FEATURE:
<221> NAME/KEY: MISC_FEATURE
<222> LOCATION: (5)..(5)
<223> OTHER INFORMATION: Xaa is NMeLeu
<220> FEATURE:
<221> NAME/KEY: MISC_FEATURE
<222> LOCATION: (11)..(11)
<223> OTHER INFORMATION: Xaa is Norleucine
<220> FEATURE:
<221> NAME/KEY: MISC_FEATURE
<222> LOCATION: (12)..(12)
<223> OTHER INFORMATION: Xaa is alpha-aminoisobutryic acid
<220> FEATURE:
<221> NAME/KEY: MISC_FEATURE
<222> LOCATION: (13)..(13)
<223> OTHER INFORMATION: Xaa is paraBrPhe

<400> SEQUENCE: 26

Xaa Arg Pro Arg Xaa Ser His Lys Gly Pro Xaa Xaa Xaa
1               5                   10

<210> SEQ ID NO 27

<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa is NMeLeu
<220> FEATURE:
<221> NAME/KEY: MISC_FEATURE
<222> LOCATION: (15)..(15)
<223> OTHER INFORMATION: Xaa is Norleucine
<220> FEATURE:
<221> NAME/KEY: MISC_FEATURE
<222> LOCATION: (16)..(16)
<223> OTHER INFORMATION: Xaa is alpha-aminoisobutryic acid
<220> FEATURE:
<221> NAME/KEY: MISC_FEATURE
<222> LOCATION: (17)..(17)
<223> OTHER INFORMATION: Xaa is paraBrPhe

<400> SEQUENCE: 27

```
Lys Phe Arg Arg Gln Arg Pro Arg Xaa Ser His Lys Gly Pro Xaa Xaa
1               5                   10                  15

Xaa
```

<210> SEQ ID NO 28
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pGlu
<220> FEATURE:
<221> NAME/KEY: MISC_FEATURE
<222> LOCATION: (4)..(4)
<223> OTHER INFORMATION: Xaa is alphaMeArg
<220> FEATURE:
<221> NAME/KEY: MISC_FEATURE
<222> LOCATION: (11)..(11)
<223> OTHER INFORMATION: Xaa is Norleucine
<220> FEATURE:
<221> NAME/KEY: MISC_FEATURE
<222> LOCATION: (12)..(12)
<223> OTHER INFORMATION: Xaa is alpha-aminoisobutryic acid
<220> FEATURE:
<221> NAME/KEY: MISC_FEATURE
<222> LOCATION: (13)..(13)
<223> OTHER INFORMATION: Xaa is paraBrPhe

<400> SEQUENCE: 28

```
Xaa Arg Pro Xaa Leu Ser His Lys Gly Pro Xaa Xaa Xaa
1               5                   10
```

<210> SEQ ID NO 29
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is alphaMeArg
<220> FEATURE:
<221> NAME/KEY: MISC_FEATURE
<222> LOCATION: (15)..(15)
<223> OTHER INFORMATION: Xaa is Norleucine
<220> FEATURE:
<221> NAME/KEY: MISC_FEATURE
<222> LOCATION: (16)..(16)
<223> OTHER INFORMATION: Xaa is alpha-aminoisobutryic acid
<220> FEATURE:
<221> NAME/KEY: MISC_FEATURE
<222> LOCATION: (17)..(17)
<223> OTHER INFORMATION: Xaa is paraBrPhe

<400> SEQUENCE: 29

Lys Phe Arg Arg Gln Arg Pro Xaa Leu Ser His Lys Gly Pro Xaa Xaa
1 5 10 15

Xaa

<210> SEQ ID NO 30
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pGlu
<220> FEATURE:
<221> NAME/KEY: MISC_FEATURE
<222> LOCATION: (5)..(5)
<223> OTHER INFORMATION: Xaa is alphaMeLeu
<220> FEATURE:
<221> NAME/KEY: MISC_FEATURE
<222> LOCATION: (11)..(11)
<223> OTHER INFORMATION: Xaa is Norleucine
<220> FEATURE:
<221> NAME/KEY: MISC_FEATURE
<222> LOCATION: (12)..(12)
<223> OTHER INFORMATION: Xaa is alpha-aminoisobutryic acid
<220> FEATURE:
<221> NAME/KEY: MISC_FEATURE
<222> LOCATION: (13)..(13)
<223> OTHER INFORMATION: Xaa is paraBrPhe

<400> SEQUENCE: 30

Xaa Arg Pro Arg Xaa Ser His Lys Gly Pro Xaa Xaa Xaa
1 5 10

<210> SEQ ID NO 31
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa is alphaMeLeu
<220> FEATURE:
<221> NAME/KEY: MISC_FEATURE
<222> LOCATION: (15)..(15)
<223> OTHER INFORMATION: Xaa is Norleucine
<220> FEATURE:
<221> NAME/KEY: MISC_FEATURE
<222> LOCATION: (16)..(16)
<223> OTHER INFORMATION: Xaa is alpha-aminoisobutryic acid
<220> FEATURE:
<221> NAME/KEY: MISC_FEATURE
<222> LOCATION: (17)..(17)
<223> OTHER INFORMATION: Xaa is paraBrPhe

<400> SEQUENCE: 31

Lys Phe Arg Arg Gln Arg Pro Arg Xaa Ser His Lys Gly Pro Xaa Xaa
1 5 10 15

Xaa

<210> SEQ ID NO 32
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is azaArg
<220> FEATURE:
<221> NAME/KEY: MISC_FEATURE
<222> LOCATION: (15)..(15)
<223> OTHER INFORMATION: Xaa is Norleucine
<220> FEATURE:
<221> NAME/KEY: MISC_FEATURE
<222> LOCATION: (16)..(16)
<223> OTHER INFORMATION: Xaa is alpha-aminoisobutryic acid
<220> FEATURE:
<221> NAME/KEY: MISC_FEATURE
<222> LOCATION: (17)..(17)
<223> OTHER INFORMATION: Xaa is paraBrPhe

<400> SEQUENCE: 32

```
Lys Phe Arg Arg Gln Arg Pro Xaa Leu Ser His Lys Gly Pro Xaa Xaa
1               5                   10                  15

Xaa
```

<210> SEQ ID NO 33
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pGlu
<220> FEATURE:
<221> NAME/KEY: MISC_FEATURE
<222> LOCATION: (5)..(5)
<223> OTHER INFORMATION: Xaa is azaLeu
<220> FEATURE:
<221> NAME/KEY: MISC_FEATURE
<222> LOCATION: (11)..(11)
<223> OTHER INFORMATION: Xaa is Norleucine
<220> FEATURE:
<221> NAME/KEY: MISC_FEATURE
<222> LOCATION: (12)..(12)
<223> OTHER INFORMATION: Xaa is alpha-aminoisobutryic acid
<220> FEATURE:
<221> NAME/KEY: MISC_FEATURE
<222> LOCATION: (13)..(13)
<223> OTHER INFORMATION: Xaa is paraBrPhe

<400> SEQUENCE: 33

```
Xaa Arg Pro Arg Xaa Ser His Lys Gly Pro Xaa Xaa Xaa
1               5                   10
```

<210> SEQ ID NO 34
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa is azaLeu
<220> FEATURE:
<221> NAME/KEY: MISC_FEATURE
<222> LOCATION: (15)..(15)
<223> OTHER INFORMATION: Xaa is Norleucine
<220> FEATURE:

<221> NAME/KEY: MISC_FEATURE
<222> LOCATION: (16)..(16)
<223> OTHER INFORMATION: Xaa is alpha-aminoisobutryic acid
<220> FEATURE:
<221> NAME/KEY: MISC_FEATURE
<222> LOCATION: (17)..(17)
<223> OTHER INFORMATION: Xaa is paraBrPhe

<400> SEQUENCE: 34

Lys Phe Arg Arg Gln Arg Pro Arg Xaa Ser His Lys Gly Pro Xaa Xaa
1               5                   10                  15

Xaa

<210> SEQ ID NO 35
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (12)..(12)
<223> OTHER INFORMATION: Xaa is Norleucine
<220> FEATURE:
<221> NAME/KEY: MISC_FEATURE
<222> LOCATION: (13)..(13)
<223> OTHER INFORMATION: Xaa is alpha-aminoisobutryic acid
<220> FEATURE:
<221> NAME/KEY: MISC_FEATURE
<222> LOCATION: (14)..(14)
<223> OTHER INFORMATION: Xaa is paraBrPhe

<400> SEQUENCE: 35

Arg Gln Arg Pro Arg Leu Ser His Lys Gly Pro Xaa Xaa Xaa
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa is NMeLeu
<220> FEATURE:
<221> NAME/KEY: MISC_FEATURE
<222> LOCATION: (12)..(12)
<223> OTHER INFORMATION: Xaa is Norleucine
<220> FEATURE:
<221> NAME/KEY: MISC_FEATURE
<222> LOCATION: (13)..(13)
<223> OTHER INFORMATION: Xaa is alpha-aminoisobutryic acid
<220> FEATURE:
<221> NAME/KEY: MISC_FEATURE
<222> LOCATION: (14)..(14)
<223> OTHER INFORMATION: Xaa is paraBrPhe

<400> SEQUENCE: 36

Arg Gln Arg Pro Arg Xaa Ser His Lys Gly Pro Xaa Xaa Xaa
1               5                   10

<210> SEQ ID NO 37
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)

<223> OTHER INFORMATION: Xaa is Palmitoylation
<220> FEATURE:
<221> NAME/KEY: MISC_FEATURE
<222> LOCATION: (16)..(16)
<223> OTHER INFORMATION: Xaa is Norleucine
<220> FEATURE:
<221> NAME/KEY: MISC_FEATURE
<222> LOCATION: (17)..(17)
<223> OTHER INFORMATION: Xaa is alpha-aminoisobutryic acid
<220> FEATURE:
<221> NAME/KEY: MISC_FEATURE
<222> LOCATION: (18)..(18)
<223> OTHER INFORMATION: Xaa is paraBrPhe

<400> SEQUENCE: 37

Xaa Lys Phe Arg Arg Gln Arg Pro Arg Leu Ser His Lys Gly Pro Xaa
1 5 10 15

Xaa Xaa

<210> SEQ ID NO 38
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Pegylation
<220> FEATURE:
<221> NAME/KEY: MISC_FEATURE
<222> LOCATION: (16)..(16)
<223> OTHER INFORMATION: Xaa is Norleucine
<220> FEATURE:
<221> NAME/KEY: MISC_FEATURE
<222> LOCATION: (17)..(17)
<223> OTHER INFORMATION: Xaa is alpha-aminoisobutryic acid
<220> FEATURE:
<221> NAME/KEY: MISC_FEATURE
<222> LOCATION: (18)..(18)
<223> OTHER INFORMATION: Xaa is paraBrPhe

<400> SEQUENCE: 38

Xaa Lys Phe Arg Arg Gln Arg Pro Arg Leu Ser His Lys Gly Pro Xaa
1 5 10 15

Xaa Xaa

<210> SEQ ID NO 39
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Palmitoylation
<220> FEATURE:
<221> NAME/KEY: MISC_FEATURE
<222> LOCATION: (10)..(10)
<223> OTHER INFORMATION: Xaa is NMeLeu
<220> FEATURE:
<221> NAME/KEY: MISC_FEATURE
<222> LOCATION: (16)..(16)
<223> OTHER INFORMATION: Xaa is Norleucine
<220> FEATURE:
<221> NAME/KEY: MISC_FEATURE
<222> LOCATION: (17)..(17)
<223> OTHER INFORMATION: Xaa is alpha-aminoisobutryic acid
<220> FEATURE:
<221> NAME/KEY: MISC_FEATURE
<222> LOCATION: (18)..(18)
<223> OTHER INFORMATION: Xaa is paraBrPhe

<400> SEQUENCE: 39

Xaa Lys Phe Arg Arg Gln Arg Pro Arg Xaa Ser His Lys Gly Pro Xaa
1 5 10 15

Xaa Xaa

<210> SEQ ID NO 40
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Pegylation
<220> FEATURE:
<221> NAME/KEY: MISC_FEATURE
<222> LOCATION: (10)..(10)
<223> OTHER INFORMATION: Xaa is NMeLeu
<220> FEATURE:
<221> NAME/KEY: MISC_FEATURE
<222> LOCATION: (16)..(16)
<223> OTHER INFORMATION: Xaa is Norleucine
<220> FEATURE:
<221> NAME/KEY: MISC_FEATURE
<222> LOCATION: (17)..(17)
<223> OTHER INFORMATION: Xaa is alpha-aminoisobutryic acid
<220> FEATURE:
<221> NAME/KEY: MISC_FEATURE
<222> LOCATION: (18)..(18)
<223> OTHER INFORMATION: Xaa is paraBrPhe

<400> SEQUENCE: 40

Xaa Lys Phe Arg Arg Gln Arg Pro Arg Xaa Ser His Lys Gly Pro Xaa
1 5 10 15

Xaa Xaa

<210> SEQ ID NO 41
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Palmitoylation
<220> FEATURE:
<221> NAME/KEY: MISC_FEATURE
<222> LOCATION: (10)..(10)
<223> OTHER INFORMATION: Xaa is D-Leu
<220> FEATURE:
<221> NAME/KEY: MISC_FEATURE
<222> LOCATION: (16)..(16)
<223> OTHER INFORMATION: Xaa is Norleucine
<220> FEATURE:
<221> NAME/KEY: MISC_FEATURE
<222> LOCATION: (17)..(17)
<223> OTHER INFORMATION: Xaa is alpha-aminoisobutryic acid
<220> FEATURE:
<221> NAME/KEY: MISC_FEATURE
<222> LOCATION: (18)..(18)
<223> OTHER INFORMATION: Xaa is paraBrPhe

<400> SEQUENCE: 41

Xaa Lys Phe Arg Arg Gln Arg Pro Arg Xaa Ser His Lys Gly Pro Xaa
1 5 10 15

Xaa Xaa

<210> SEQ ID NO 42
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Palmitoylation
<220> FEATURE:
<221> NAME/KEY: MISC_FEATURE
<222> LOCATION: (9)..(9)
<223> OTHER INFORMATION: Xaa is alphaMeArg
<220> FEATURE:
<221> NAME/KEY: MISC_FEATURE
<222> LOCATION: (16)..(16)
<223> OTHER INFORMATION: Xaa is Norleucine
<220> FEATURE:
<221> NAME/KEY: MISC_FEATURE
<222> LOCATION: (17)..(17)
<223> OTHER INFORMATION: Xaa is alpha-aminoisobutryic acid
<220> FEATURE:
<221> NAME/KEY: MISC_FEATURE
<222> LOCATION: (18)..(18)
<223> OTHER INFORMATION: Xaa is paraBrPhe

<400> SEQUENCE: 42

```
Xaa Lys Phe Arg Arg Gln Arg Pro Xaa Leu Ser His Lys Gly Pro Xaa
1               5                   10                  15

Xaa Xaa
```

<210> SEQ ID NO 43
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Palmitoylation
<220> FEATURE:
<221> NAME/KEY: MISC_FEATURE
<222> LOCATION: (10)..(10)
<223> OTHER INFORMATION: Xaa is alphaMeLeu
<220> FEATURE:
<221> NAME/KEY: MISC_FEATURE
<222> LOCATION: (16)..(16)
<223> OTHER INFORMATION: Xaa is Norleucine
<220> FEATURE:
<221> NAME/KEY: MISC_FEATURE
<222> LOCATION: (17)..(17)
<223> OTHER INFORMATION: Xaa is alpha-aminoisobutryic acid
<220> FEATURE:
<221> NAME/KEY: MISC_FEATURE
<222> LOCATION: (18)..(18)
<223> OTHER INFORMATION: Xaa is paraBrPhe

<400> SEQUENCE: 43

```
Xaa Lys Phe Arg Arg Gln Arg Pro Arg Xaa Ser His Lys Gly Pro Xaa
1               5                   10                  15

Xaa Xaa
```

<210> SEQ ID NO 44
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)

<223> OTHER INFORMATION: Xaa is Palmitoylation
<220> FEATURE:
<221> NAME/KEY: MISC_FEATURE
<222> LOCATION: (9)..(9)
<223> OTHER INFORMATION: Xaa is azaArg
<220> FEATURE:
<221> NAME/KEY: MISC_FEATURE
<222> LOCATION: (16)..(16)
<223> OTHER INFORMATION: Xaa is Norleucine
<220> FEATURE:
<221> NAME/KEY: MISC_FEATURE
<222> LOCATION: (17)..(17)
<223> OTHER INFORMATION: Xaa is alpha-aminoisobutryic acid
<220> FEATURE:
<221> NAME/KEY: MISC_FEATURE
<222> LOCATION: (18)..(18)
<223> OTHER INFORMATION: Xaa is paraBrPhe

<400> SEQUENCE: 44

Xaa Lys Phe Arg Arg Gln Arg Pro Xaa Leu Ser His Lys Gly Pro Xaa
1               5                   10                  15

Xaa Xaa

<210> SEQ ID NO 45
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Palmitoylation
<220> FEATURE:
<221> NAME/KEY: MISC_FEATURE
<222> LOCATION: (10)..(10)
<223> OTHER INFORMATION: Xaa is azaLeu
<220> FEATURE:
<221> NAME/KEY: MISC_FEATURE
<222> LOCATION: (16)..(16)
<223> OTHER INFORMATION: Xaa is Norleucine
<220> FEATURE:
<221> NAME/KEY: MISC_FEATURE
<222> LOCATION: (17)..(17)
<223> OTHER INFORMATION: Xaa is alpha-aminoisobutryic acid
<220> FEATURE:
<221> NAME/KEY: MISC_FEATURE
<222> LOCATION: (18)..(18)
<223> OTHER INFORMATION: Xaa is paraBrPhe

<400> SEQUENCE: 45

Xaa Lys Phe Arg Arg Gln Arg Pro Arg Xaa Ser His Lys Gly Pro Xaa
1               5                   10                  15

Xaa Xaa

<210> SEQ ID NO 46
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Pegylation
<220> FEATURE:
<221> NAME/KEY: MISC_FEATURE
<222> LOCATION: (10)..(10)
<223> OTHER INFORMATION: Xaa is D-Leu
<220> FEATURE:
<221> NAME/KEY: MISC_FEATURE
<222> LOCATION: (16)..(16)
<223> OTHER INFORMATION: Xaa is Norleucine
<220> FEATURE:
<221> NAME/KEY: MISC_FEATURE
<222> LOCATION: (17)..(17)
<223> OTHER INFORMATION: Xaa is alpha-aminoisobutryic acid
<220> FEATURE:
<221> NAME/KEY: MISC_FEATURE
<222> LOCATION: (18)..(18)
<223> OTHER INFORMATION: Xaa is paraBrPhe

<400> SEQUENCE: 46

Xaa Lys Phe Arg Arg Gln Arg Pro Arg Xaa Ser His Lys Gly Pro Xaa
1 5 10 15

Xaa Xaa

<210> SEQ ID NO 47
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Pegylation
<220> FEATURE:
<221> NAME/KEY: MISC_FEATURE
<222> LOCATION: (9)..(9)
<223> OTHER INFORMATION: Xaa is alphaMeArg
<220> FEATURE:
<221> NAME/KEY: MISC_FEATURE
<222> LOCATION: (16)..(16)
<223> OTHER INFORMATION: Xaa is Norleucine
<220> FEATURE:
<221> NAME/KEY: MISC_FEATURE
<222> LOCATION: (17)..(17)
<223> OTHER INFORMATION: Xaa is alpha-aminoisobutryic acid
<220> FEATURE:
<221> NAME/KEY: MISC_FEATURE
<222> LOCATION: (18)..(18)
<223> OTHER INFORMATION: Xaa is paraBrPhe

<400> SEQUENCE: 47

Xaa Lys Phe Arg Arg Gln Arg Pro Xaa Leu Ser His Lys Gly Pro Xaa
1 5 10 15

Xaa Xaa

<210> SEQ ID NO 48
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Pegylation
<220> FEATURE:
<221> NAME/KEY: MISC_FEATURE
<222> LOCATION: (10)..(10)
<223> OTHER INFORMATION: Xaa is alphaMeLeu
<220> FEATURE:
<221> NAME/KEY: MISC_FEATURE
<222> LOCATION: (16)..(16)
<223> OTHER INFORMATION: Xaa is Norleucine
<220> FEATURE:
<221> NAME/KEY: MISC_FEATURE
<222> LOCATION: (17)..(17)
<223> OTHER INFORMATION: Xaa is alpha-aminoisobutryic acid
<220> FEATURE:
<221> NAME/KEY: MISC_FEATURE
<222> LOCATION: (18)..(18)
<223> OTHER INFORMATION: Xaa is paraBrPhe

<400> SEQUENCE: 48

Xaa Lys Phe Arg Arg Gln Arg Pro Arg Xaa Ser His Lys Gly Pro Xaa
1 5 10 15

Xaa Xaa

<210> SEQ ID NO 49
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Pegylation
<220> FEATURE:
<221> NAME/KEY: MISC_FEATURE
<222> LOCATION: (9)..(9)
<223> OTHER INFORMATION: Xaa is azaArg
<220> FEATURE:
<221> NAME/KEY: MISC_FEATURE
<222> LOCATION: (16)..(16)
<223> OTHER INFORMATION: Xaa is Norleucine
<220> FEATURE:
<221> NAME/KEY: MISC_FEATURE
<222> LOCATION: (17)..(17)
<223> OTHER INFORMATION: Xaa is alpha-aminoisobutryic acid
<220> FEATURE:
<221> NAME/KEY: MISC_FEATURE
<222> LOCATION: (18)..(18)
<223> OTHER INFORMATION: Xaa is paraBrPhe

<400> SEQUENCE: 49

Xaa Lys Phe Arg Arg Gln Arg Pro Xaa Leu Ser His Lys Gly Pro Xaa
1 5 10 15

Xaa Xaa

<210> SEQ ID NO 50
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Pegylation
<220> FEATURE:
<221> NAME/KEY: MISC_FEATURE
<222> LOCATION: (10)..(10)
<223> OTHER INFORMATION: Xaa is azaLeu
<220> FEATURE:
<221> NAME/KEY: MISC_FEATURE
<222> LOCATION: (16)..(16)
<223> OTHER INFORMATION: Xaa is Norleucine
<220> FEATURE:
<221> NAME/KEY: MISC_FEATURE
<222> LOCATION: (17)..(17)
<223> OTHER INFORMATION: Xaa is alpha-aminoisobutryic acid
<220> FEATURE:
<221> NAME/KEY: MISC_FEATURE
<222> LOCATION: (18)..(18)
<223> OTHER INFORMATION: Xaa is paraBrPhe

<400> SEQUENCE: 50

Xaa Lys Phe Arg Arg Gln Arg Pro Arg Xaa Ser His Lys Gly Pro Xaa
1 5 10 15

Xaa Xaa

<210> SEQ ID NO 51

```
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is pGlu
<220> FEATURE:
<221> NAME/KEY: MISC_FEATURE
<222> LOCATION: (4)..(4)
<223> OTHER INFORMATION: Xaa is azaArg
<220> FEATURE:
<221> NAME/KEY: MISC_FEATURE
<222> LOCATION: (11)..(11)
<223> OTHER INFORMATION: Xaa is Norleucine
<220> FEATURE:
<221> NAME/KEY: MISC_FEATURE
<222> LOCATION: (12)..(12)
<223> OTHER INFORMATION: Xaa is alpha-aminoisobutryic acid
<220> FEATURE:
<221> NAME/KEY: MISC_FEATURE
<222> LOCATION: (13)..(13)
<223> OTHER INFORMATION: Xaa is paraBrPhe

<400> SEQUENCE: 51

Xaa Arg Pro Xaa Leu Ser His Lys Gly Pro Xaa Xaa Xaa
1               5                   10


<210> SEQ ID NO 52
<211> LENGTH: 13
<212> TYPE: PRT
<213> ORGANISM: Artificial Sequence
<220> FEATURE:
<223> OTHER INFORMATION: Peptidomimetic
<220> FEATURE:
<221> NAME/KEY: MISC_FEATURE
<222> LOCATION: (1)..(1)
<223> OTHER INFORMATION: Xaa is pGlu
<220> FEATURE:
<221> NAME/KEY: MISC_FEATURE
<222> LOCATION: (2)..(2)
<223> OTHER INFORMATION: Xaa is Arg or a conservative variant
<220> FEATURE:
<221> NAME/KEY: MISC_FEATURE
<222> LOCATION: (3)..(3)
<223> OTHER INFORMATION: Xaa is Pro or a conservative variant thereof
<220> FEATURE:
<221> NAME/KEY: MISC_FEATURE
<222> LOCATION: (4)..(4)
<223> OTHER INFORMATION: Xaa is any amino acid or a conservative variant
      thereof from the group consisting of Arg, Arg-D, alphaMeArg and
      azaArg
<220> FEATURE:
<221> NAME/KEY: MISC_FEATURE
<222> LOCATION: (5)..(5)
<223> OTHER INFORMATION: Xaa is any amino acid or a conservative variant
      thereof from the group consisting of Leu, NMeLeu, alphaMeLeu and
      azaLeu
<220> FEATURE:
<221> NAME/KEY: MISC_FEATURE
<222> LOCATION: (11)..(11)
<223> OTHER INFORMATION: Xaa is Norleucine
<220> FEATURE:
<221> NAME/KEY: MISC_FEATURE
<222> LOCATION: (12)..(12)
<223> OTHER INFORMATION: Xaa is alpha-aminoisobutryic acid
<220> FEATURE:
<221> NAME/KEY: MISC_FEATURE
<222> LOCATION: (13)..(13)
<223> OTHER INFORMATION: Xaa is paraBrPhe

<400> SEQUENCE: 52

Xaa Xaa Xaa Xaa Xaa Ser His Lys Gly Pro Xaa Xaa Xaa
1               5                   10
```

```
<210> SEQ ID NO 53
<211> LENGTH: 17
<212> TYPE: PRT
<213> ORGANISM: Artificial Sequence
<220> FEATURE:
<223> OTHER INFORMATION: Peptidomimetic
<220> FEATURE:
<221> NAME/KEY: MISC_FEATURE
<222> LOCATION: (6)..(6)
<223> OTHER INFORMATION: Xaa is Arg or a conservative variant thereof
<220> FEATURE:
<221> NAME/KEY: MISC_FEATURE
<222> LOCATION: (7)..(7)
<223> OTHER INFORMATION: Xaa is Pro or a conservative variant thereof
<220> FEATURE:
<221> NAME/KEY: MISC_FEATURE
<222> LOCATION: (8)..(8)
<223> OTHER INFORMATION: Xaa is any amino acid or a conservative variant
      thereof from the group consisting of Arg, Arg-D, alphaMeArg and
      azaArg
<220> FEATURE:
<221> NAME/KEY: MISC_FEATURE
<222> LOCATION: (9)..(9)
<223> OTHER INFORMATION: Xaa is any amino acid or a conservative variant
      thereof from the group consisting of Leu, NMeLeu, alphaMeLeu and
      azaLeu
<220> FEATURE:
<221> NAME/KEY: MISC_FEATURE
<222> LOCATION: (15)..(15)
<223> OTHER INFORMATION: Xaa is Norleucine
<220> FEATURE:
<221> NAME/KEY: MISC_FEATURE
<222> LOCATION: (16)..(16)
<223> OTHER INFORMATION: Xaa is alpha-aminoisobutryic acid
<220> FEATURE:
<221> NAME/KEY: MISC_FEATURE
<222> LOCATION: (17)..(17)
<223> OTHER INFORMATION: Xaa is paraBrPhe

<400> SEQUENCE: 53

Lys Phe Arg Arg Gln Xaa Xaa Xaa Xaa Ser His Lys Gly Pro Xaa Xaa
1               5                   10                  15

Xaa


<210> SEQ ID NO 54
<211> LENGTH: 18
<212> TYPE: PRT
<213> ORGANISM: Artificial Sequence
<220> FEATURE:
<223> OTHER INFORMATION: Peptidomimetic
<220> FEATURE:
<221> NAME/KEY: MISC_FEATURE
<222> LOCATION: (1)..(1)
<223> OTHER INFORMATION: Xaa is H or a long chain moiety
<220> FEATURE:
<221> NAME/KEY: MISC_FEATURE
<222> LOCATION: (7)..(7)
<223> OTHER INFORMATION: Xaa is Arg or a conservative variant thereof
<220> FEATURE:
<221> NAME/KEY: MISC_FEATURE
<222> LOCATION: (8)..(8)
<223> OTHER INFORMATION: Xaa Pro or a conservative variant thereof
<220> FEATURE:
<221> NAME/KEY: MISC_FEATURE
<222> LOCATION: (9)..(9)
<223> OTHER INFORMATION: Xaa is any amino acid or a conservative variant
      thereof from the group consisting of Arg, Arg-D, alphaMeArg and
      azaArg
<220> FEATURE:
<221> NAME/KEY: MISC_FEATURE
<222> LOCATION: (10)..(10)
<223> OTHER INFORMATION: Xaa is any amino acid or a conservative variant
      thereof from the group consisting of Leu, NMeLeu, alphaMeLeu and
      azaLeu
```

-continued

```
<220> FEATURE:
<221> NAME/KEY: MISC_FEATURE
<222> LOCATION: (16)..(16)
<223> OTHER INFORMATION: Xaa is Norleucine
<220> FEATURE:
<221> NAME/KEY: MISC_FEATURE
<222> LOCATION: (17)..(17)
<223> OTHER INFORMATION: Xaa is alpha-aminoisobutryic acid
<220> FEATURE:
<221> NAME/KEY: MISC_FEATURE
<222> LOCATION: (18)..(18)
<223> OTHER INFORMATION: Xaa is paraBrPhe

<400> SEQUENCE: 54

Xaa Lys Phe Arg Arg Gln Xaa Xaa Xaa Xaa Ser His Lys Gly Pro Xaa
1               5                   10                  15

Xaa Xaa
```

APELIN PEPTIDES AND USES THEREOF

RELATED APPLICATION INFORMATION

This application claims priority to U.S. Provisional Patent Application No. 62/528,379, filed Jul. 3, 2017. The entire contents of the foregoing application is incorporated herein by reference, including all text, tables, sequence listing and drawings.

SEQUENCE LISTING

The instant application contains a Sequence Listing which has been submitted electronically in ASCII format and is hereby incorporated by reference in its entirety. Said ASCII copy, created on Sep. 25, 2018, is named UofAlberta0459694_ST25.txt and is 28.9 KB in size.

BACKGROUND

Apelin (APLN), the endogenous mammalian peptide ligand of the apelin receptor has been indicated as a regulator of the cardiovascular system. Human apelin is a pre-proprotein of 77 amino acids (MNLRLCVQALLLL-WLSLTAVCGGSLMPLPDGNGLEDGNVRHLVQPRG-SRNGPGPW QGGRRKFRRQRPRLSHKGPMPF (SEQ ID NO: 6)), with a secretory signal sequence in the N-terminal region. After cleavage of the signal peptide at the endoplasmic reticulum, the remaining 55 amino acid residue may undergo further cleavage to several active isoforms including a 36 amino acid peptide corresponding to apelin sequence residues 42-77 (apelin-36, LVQPRGSRNGPGP-WQGGRRKFRR-QRPRLSHKGPMPF, (SEQ ID NO:3)) (3), a 17 amino acid peptide corresponding to the apelin sequence residues 61-77 (apelin-17, KFRRQRPRLSHK-GPMPF (SEQ ID NO:2)) (2) and a 13 amino acid peptide corresponding to the apelin sequence residues 65-77 (apelin-13, QRPRLSHKGPMPF (SEQ ID NO:7)), which all possess a conserved C-terminal amino acid (FIG. 1). The apelin-13 fragment may also undergo subsequent pyroglutamylation at its N-terminal glutamine residue to provide ($pyr^1$) apelin-13 ((Pyr)RPRLSHKGPMPF (SEQ ID NO:1) (1).

Apelin pathway mediates a positive effect on cardiac contractility and vasodilator activity that counteracts angiotensin-II-induced vasoconstriction. Moreover, apelin administration has been indicated to reduce the progression of cardiac hypertrophy, while apelin knockout mice have been shown to be susceptible to heart failure. Apelin also has a beneficial role in the cardiovascular system, such as initiating vasodilation through a NO-mediated mechanism, positive inotropy, angiogenesis, and the prevention of myocardial ischemic reperfusion injury.

Despite the beneficial physiological effects of the apelinergic system, the lifespan of apelin peptides is heavily regulated and limited via proteolysis. The (pyr1) apelin-13 fragment (SEQ ID NO:1), for example, has been indicated as an endogenous ligand for the apelin receptor with an EC50 about 0.37 nM, while (pyr1) apelin-13 exhibits potent vascular effects in vivo. However, (pyr1) apelin-13 stability is quite low in human plasma, with a $t_{1/2}$ of about one minute.

Angiotensin converting enzyme 2 (ACE2) is a well-known monocarboxypeptidase that efficiently catalyzes the removal of the conserved C-terminal phenylalanine from apelin isoforms in vitro and in vivo. Des-phenylalanine apelin isoforms behave as biased agonists by retaining native binding and forskolin-induced cAMP inhibition, but abolishing apelin receptor internalization and β-arrestin recruitment. Studies have shown that truncated peptides demonstrate a diminished capacity to lower blood pressure and have no ability to protect against myocardial ischemic reperfusion injury, making the C-terminal Phe residue essential for full agonist activity. Therefore, there exists a need to negate the impact of ACE2 degradation on apelin isoforms, and to improve the overall stability of the apelin isoforms. Given the therapeutic potential of (pyr1) apelin-13 and related apelin peptides, there is a continued interest in stabilizing the peptide structures while preserving their biological profiles.

SUMMARY

The present disclosure relates to peptide and peptide-like therapeutic agents for the treatment of various diseases and conditions related to the apelin/apelin receptor system. In particular, the present disclosure relates to apelin-based therapeutics and their use in treating various diseases and disorders of the cardiovascular system.

Embodiments disclosed herein relate to apelin peptides, in particular, apelin peptides comprising peptidomimetic of Formula (I): Z1-pGlu-aa2-aa3-aa4-aa5-aa6-aa7-aa8-aa9-aa10-aa11-aa12-aa13, or pharmaceutically acceptable salts thereof, wherein Z1 is H or a long chain moiety, wherein each of aa2, aa3, aa4, aa5, aa6, aa7, aa8, aa9, aa10, aa11, aa12, and aa13 is independently an amino acid, wherein: aa2 comprises Arg or a conservative variant thereof; aa3 comprises Pro or a conservative variant thereof; aa4 comprises an amino acid or a conservative variant thereof selected from the group consisting of Arg, Arg-D, αMeArg and azaArg; aa5 comprises an amino acid or a conservative variant thereof selected from the group consisting of Leu, NMeLeu, αMeLeu and azaLeu; aa6 comprises Ser or a conservative variant thereof; aa7 comprises His or a conservative variant thereof; aa8 comprises Lys or a conservative variant thereof; aa9 comprises Gly or a conservative variant thereof; aa10 comprises Pro or a conservative variant thereof; aa11 comprises Nle or a conservative variant thereof, wherein Nle comprises norleucine; aa12 comprises Aib or a conservative variant thereof, wherein Aib comprises α-aminoisobutyric acid; and aa13 comprises paraBrPhe or a conservative variant thereof.

Embodiments disclosed herein relate to apelin peptides, in particular, apelin peptides comprising peptidomimetic of Formula (II): Z2-Lys-Phe-Arg-Arg-Gln-aa'6-aa'7-aa'8-aa'9-aa'10-aa'11-aa'12-aa'13-aa'14-aa'15-aa'16-aa'17, or pharmaceutically acceptable salts thereof, wherein Z2 is H or a long chain moiety, wherein each of aa'6, aa'7, aa'8, aa'9, aa'10, aa'11, aa'12, aa'13, aa'14, aa'15, aa'16 and aa'17 is independently an amino acid, wherein: aa'6 comprises Arg or a conservative variant thereof; aa6 comprises Arg or a conservative variant thereof; aa'7 comprises Pro or a conservative variant thereof; aa'8 comprises an amino acid or a conservative variant thereof selected from the group consisting of Arg, Arg-D, αMeArg and azaArg; aa'9 comprises an amino acid or a conservative variant thereof selected from the group consisting of Leu, NMeLeu, αMeLeu and azaLeu; aa'10 comprises Ser or a conservative variant thereof; aa'11 comprises His or a conservative variant thereof; aa'12 comprises Lys or a conservative variant thereof; aa13 comprises Gly or a conservative variant thereof; aa'14 comprises Pro or a conservative variant thereof; aa'15 comprises Nle or a conservative variant thereof, wherein Nle i comprises norleucine; aa'16 comprises Aib or a conservative variant thereof, wherein Aib comprises α-aminoisobutyric acid; and aa'17 comprises paraBrPhe or a conservative variant thereof.

Embodiments disclosed herein relate to methods of modulating an apelin pathway disorder in a subject comprising administering to the subject a therapeutically effective amount of an apelin peptide comprising a peptidomimetic of Formula (I) of claim 1 or Formula (II) of the present disclosure or pharmaceutically acceptable salts thereof.

Embodiments disclosed herein relate to methods of modulating vascular tone in a subject comprising administering to the subject an effective amount of an apelin receptor agonist comprising a peptidomimetic of Formula (I) or Formula (II), or pharmaceutically acceptable salts thereof.

Embodiments disclosed herein relate to methods of reducing cardiac reperfusion injury following myocardial infarction in a subject comprising administering to the subject an effective amount of an apelin receptor agonist comprising a peptidomimetic of Formula (I) or Formula (II), or pharmaceutically acceptable salts thereof.

Embodiments disclosed herein relate to methods of reducing blood pressure in a subject comprising administering to the subject an effective amount of an apelin receptor agonist comprising a peptidomimetic of Formula (I) or Formula (II), or pharmaceutically acceptable salts thereof.

BRIEF DESCRIPTION OF DRAWINGS

Various embodiments of the present disclosure will be described herein below with reference to the figures wherein:

FIG. 23 shows representative Western blot and averaged quantification for ACE2 in abdominal aorta of Ldlr$^{-/-}$ mice receiving saline, Anq II or Anq II+ apelin peptide 11. Aortic protein from Ace2$^{-/-}$ mouse was used as the negative control.

DETAILED DESCRIPTION

Figure 1:
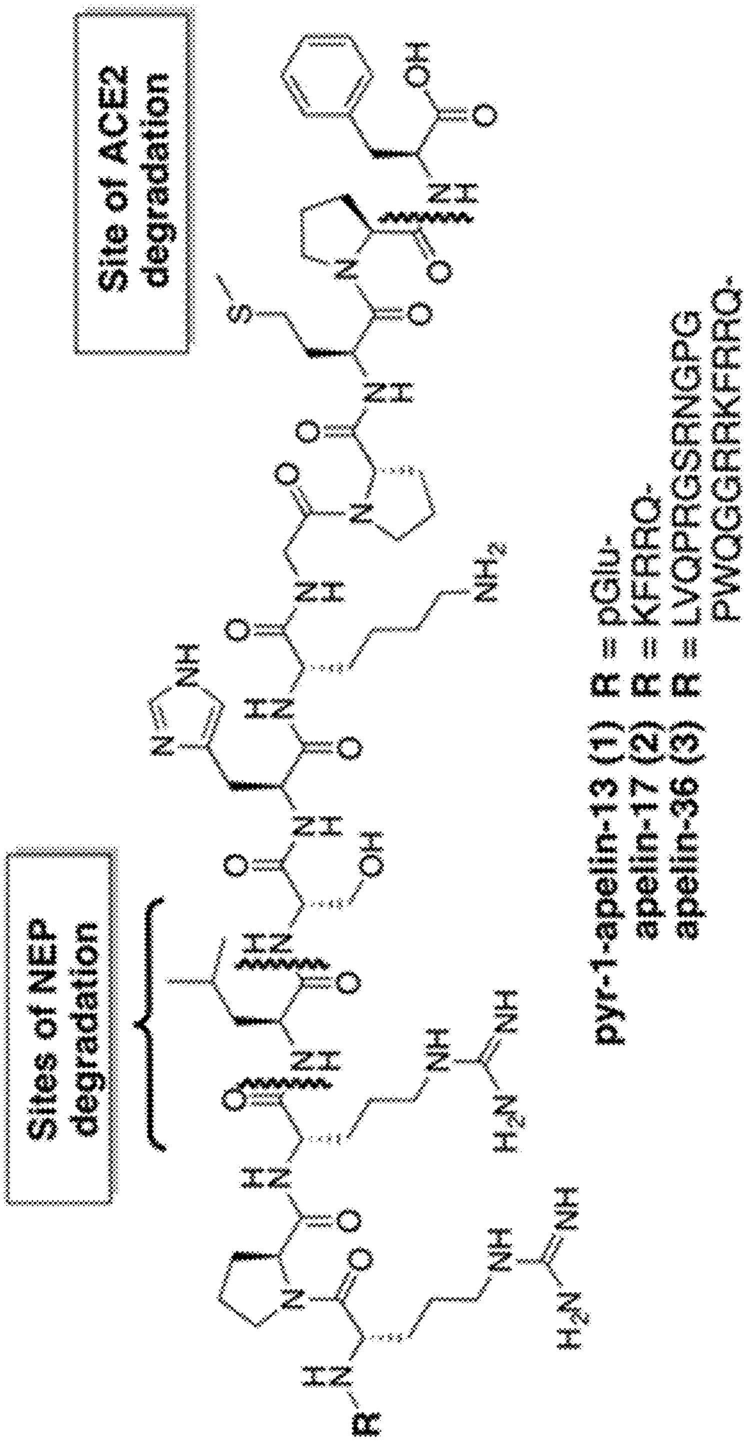
FIG. 1 shows apelin isoforms: (pyr$^1$) apelin-13 fragment (SEQ ID NO:1) (1), apelin-17 (SEQ ID NO:2) (2), and apelin-36 (SEQ ID NO:3) (3), with identified sites of NEP and ACE2 proteolytic degradation.

As used herein, the native human full length 77 amino acid (SEQ ID NO: 6) may be referred to generally as "apelin" or "APLN," while "apelin peptides" will be used in reference to peptides encompassing both naturally occurring cleavage products of apelin such as apelin-36, apelin 17, apelin-13, pyr[1] apelin-13, as well as stabilized synthetic peptide derivatives, in accordance with embodiments herein.

The role of APLN and the therapeutic use of the novel stabilized apelin peptides disclosed herein in myocardial infarction (MI) and ischemia-reperfusion (IR) injury is provided. Myocardial APLN levels were reduced in subjects with ischemic heart failure. Loss of APLN increased MI-related mortality, infarct size, and inflammation with substantial reductions in pro-survival pathways resulting in greater systolic dysfunction and heart failure. APLN deficiency decreased vascular sprouting, impaired sprouting of human endothelial progenitor cells and compromised in vivo myocardial angiogenesis. Lack of APLN enhanced susceptibility to ischemic injury and compromised functional recovery following ex vivo and in vivo IR injury. Advantageously, the stabilized apelin peptides disclosed herein may provide improved apelin proteolytic stability against NEP and improved resistance to angiotensin converting enzyme 2 (ACE2) cleavage and may mimic the function of APLN, while demonstrating protection against ex vivo and in vivo myocardial IR injury linked to greater activation of survival pathways and promotion of angiogenesis. The short half-life of native apelin peptides (Japp A G, et al. *Circulation.* 121:1818-1827, (2010); Vickers C, et al. *J Biol Chem.* 277:14838-14843, (2002); Japp A G, et al. *J Am Coll Cardiol.* 52:908-913, (2008)) prompted the development of the apelin peptides disclosed herein which are more potent and less susceptible to degradation.

Since the APLN system is compromised in human heart failure (Chen M. M., et al. *Circulation.* 108:1432-1439, (2003); Chong K S, et al. *Eur J Heart Fail.* 8:355-360, (2006)), the integrative physiological role of the APLN system indicates that enhancing apelin action may serve to minimize myocardial ischemic damage and the progression to advanced HF (hear failure disease). Enhancing apelin action represents a new approach for the treatment of ischemic heart failure.

As discussed, there exists a need to negate the impact of ACE2 degradation on apelin isoforms, and to improve the overall stability of the apelin isoforms. To negate the impact of ACE2 degradation on apelin isoforms, an ACE2 resistant 'A2' C-terminus may be incorporated into the peptidomimetic of the presence embodiments. The ACE2 resistant 'A2' C-terminus denotes the last three amino acids of the apelin peptides. In some embodiments, the peptidomimetic of the present embodiments comprises unnatural residues substituted at the C-terminal Met-Pro-Phe portion of (pyr[1]) apelin-13 (SEQ ID NO:1). In some embodiments, the peptidomimetic of the present embodiments comprises unnatural residues substituted at the C-terminal Met-Pro-Phe portion of apelin-17. The term "apelin A2 peptides," as used herein, refers to peptides comprise unnatural residues substituted at the C-terminal Met-Pro-Phe.

To further improve the overall stability of the apelin isoforms, it is necessary to stabilize, or to improve the metalloprotease neutral endopeptidase 24.11 (neprilysin, NEP) stability. The inventors of the present disclosure discovered that the NEP has a role in the in vitro proteolysis of apelin. NEP is a significant protease implicated in the degradation and inactivation of vasoactive peptides bradykinin, angiotensins, atrial natriuretic factor (ANP), and endothelins in addition to many other peptide hormones in other organ systems. The site of NEP proteolysis may be structurally and functionally an essential feature for apelin binding and subsequent physiological activity. Without being bound by theory, the amino acid residues surrounding the site of NEP proteolysis (the 'RPRL' motif) has an enhanced rigidity and is suggested to induce a p-turn conformation upon binding (Langelaan, et al. *Biochemistry* 48: 537-548 (2009)), and the two Arg residues have been proposed to form key electrostatic interactions with acidic amino acids on the exterior of the apelin receptor to facilitate ligand binding (Gerbier, R., et al., *FASEB J.:* 29, 314-322 (2015)).

The inventors of the present disclosure discovered a way to improve apelin proteolytic stability against NEP while at the same time negating the impact of ACE2 degradation on apelin isoforms. This approach includes altering the amino acids residues surrounding both the NEP cleavage site and the ACE2 degradation site. FIG. 1 shows apelin isoforms: (pyr[1]) apelin-13 fragment (SEQ ID NO:1) (1), apelin-17 (SEQ ID NO:2) (2), and apelin-36 (SEQ ID NO:3) (3), with identified sites of NEP and ACE2 proteolytic degradation. In certain embodiments, the disclosure provides peptidomimetic comprises unnatural residues substituted at the C-terminal Met-Pro-Phe portion. In certain embodiments, the disclosure provides peptidomimetic comprises unnatural residues substituted at the C-terminal Met-Pro-Phe portion and optionally at any one or more of amino acids at the "RPRL" motif (e.g., amino acid 2 "aa2", amino acid 3 "aa3", amino acid 4 "aa4", and/or amino acid 5 "aa5") of (pyr[1]) apelin-13. In certain embodiments, apelin peptides comprising peptidomimetic of Formula (I), wherein Z1 is H, having the following formula: pGlu-aa2-aa3-aa4-aa5-aa6-aa7-aa8-aa9-aa10-aa11-aa12-aa13, or pharmaceutically acceptable salts thereof, wherein aa2 to aa13 are defined herein. pGlu refers to pyroglutamic acid.

In certain embodiments, the disclosure provides peptidomimetic comprises unnatural residues substituted at the C-terminal Met-Pro-Phe portion and optionally at any one or more of amino acids at the RPRL motif (e.g., amino acid 6 "aa'6", amino acid 7 "aa'7", amino acid 8 "aa'8", and/or amino acid 9 "aa'9") of apelin-17. In certain embodiments, the disclosure provides apelin peptides comprising peptidomimetic of Formula (II), wherein Z2 is H, having the following formula: Lys-Phe-Arg-Arg-Gln-aa'6-aa'7-aa'8-aa'9-aa'10-aa'11-aa'12-aa'13-aa'14-aa'15-aa'16-aa'17, or pharmaceutically acceptable salts thereof, wherein aa'9 to aa'20 are defined herein.

Figure 12:
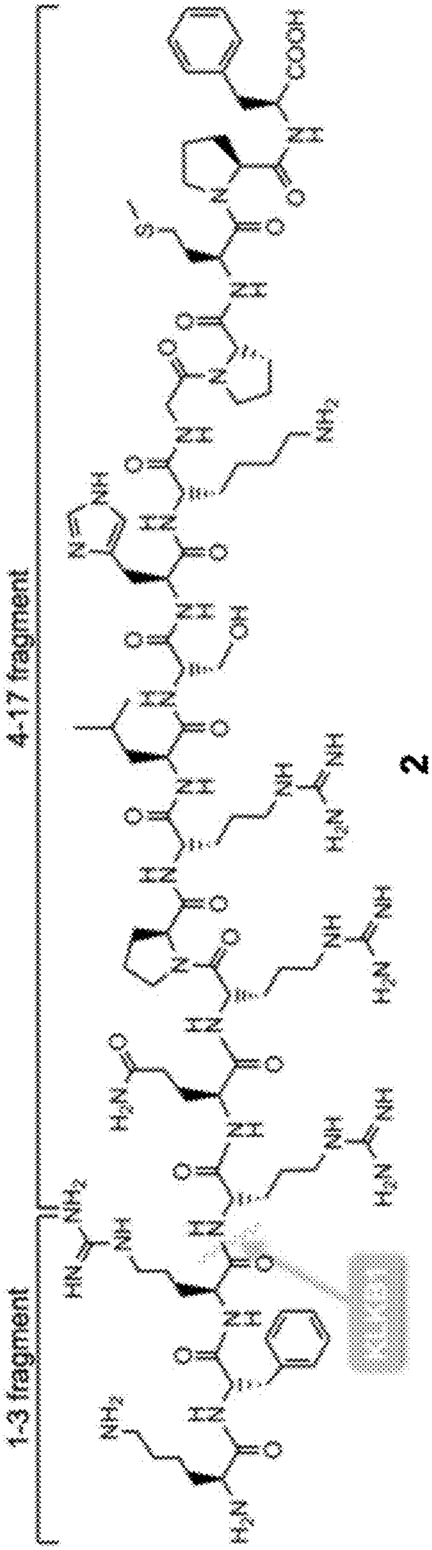
FIG. 12 shows the KLKB1 cleavage between Arg3 and Arg4 of the native Apelin-17 (2).

The inventors of the present disclosure further discovered that the human plasma kallikrein (KLKB1) also has a role in the in vitro proteolysis of apelin. The inventors discovered that KLKB1 cleaves after the first three N-terminal amino acids (KFR) of the apelin-17 (i.e., cleavage between Arg3-Arg4). The KLKB1 cleavage produces the C-terminal 14-mer lacking the polar basic KFR head group. FIG. 12 shows the KLKB1 cleavage between Arg3 and Arg4 of the native Apelin-17 (2).

In the human body, KLKB1 circulates as zymogen bound to high-molecular-weight kininogen and is activated by coagulation factor XIIa. (Kaplan, et. al.; Bradykinin formation. Plasma and tissue pathways and cellular interactions. *Clin. Rev. Allergy Immunol.* 1998, 16, 403-429.). Once activated, KLKB1 possesses a trypsin like activity, cleaving at a basic residue in P1 position (Arg), whereas the bulky hydrophobic Phe side chain at P2 can be accommodated in the S2 pocket of this enzyme. (Tang, et. al.; Expression, crystallization, and three-dimensional structure of the catalytic domain of human plasma kallikrein. *J. Biol. Chem.* 2005, 280, 41077-41089.).

To improve apelin in vivo half-life, the inventors of the present disclosure discovered that this can be accomplished by the attachment of a long chain moiety to the N-terminus of the apelin A2 peptides. Examples of long chain moieties and techniques to increase plasma half-life include, but are not limited to, N-terminal fatty acid chain (PALMitoylation), and polyethylene glycol chain (PEGylation), XTEN (an 83.5 kDa) recombinant polypeptide consisting only of the amino acids Ala, Asp, Gly Pro, Ser, and Thr, detran conjugation, HESylation (Hydroxyethyl Starch, HES, is a modified natural polymer obtained by controlled hydroxyethylation of the plant polysaccharide amylopectin), polysialylation, HAylation, N- and O-Glycosylation, and lipidation, all of which are disclosed in Witteloostuijn, et. al., "Half-life extension of biopharmaceuticals using chemical methods: alternatives to PEGylation;" ChemMedChem 2016, 11, 2474-2495, the disclosure of which is incorporated herein by reference in its entirety.

In certain embodiments, the disclosure provides apelin peptides comprising peptidomimetic of Formula (I) having the following formula: Z1-pGlu-aa2-aa3-aa4-aa5-aa6-aa7-aa8-aa9-aa10-aa11-aa12-aa13, or pharmaceutically acceptable salts thereof, wherein Z1 is a long chain moiety, wherein aa2 to aa13 are defined herein. In some embodiments, Z1 is PALM or PEG.

In certain embodiments, the disclosure provides apelin peptides comprising peptidomimetic of Formula (II) having the following formula: Z2-Lys-Phe-Arg-Arg-Gln-aa'6-aa'7-aa'8-aa'9-aa'10-aa'11-aa'12-aa'13-aa'14-aa'15-aa'16-aa'17, or pharmaceutically acceptable salts thereof, wherein Z2 is a long chain moiety, wherein aa'6 to aa'17 are defined herein. In some embodiments, Z2 is PALM or PEG.

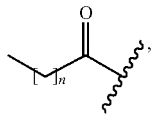

In some embodiments, PALM may be wherein n is from 8 to 20, from 10 to 18, or from 12 to 16. In some embodiments, any one or more carbon atom of the PALM may be independently optionally substituted with a lower alkyl (e.g., methyl, ethyl, or propyl), PEG may be linear or branched and the end groups may be either a hydroxyl group, amino group, a methoxy group, or a protecting group, such as, Fmoc (fluorenylmethyloxycarbonyl), Boc (tert-butyloxycarbonyl), and the like.

In some embodiments, PEG is

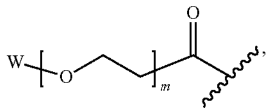

wherein m is from 3 to 10, from 4 to 8, or from 5 to 7, wherein W may be H, a lower alkyl (e.g., methyl, ethyl, propyl, etc.), or a protecting group. In some embodiments, PEG is Fmoc-NH$(CH_2)_p$—, wherein p is 1 to 5, or 2 to 4. In a specific embodiment, PEG is

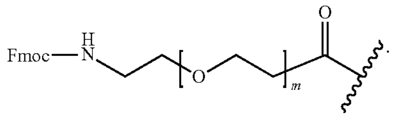

Both the PEG and PALM groups are attached to the apelin peptide via an amide bond through the N-terminus. By way of example, the following illustrates that the PALM group attaches to the N-terminus amino acid through an amide bond:

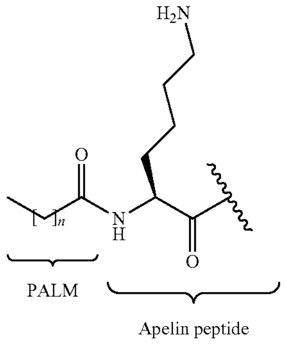

In specific embodiments, the disclosure provides specific apelin peptides having the following structures:

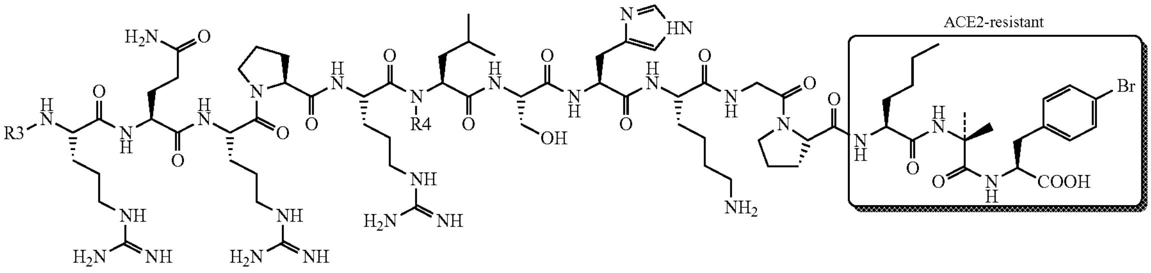

| Compound No. | R3 | R4 |
|---|---|---|
| 5 | $NH_2$-Lys-Phe-Arg | H |
| 11 | $NH_2$-Lys-Phe-Arg | $CH_3$ |
| 54 | H | H |

-continued

| | | |
|---|---|---|
| 55 | H | $CH_3$ |
| 56 | PALM-Lys-Phe-Arg | H |
| 57 | PEG-Lys-Phe-Arg | H |
| 58 | PALM-Lys-Phe-Arg | $CH_3$ |
| 59 | PEG-Lys-Phe-Arg | $CH_3$ |

PALM =

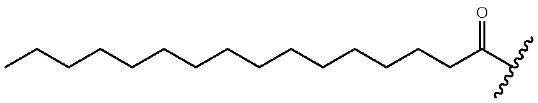

PEG =

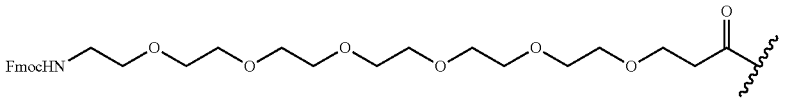

In some embodiments, the disclosure provides apelin peptide (54):

(SEQ ID NO: 35)
Arg-Gln-Arg-Pro-Arg-Leu-Ser-His-Lys-Gly-Pro-Nle-Aib-paraBrPhe.

In some embodiments, the disclosure provides apelin peptide (55):

(SEQ ID NO: 36)
Arg-Gln-Arg-Pro-Arg-NMeLeu-Ser-His-Lys-Gly-Pro-Nle-Aib-paraBrPhe.

In some embodiments, the disclosure provides apelin peptide (56):

(SEQ ID NO: 37)
PALM-Lys-Phe-Arg-Arg-Gln-Arg-Pro-Arg-Leu-Ser-His-Lys-Gly-Pro-Nle-Aib-paraBrPhe.

In some embodiments, the disclosure provides apelin peptide (57):

(SEQ ID NO: 38)
PEG-Lys-Phe-Arg-Arg-Gln-Arg-Pro-Arg-Leu-Ser-His-Lys-Gly-Pro-Nle-Aib-paraBrPhe.

In some embodiments, the disclosure provides apelin peptide (58):

(SEQ ID NO: 39)
PALM-Lys-Phe-Arg-Arg-Gln-Arg-Pro-Arg-NMeLeu-Ser-His-Lys-Gly-Pro-Nle-Aib-paraBrPhe.

In some embodiments, the disclosure provides apelin peptide (59):

(SEQ ID NO: 40)
PEG-Lys-Phe-Arg-Arg-Gln-Arg-Pro-Arg-NMeLeu-Ser-His-Lys-Gly-Pro-Nle-Aib-paraBrPhe.

In some embodiments, the disclosure provides apelin peptide:

(SEQ ID NO: 41)
PALM-Lys-Phe-Arg-Arg-Gln-Arg-Pro-Arg-D-Leu-Ser-His-Lys-Gly-Pro-Nle-Aib-paraBrPhe.

In some embodiments, the disclosure provides apelin peptide:

(SEQ ID NO: 42)
PALM-Lys-Phe-Arg-Arg-Gln-Arg-Pro-αMeArg-Leu-Ser-His-Lys-Gly-Pro-Nle-Aib-paraBrPhe.

In some embodiments, the disclosure provides apelin peptide:

(SEQ ID NO: 43)
PALM-Lys-Phe-Arg-Arg-Gln-Arg-Pro-Arg-αMeLeu-Ser-His-Lys-Gly-Pro-Nle-Aib-paraBrPhe.

In some embodiments, the disclosure provides apelin peptide:

(SEQ ID NO: 44)
PALM-Lys-Phe-Arg-Arg-Gln-Arg-Pro-azaArg-Leu-Ser-His-Lys-Gly-Pro-Nle-Aib-paraBrPhe.

In some embodiments, the disclosure provides apelin peptide:

(SEQ ID NO: 45)
PALM-Lys-Phe-Arg-Arg-Gln-Arg-Pro-Arg-azaLeu-Ser-His-Lys-Gly-Pro-Nle-Aib-paraBrPhe.

In some embodiments, the disclosure provides apelin peptide:

(SEQ ID NO: 46)
PEG-Lys-Phe-Arg-Arg-Gln-Arg-Pro-Arg-D-Leu-Ser-His-Lys-Gly-Pro-Nle-Aib-paraBrPhe.

In some embodiments, the disclosure provides apelin peptide:

(SEQ ID NO: 47)
PEG-Lys-Phe-Arg-Arg-Gln-Arg-Pro-αMeArg-Leu-Ser-His-Lys-Gly-Pro-Nle-Aib-paraBrPhe.

In some embodiments, the disclosure provides apelin peptide:

(SEQ ID NO: 48)
PEG-Lys-Phe-Arg-Arg-Gln-Arg-Pro-Arg-αMeLeu-Ser-His-Lys-Gly-Pro-Nle-Aib-paraBrPhe.

In some embodiments, the disclosure provides apelin peptide:

(SEQ ID NO: 49)
PEG-Lys-Phe-Arg-Arg-Gln-Arg-Pro-azaArg-Leu-Ser-His-Lys-Gly-Pro-Nle-Aib-paraBrPhe.

In some embodiments, the disclosure provides apelin peptide:

(SEQ ID NO: 50)
PEG-Lys-Phe-Arg-Arg-Gln-Arg-Pro-Arg-azaLeu-Ser-His-Lys-Gly-Pro-Nle-Aib-paraBrPhe.

The term "peptidomimetic," as used herein, refers to a peptide-like molecule that has the activity of the peptide upon which it is structurally based. A peptidomimetic includes the substitution of one or more naturally occurring amino acids for any chemically modified amino acids, individual unnatural amino acids, peptide-like molecules containing non-naturally occurring amino acids, and peptoids, and have an activity of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons (1995), pages 803-861).

The term "amino acid," as used herein, refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, selenocysteine, pyrrolysine, and O-phosphoserine. "Amino acid analogs" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The number after "amino acid" or "aa' or aa'" denotes the position of the amino acid residue in the polypeptide chain when counted from the amino terminal.

The terms "compounds," "peptides," and "peptidomimetic" are used interchangeably in the disclosure.

In some of such embodiments, the peptidomimetics may be selected to provide non-hydrolyzable residues at these positions. Non-natural peptidomimetic residues may include, without limitation, D-amino acids, beta amino acids, homo amino acids, proline derivatives, para-substituted phenylalanines, amino alcohols, N-substituted amides, bridging amides, quaternary alpha amino acids, N-alkyl amino acids, alpha-alkyl amino acids, and aza peptides. D-amino acids involve the mirror image of the naturally occurring L-isomers, which are mostly to increase resistance against a range of degradation enzymes. Homo amino acids include the addition of a methylene ($CH_2$) group to the α-carbon of an amino acid, which are used to creating peptides that may have altered biological characteristics, such as enhanced biological activity or better biological stability. N-alkyl amino acids are amino acids that carry an alkyl group at the nitrogen instead of a proton. Introducing an N-alkyl amino acid (exemplified by methylation) may create a sterically hindered environment about a susceptible amide bond, which may increase the enzymatic stability of a peptide, thus increasing its biological half-life. Substitution with N-alkyl amino acids may also improve peptidase stability and enhance intestinal permeability. Alpha-alkyl amino acids are amino acids in which the proton on the α-carbon atom of the natural original (in between the amino and carboxy group) has been substituted by an alkyl group. Alpha-methyl amino acids are stable to racemization/epimerization since there is no longer the possibility for abstracting the α-proton. Bridging amide and aza peptide are strategies for stabilizing amide bonds.

In certain embodiments, peptidomimetics disclosed herein may modify any amino acid residues about an amide bond according to the following chemical structural modifications to enhance stability against enzymatic (or non-enzymatic) hydrolytic activity as indicated in Scheme I. One skilled in the art will appreciate that any of these techniques may be used in combination and that any other amide stabilizing strategies may be employed. $R_1$ and $R_2$ shown in Scheme I denote the side chains of the amino acids according to the present embodiments. Scheme I illustrates the modification by substituting H with a methyl group. However, one skilled in the art will appreciate that the use of methyl functional groups in Scheme I is merely exemplary and that other functional chemical moieties may fulfill substantially the same role.

Scheme 1

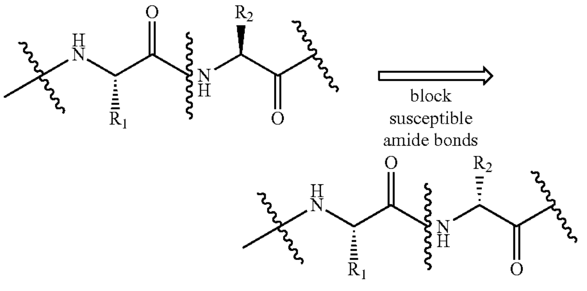

D-amino acid

-continued

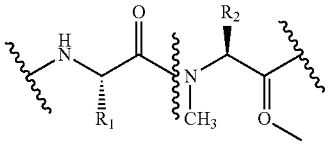

N-methyl amino acid

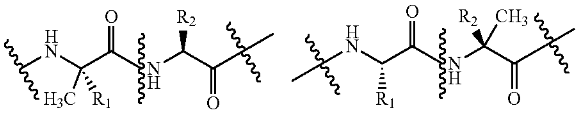

α-methyl amino acid

-continued

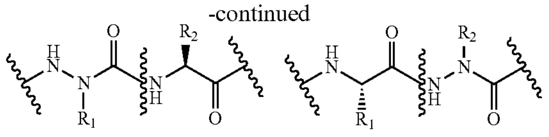

aza peptide

By way of example only, a peptidomimetic of pyr-1-apelin-13 A2 peptide having the formula: pGlu-aa2-aa3-aa4-aa5-Ser-His-Lys-Gly-Pro-Nle-Aib-paraBrPhe (SEQ ID NO:52), a peptidomimetic of apelin-17 A2 peptide having the formula: Lys-Phe-Arg-Arg-Gln-aa'6-aa'7-aa'8-aa'9-Ser-His-Lys-Gly-Pro-Nle-Aib-paraBrPhe (SEQ ID NO:53), and a peptidomimetic of N-terminus modified apelin-17 A2 peptide having the formula: Z2-Lys-Phe-Arg-Arg-Gln-aa'6-aa'7-aa'8-aa'9-Ser-His-Lys-Gly-Pro-Nle-Aib-paraBrPhe (SEQ ID NO:54) are shown below identifying the ACE2 resistant 'A2' C-terminus Nle11, Aib12, and para-BrPhe13 amino acid substitutions and Nle15, Aib16, and para-Br-Phe17 amino acid substitutions respectively.

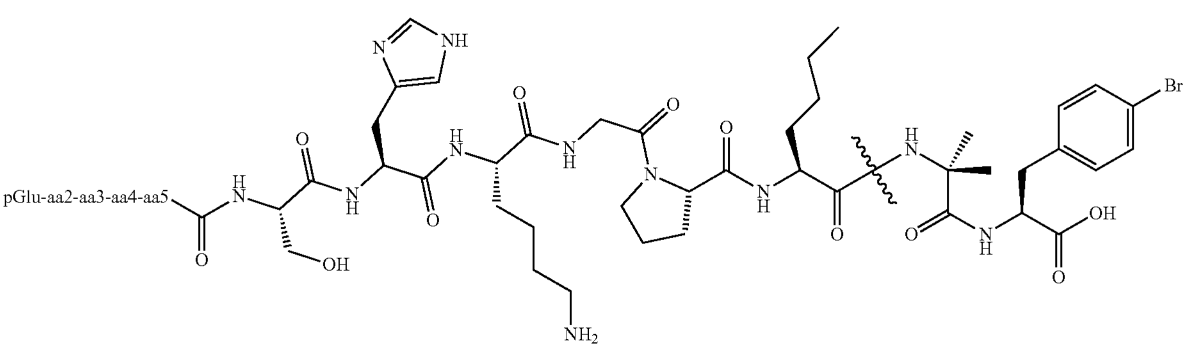

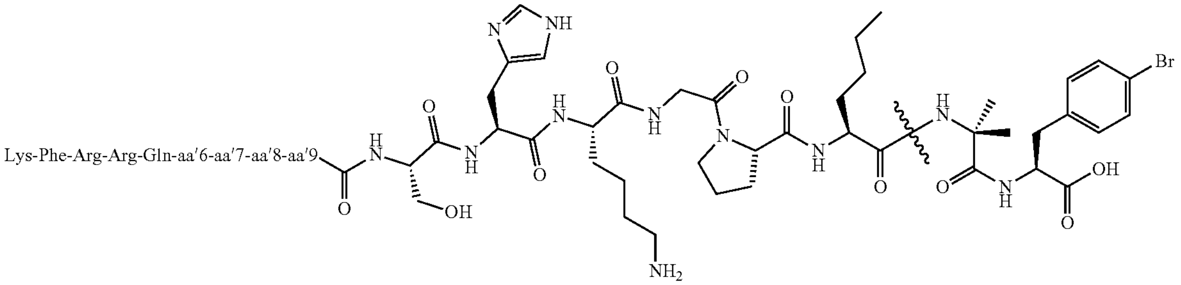

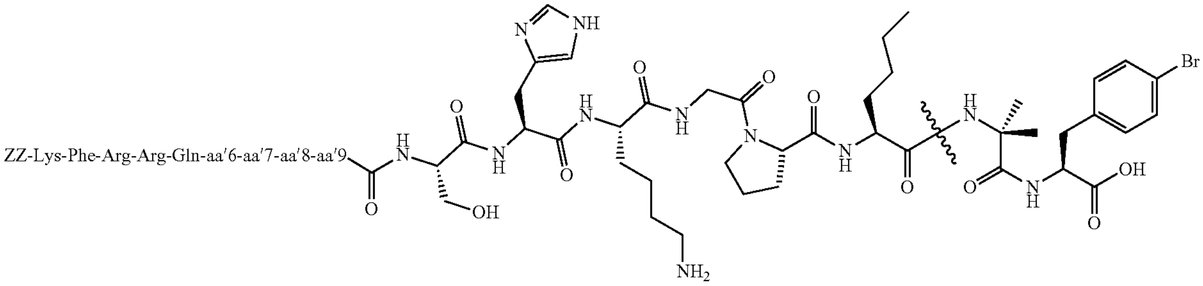

where Z2 is a long chain moiety as defined herein.

In some embodiments, the pyr-1-apelin-13 A2 peptide (SEQ ID NO: 4) includes substitution of native methionine for norleucine at amino acid 11 (aa11). In some embodiments, the apelin-17 A2 peptide (SEQ ID NO: 5) includes substitution of native methionine for norleucine at amino acid 15 (aa'15). Without being bound by theory, the inventors believe that the native methionine residue is susceptible to oxidation. Thus, replacement with a simple hydrophobic residue may serve to circumvent this oxidative problem. One skilled in the art will appreciate that substantially similar residues can replace norleucine by conservative substitution to provide an apelin peptide with substantially similar enhancement in stability. For example, other residues that may function in a manner similar to norleucine may include alanine, homoalanine, valine, leucine, and isoleucine.

Similarly, the inventors believe that a modest electron withdrawing group on C-terminal Phe may enhance apelin stability and/or activity. Thus, the bromo on Phe may be replaced with other electron withdrawing groups to similar effect. Such groups may include, without limitation, chloro, nitro, ester, and the like. In certain embodiments, the electron withdrawing group need not appear in the para position, although from a synthetic standpoint this may be one of the easier positions to modify. In some embodiments, the pyr-1-apelin-13 A2 peptide (SEQ ID NO: 4) includes substitution of native phenylanlanine for bromophenylanlanine, BrPhe (e.g., orth-BrPhe, meta-BrPhe, para-BrPhe) at amino acid 13 (aa13). In some embodiments, the apelin-17 A2 peptide (SEQ ID NO: 5) includes substitution of native phenylanlanine for bromophenylanlanine, BrPhe (e.g., orth-BrPhe, meta-BrPhe, para-BrPhe) at amino acid 17 (aa'17).

In some embodiments, the pyr-1-apelin-13 A2 peptide (SEQ ID NO: 4) includes substitution of native proline for aminoisobutyryl (Aib) at amino acid 12 (aa12). In some embodiments, the apelin-17 A2 peptide (SEQ ID NO: 5) includes substitution of native proline for aminoisobutyryl (Aib) at amino acid 16 (aa'16). The sterically hindered aminoisobutyryl (Aib) residue present in the apelin peptides may slow C-terminal hydrolytic processes. Other hindered alpha amino acids may achieve nominally the same effect. Thus, for example, any alpha, alpha-dialkylamino acid may be employed for this purpose. The preparation and coupling of hindered amino acids has been described in Fu et al. *J. Org. Chem.* 66(21):7118-24 (2001), which is incorporated herein by reference in its entirety.

In similar embodiments, such substitutions as described above may be introduced into apelin-36 or even in the native full apelin protein having 77 amino acid residues. Those skilled in the art will appreciate that with the full length apelin protein, non-linear synthetic strategies for protein preparation may be advantageous. Such proteins may also be achieved by incorporation of unnatural amino acids by engineering the requisite tRNA for its incorporation in a biosynthesis approach. Such methods are well known to those skilled in the art.

In some embodiments, apelin peptides comprising serine may be stabilized against the activity of serine proteases. In some such embodiments, the serine residue may be replaced with homoalanine, for example. Other conservative substitutions for serine may be employed including any neutral alkyl substituted amino acids such as alanine, leucine, or isoleucine. Other modifications may include the blocking of the serine hydroxyl group, such as by formation of a methyl ether.

Thus, N-alkylation (exemplified by methylation), C-quaternization (also exemplified by methylation) or both may be employed to create a sterically hindered environment at a susceptible amide bond. Also shown are bridging amide and aza peptide strategies for stabilizing amide bonds. One skilled in the art will appreciate that any of these techniques may be used in combination and that any other amide stabilizing strategies may be employed.

In some embodiments, the peptidomimetic contains an ACE2 resistant 'A2' C-terminus Nle, Aib, and para-BrPhe amino acid substitutions.

Figure 2:
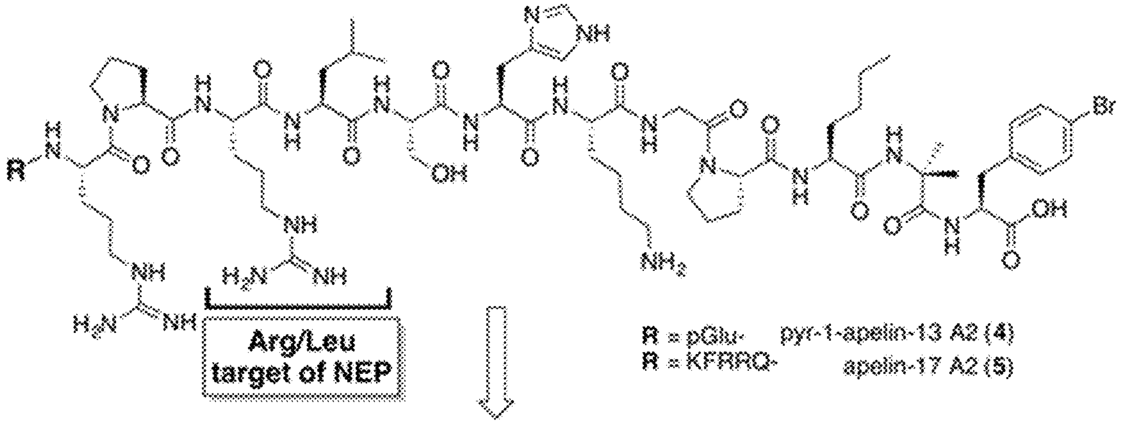
FIG. 2 illustrates certain syntheric modifications into both the pyr-1-apelin-13 A2, pGlu-Arg-Pro-Arg-Leu-Ser-His-Lys-Gly-Pro-Nle-Aib-paraBrPhe (SEQ ID NO:4) (4), and apelin-17 A2, Lys-Phe-Arg-Arg-Gln-Arg-Pro-Arg-Leu-Ser-His-Lys-Gly-Pro-Nle-Aib-paraBrPhe (SEQ ID NO:5) (5), in accordance with embodiments of the present disclosure.
Figure 2:
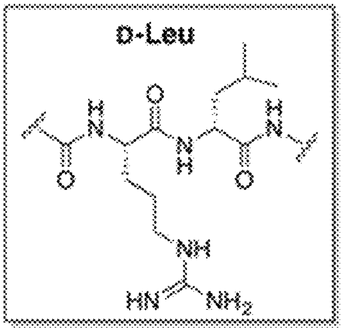
Figure 2:
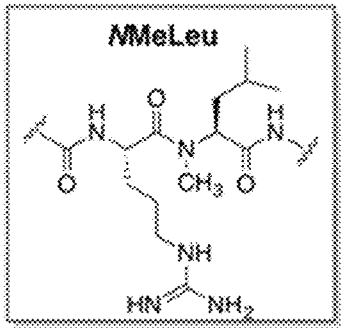
Figure 2:
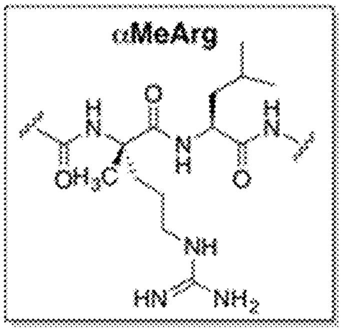
Figure 2:
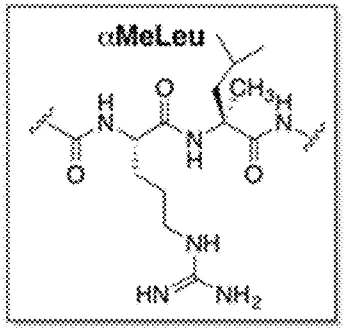
Figure 2:
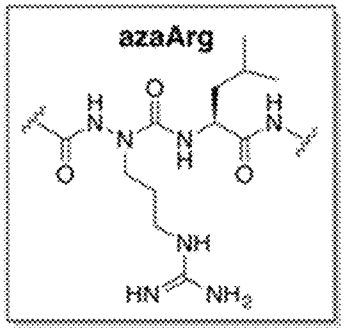
Figure 2:
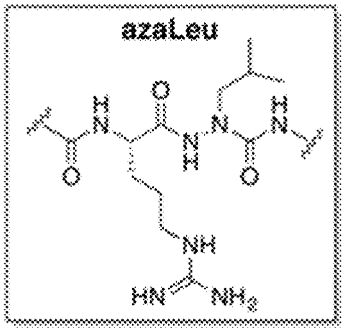

In embodiments, the present disclosure provides peptidomimetic with enhanced stability to NEP based on the apelin 'A2' peptides of (pyr1) apelin-13 A2 (SEQ ID NO:4)(4) and apelin-17 A2 (SEQ ID NO:5)(5). FIG. 2 illustrates certain syntheric modifications of both the pyr-1-apelin-13 A2 (SEQ ID NO:4) (4) and apelin-17 A2 (SEQ ID NO:5) (5), in accordance with embodiments of the present disclosure. The modifications include replacing the dipeptide Arg/Leu with various dipeptides as shown in FIG. 2 to produce apelin peptides (8)-(19).

In some embodiments, the disclosure provides apelin peptide (8):

(SEQ ID NO: 24)
pGlu-Arg-Pro-Arg-D-Leu-Ser-His-Lys-Gly-Pro-Nle-Aib-paraBrPhe.

In some embodiments, the disclosure provides apelin peptide (9):

(SEQ ID NO: 25)
Lys-Phe-Arg-Arg-Gln-Arg-Pro-Arg-D-Leu-Ser-His-Lys-Gly-Pro-Nle-Aib-paraBrPhe.

In some embodiments, the disclosure provides apelin peptide (10):

(SEQ ID NO: 26)
pGlu-Arg-Pro-Arg-NMeLeu-Ser-His-Lys-Gly-Pro-Nle-Aib-paraBrPhe.

In some embodiments, the disclosure provides apelin peptide (11):

(SEQ ID NO: 27)
Lys-Phe-Arg-Arg-Gln-Arg-Pro-Arg-NMeLeu-Ser-His-Lys-Gly-Pro-Nle-Aib-paraBrPhe.

In some embodiments, the disclosure provides apelin peptide (12):

(SEQ ID NO: 28)
pGlu-Arg-Pro-αMeArg-Leu-Ser-His-Lys-Gly-Pro-Nle-Aib-paraBrPhe.

In some embodiments, the disclosure provides apelin peptide (13):

(SEQ ID NO: 29)
Lys-Phe-Arg-Arg-Gln-Arg-Pro-αMeArg-Leu-Ser-His-Lys-Gly-Pro-Nle-Aib-paraBrPhe.

In some embodiments, the disclosure provides apelin peptide (14):

(SEQ ID NO: 30)
pGlu-Arg-Pro-Arg-αMeLeu-Ser-His-Lys-Gly-Pro-Nle-Aib-paraBrPhe.

In some embodiments, the disclosure provides apelin peptide (15):

(SEQ ID NO: 31)
Lys-Phe-Arg-Arg-Gln-Arg-Pro-Arg-αMeLeu-Ser-His-Lys-Gly-Pro-Nle-Aib-paraBrPhe.

In some embodiments, the disclosure provides apelin peptide (16):

(SEQ ID NO: 51)
pGlu-Arg-Pro-azaArg-Leu-Ser-His-Lys-Gly-Pro-Nle-Aib-paraBrPhe.

In some embodiments, the disclosure provides apelin peptide (17):

(SEQ ID NO: 32)
Lys-Phe-Arg-Arg-Gln-Arg-Pro-azaArg-Leu-Ser-His-Lys-Gly-Pro-Nle-Aib-paraBrPhe.

In some embodiments, the disclosure provides apelin peptide (18):

(SEQ ID NO: 33)
pGlu-Arg-Pro-Arg-azaLeu-Ser-His-Lys-Gly-Pro-Nle-Aib-paraBrPhe.

In some embodiments, the disclosure provides apelin peptide (19):

(SEQ ID NO: 34)
Lys-Phe-Arg-Arg-Gln-Arg-Pro-Arg-azaLeu-Ser-His-Lys-Gly-Pro-Nle-Aib-paraBrPhe.

In some embodiments, synthetic modifications may be made at any one or more amino acids of the "RPRL" motif portion of the apelin 'A2' peptides. In some embodiments, synthetic modifications may be made at any one or more amino acid 2, amino acid 3, amino acid 4, and/or amino acid 5 (aa2, aa3, aa4 and/or aa5) of the pyr-1-apelin-13 A2 peptide (SEQ ID NO: 4). In some embodiments, synthetic modifications may be made at any one or more amino acid 6, amino acid 7, amino acid 8, and/or amino acid 9 (aa'6, aa'7, aa'8 and/or aa'9) of the apelin-17 A2 peptide (SEQ ID NO: 5).

In embodiments, the peptidomimetic of Formula (I): Z1-pGlu-aa2-aa3-aa4-aa5-aa6-aa7-aa8-aa9-aa10-aa11-aa12-aa13, or pharmaceutically acceptable salts thereof, wherein Z1 is defined herein, wherein the sequence aa2-aa3-aa4-aa5-aa6-aa7-aa8-aa9-aa10-aa11-aa12-aa13 is any one of the sequences listed in Table 1.

In embodiments, the peptidomimetic of Formula (II): Z2-Lys-Phe-Arg-Arg-Gln-aa'6-aa'7-aa'8-aa'9-aa'10-aa'11-aa'12-aa'13-aa'14-aa'15-aa'16-aa'17, or pharmaceutically acceptable salts thereof, wherein Z2 is defined herein, wherein the sequence aa'6-aa'7-aa'8-aa'9-aa'10-aa'11-aa'12-aa'13-aa'14-aa'15-aa'16-aa'17 is any one of the sequences listed in Table 1.

TABLE 1

| |
|---|
| Arg-Pro-Arg-D-Leu-Ser-His-Lys-Gly-Pro-Nle-Aib-paraBrPhe (Seq ID NO: 12) |
| Arg-Pro-Arg-NMeLeu-Ser-His-Lys-Gly-Pro-Nle-Aib-paraBrPhe (Seq ID NO: 13) |
| Arg-Pro-αMeArg-Leu-Ser-His-Lys-Gly-Pro-Nle-Aib-paraBrPhe (Seq ID NO: 14) |
| Arg-Pro-Arg-αMeLeu-Ser-His-Lys-Gly-Pro-Nle-Aib-paraBrPhe (Seq ID NO: 15) |
| Arg-Pro-azaArg-Leu-Ser-His-Lys-Gly-Pro-Nle-Aib-paraBrPhe (Seq ID NO: 16) |
| Arg-Pro-Arg-azaLeu-Ser-His-Lys-Gly-Pro-Nle-Aib-paraBrPhe (Seq ID NO: 17) |

In embodiments, the peptidomimetic of Formula (I): Z1-pGlu-aa2-aa3-aa4-aa5-aa6-aa7-aa8-aa9-aa10-aa11-aa12-aa13, or pharmaceutically acceptable salts thereof, wherein Z1 is defined herein, wherein the sequence aa2-aa3-aa4-aa5-aa6-aa7-aa8-aa9-aa10 is any one of the sequences listed in Table 2.

In embodiments, the peptidomimetic of Formula (II): Z2-Lys-Phe-Arg-Arg-Gln-aa'6-aa7-aa'8-aa'9-aa'10-aa'11-aa'12-aa'13-aa'14-aa'15-aa'16-aa'17, or pharmaceutically acceptable salts thereof, wherein Z2 is defined herein, wherein Z2 is defined herein, wherein the sequence aa'6-aa'7-aa'8-aa'9-aa10-aa'11-aa'12-aa'13-aa'14 is any one of the sequences listed in Table 2.

TABLE 2

| |
|---|
| Arg-Pro-Arg-D-Leu-Ser-His-Lys-Gly-Pro (Seq ID NO: 18) |
| Arg-Pro-Arg-NMeLeu-Ser-His-Lys-Gly-Pro (Seq ID NO: 19) |
| Arg-Pro-αMeArg-Leu-Ser-His-Lys-Gly-Pro (Seq ID NO: 20) |
| Arg-Pro-Arg-αMeLeu-Ser-His-Lys-Gly-Pro (Seq ID NO: 21) |
| Arg-Pro-azaArg-Leu-Ser-His-Lys-Gly-Pro (Seq ID NO: 22) |
| Arg-Pro-Arg-azaLeu-Ser-His-Lys-Gly-Pro (Seq ID NO: 23) |

In embodiments, the peptidomimetic disclosed herein comprises a suitable sequence having at least 80%, at least 85%, at least 90% or at least 95% identical to any one of the sequences disclosed in Table 1 or 2. In embodiments, the peptidomimetic disclosed herein comprises a suitable sequence having at least 80%, at least 85%, at least 90% or at least 95% to any one of the sequences disclosed in Table 1 or 2, wherein a desired function of the peptidomimetic is conserved or retained.

The term "percent identical" refers to sequence identity between two amino acid sequences. Identity can be determined by comparing a position in each sequence which may be aligned for purposes of comparison. When an equivalent position in the compared sequences is occupied by the same amino acid, then the molecules are identical at that position. When the equivalent site is occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used to determine percent identity or percent homology, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or mismatch between the two sequences.

Conservative variation of amino acid residues entails the replacement of one amino acid for another with like characteristics, or biologically similar residue. For a detailed description of protein chemistry and structure, see Schulz, G. E. et al., Principles of Protein Structure, Springer-Verlag, New York, 1979, and Creighton, T. E., Proteins: Structure and Molecular Principles, W. H. Freeman & Co., San Francisco, 1984, which are hereby incorporated by reference. The types of substitutions which may be made in the apelin peptides which are conservative substitutions are exemplified by exchanges within one of the following groups: 1. Small aliphatic, nonpolar or slightly polar residues: e.g., Ala, Ser, Thr, Gly; 2. Polar, negatively charged residues and their amides: e.g., Asp, Asn, Glu, Gln; and 3. Polar, positively charged residues: e.g., His, Arg, Lys. 4. Hydrophobic residues: e.g., Ile, Val, Leu, Met. For example, the replacement of a polar residue for another, such as the substitution of arginine for lysine, glutamic for aspartic acids, or glutamine for asparagine; the replacement of a hydrophobic residue such as isoleucine, valine, leucine or methionine for another, and the like. In a particular sequence, e.g., aa2-aa3-aa4-aa5, a conservative variation means any one of more of the amino acids within the sequence can be replaced. As used herein "variant" and grammatical variations thereof, refers to a protein or peptide that deviates from a reference protein or peptide sequence. Modified and variant proteins or peptides may therefore have greater or less activity or function than a reference protein or peptide but at least retain partial activity or function of the reference protein or peptide.

Most substitutions which are conservative are those which do not produce substantial changes in the characteristics of the apelin peptide, although some changes disclosed herein are purposely designed to confer prolonged peptide stability in vitro and/or in vivo as explained herein. Even when it is difficult to predict the exact effect of a substitution in advance of doing so, one skilled in the art will appreciate that the effect can be evaluated by routine screening assays, including the biological assays described herein. Modifications of apelin peptide properties including redox or thermal stability, hydrophobicity, susceptibility to proteolytic degradation or the tendency to aggregate with carriers or into multimers may be assayed by methods well known to the ordinarily skilled artisan.

In some embodiments, the positions at amino acid 2 (aa2) and amino acid 3 (aa3) of Formula (I) is Arg-Pro. In embodiments, the positions at amino acid 4 (aa4) and amino acid 5 (aa5) of Formula (I) is Arg-D-Leu. In embodiments, the positions at amino acid 4 (aa4) and amino acid 5 (aa5) of Formula (I) is Arg-NMeLeu. In embodiments, the positions at amino acid 4 (aa4) and amino acid 5 (aa5) of Formula (I) is αMeArg-Leu. In embodiments, the positions at amino acid 4 (aa4) and amino acid 5 (aa5) of Formula (I) is Arg-αMeLeu. In embodiments, the positions at amino acid 4 (aa4) and amino acid 5 (aa5) of Formula (I) is azaArg-Leu. In embodiments, the positions at amino acid 4 (aa4) and amino acid 5 (aa5) of Formula (I) is Arg-azaLeu.

In some embodiments, the positions at amino acid 6 (aa'6) and amino acid 7 (aa'7) of Formula (II) is Arg-Pro. In embodiments, the positions at amino acid 8 (aa'8) and amino acid 9 (aa'9) of Formula (II) is Arg-D-Leu. In embodiments, the positions at amino acid 8 (aa'8) and amino acid 9 (aa'9) of Formula (II) is Arg-NMeLeu. In embodiments, the positions at amino acid 8 (aa'8) and amino acid 9 (aa'9) of Formula (II) is αMeArg-Leu. In embodiments, the positions at amino acid 8 (aa'8) and amino acid 9 (aa'9) of Formula (II) is Arg-αMeLeu. In embodiments, the positions at amino acid 8 (aa'8) and amino acid 9 (aa'9) of Formula (II) is azaArg-Leu. In embodiments, the positions at amino acid 8 (aa'8) and amino acid 9 (aa'9) of Formula (II) is Arg-azaLeu. In some embodiments, apelin peptides disclosed herein may be provided in a prodrug form. The term "prodrug" refers to a compound that is made more active (or simply just released) in vivo through metabolism of a precursor drug. Apelin peptides can exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the apelin peptides described herein are structurally modified forms of the peptide that readily undergo chemical changes under physiological conditions to provide the active apelin peptides. Additionally, prodrugs can be converted to the active peptide by chemical or biochemical methods in an ex vivo environment. For example, prodrugs can be slowly converted to an active peptide when placed in a transdermal patch reservoir with a suitable enzyme or chemical reagent. Prodrugs are often useful because, in some situations, they can be easier to administer than the parent peptide. They may, for example, provide enhanced bioavailability by oral administration whereas the parent peptide may be unavailable through such administration routes. The prodrug can also have improved solubility in pharmaceutical compositions over the parent apelin peptide. A wide variety of prodrug derivatives are known in the art, such as those that rely on hydrolytic cleavage or oxidative activation of the prodrug. An example, without limitation, of a prodrug would be an apelin peptide which is administered as a C-terminal ester (the "prodrug"), but then is metabolically hydrolyzed to the C-terminal carboxylic acid, the active entity.

In some embodiments, the disclosure provides compositions containing the apelin peptides disclosed herein. In some embodiments, the composition is a pharmaceutical composition. In certain embodiments, there are provided pharmaceutical compostions containing apelin peptides for use in medicine.

In certain embodiments, apelin peptides disclosed herein may be provided as "pharmaceutically acceptable salts," which may include salts or zwitterionic forms of the peptides which may be water or oil-soluble or dispersible and therapeutically acceptable. Pharmaceutically acceptable salts can also be included therein, for example, hydrochloride, hydrobromide, phosphate, sulfate, maleate, fumarate, tartrates, acetate, propionate, malonate, benzoate, sulfonate, lactate, citrate, succinate, and the like. The salts can be prepared during the final isolation and purification of the peptides or separately by adjusting the pH of the appropriate peptide formulation with a suitable acid or base. The term "pharmaceutically acceptable" means a biologically acceptable formulation, gaseous, liquid or solid, or mixture thereof, which is suitable for one or more routes of administration, in vivo delivery or contact. A "pharmaceutically acceptable" composition is a material that is not biologically or otherwise undesirable, e.g., the material may be administered to a subject without causing substantial undesirable biological effects. Thus, such a pharmaceutical composition may be used, for example, in administering an apelin peptide of the present disclosure to a subject.

Pharmaceutical compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery known to one of skill in the art. Thus, pharmaceutical compositions may include carriers, diluents, or excipients suitable for administration by various routes. Pharmaceutically acceptable excipients include, but are not limited to, liquids such as water, saline, glycerol, sugars and ethanol. Additionally, pharmaceutical compositions may also include auxiliary substances, such as wetting or emulsifying agents, pH buffering substances, and the like.

Apelin peptide may be formulated for parenteral administration by injection. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Apelin peptide may also be formulated for oral administration, such as, in the form of tablets, capsules.

In certain embodiments, the pharmaceutical composition may be formulated to contain a concentration of at least about 0.01% w/w up to about 90% w/w or more of apelin peptide. Apelin peptides of the invention may be administered orally or via injection at a therapeutically effective dosage, such as a dose of from 0.01 to 500 mg/kg per day, from 1 to 400 mg/kg per day, or from 2 to 300 mg/kg per day. The dose range for humans is generally from 5 mg to 2 g per day. The term "therapeutically effective amount," as used herein, when used in connection with treating a subject is intended to qualify the amount of peptides used in the treatment of a particular cardiovascular condition and/or prophylaxis against a particular cardiovascular condition. This amount will achieve the goal of preventing, reducing, or eliminating the damage of myocardial infarction, systemic hypertension, ischemic hear disease, abdominal aortic aneurysm, cardiac allograft vasculopathy, or the like. The therapeutically effective amount will vary depending upon the specific activity of the therapeutic agent (i.e., peptidomimetic of the present disclosure) being used, the severity of the patient's disease state, and the age, physical condition, existence of other disease states, and nutritional status of the patient. Additionally, other medication the patient may be receiving will effect the determination of the therapeutically effective amount of the therapeutic agent to administer.

The unit dosage form may be provided in discrete units may conveniently contain an amount of apelin peptide of the invention which is effective at such dosage or as a multiple of the same, for instance, units containing 5 mg to 500 mg, usually around 10 mg to 200 mg.

A "unit dosage form," as used herein, refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo.

Further, the apelin peptide of the invention may be administered on a daily basis or on a schedule containing days where dosing does not take place. In certain embodiments, dosing may take place every other day. In other embodiments, dosing may take place for five consecutive days of a week, then be followed by two non-dosing days. The choice of dosing schedule will depend on many factors, including, for example, the formulation chosen, route of administration, and concurrent pharmacotherapies, and may vary on a patient-to-patient basis. It is considered within the capacity of one skilled in the art to select a schedule that will maximize the therapeutic benefit and minimize any potential side effects in a subject.

Compositions may be sterile. The compositions may be made in containers suitable for such processes. Such containers include dishes, flasks, roller bottles, bags, bioreactors, vessels, tubes, vials, etc. Containers may be made of materials that include but are not limited to glass, plastic and polymers, such as polystyrene, polybutylene, polypropylene, etc.

Synthesis of Apelin Peptides

Figure 3:
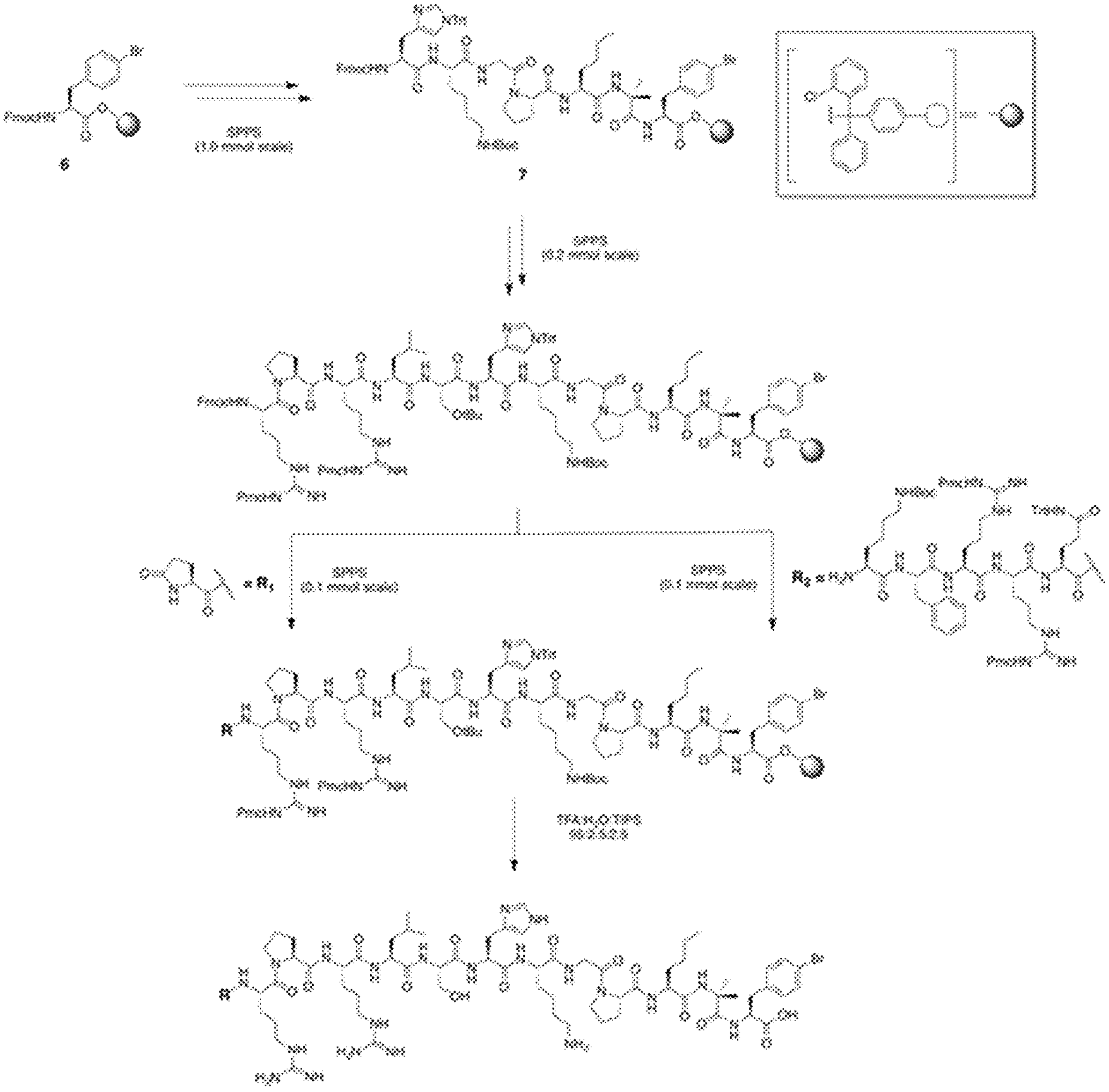
FIG. 3 is a synthetic reaction scheme showing the general SPPS approach for the divergent syntheses of Arg/Leu modified apelin A2 peptides.

The apelin peptides of the present disclosure may be produced by conventional automated peptide synthesis methods. FIG. 3 shows the general SPPS (solid phase peptide synthesis) approach for the divergent syntheses of Arg/Leu modified apelin A2 peptides of the present disclosure.

Diagnostic and Prognostic Compositions

In some embodiments, the apelin peptides disclosed herein can be labeled for detection and used, for example, to detect a binding site for the peptide on the surface or in the interior of a cell. Thus, the fate of the peptide can be followed in vitro or in vivo by using the appropriate method to detect the label. The labeled apelin peptide may also be utilized in vivo for diagnosis and prognosis, or for other types of in situ evaluations.

Examples of suitable detectable labels include radioactive, fluorogenic, chromogenic, or other chemical labels. Useful radiolabels, which are detected by a gamma counter or a scintillation counter or by autoradiography include 3H, 125I, 131I, 35S and 14C. In addition, 131I is also useful as a therapeutic isotope (see below).

Common fluorescent labels include fluorescein isothiocyanate, rhodamine, phycoerythrin, phycocyanin, allophycocyanin, o-phthaldehyde and fluorescamine.

The fluorophore, such as the dansyl group, must be excited by light of a particular wavelength to fluoresce. See, for example, Haugland, Handbook of Fluorescent Probes and Research Chemicals, Sixth Edition, Molecular Probes, Eugene, Oreg., 1996). In general, a fluorescent reagent is selected based on its ability to react readily with an amino function. Examples of such fluorescent probes include the Bodipy (4,4-difluoro-4-bora-3a,4a-diaza-s-indacene) fluorophores which span the visible spectrum (U.S. Pat. Nos. 4,774,339; 5,187,288; 5,248,782; 5,274,113; 5,433,896; 5,451,663). One such member of this group is 4,4-difluoro-5,7-dimethyl-4-bora-3a,4a-diaza-s-indacene-3-propionic acid.

Fluorescein, fluorescein derivatives and fluorescein-like molecules such as Oregon Green and its derivatives, Rhodamine Green and Rhodol Green, are coupled to amine groups using the isocyanate, succinimidyl ester or dichlorotriazinyl-reactive groups. The long wavelength rhodamines, which are basically Rhodamine Green derivatives with substituents on the nitrogens, are among the most photostable fluorescent labeling reagents known. Their spectra are not affected by changes in pH between 4 and 10, an important advantage over the fluoresceins for many biological applications. This group includes the tetramethylrhodamines, X-rhodamines and Texas Red derivatives. Other fluorophores for derivatizing the peptide are those which are excited by ultraviolet light. Examples include cascade blue, coumarin derivatives, naphthalenes (of which dansyl chloride is a member), pyrenes and pyridyloxazole derivatives.

In yet another approach, one or more amino groups is allowed to react with reagents that yield fluorescent products, for example, fluorescamine, dialdehydes such as o-phthaldialdehyde, naphthalene-2,3-dicarboxylate and anthracene-2,3-dicarboxylate. 7-nitrobenz-2-oxa-1,3-diazole (NBD) derivatives, both chloride and fluoride, are useful to modify amines to yield fluorescent products.

Those skilled in the art will recognize that known fluorescent reagents modify groups other than amines, such as thiols, alcohols, aldehydes, ketones, carboxylic acids and amides. Hence, fluorescent substrates can readily be designed and synthesized using these other reactive groups.

The peptide can also be labeled for detection using fluorescence-emitting metals such as 152 Eu, or others of the lanthanide series. These metals can be attached to the peptide using such metal chelating groups as diethylenetriaminepentaacetic acid (DTPA) or ethylenediaminetetraacetic acid (EDTA). The peptide can be made detectable by coupling it to a chemiluminescent compound. The presence of the chemiluminescent-tagged peptide is then determined by detecting the presence of luminescence that arises during the course of a chemical reaction. Examples of particularly useful chemiluminescers are luminol, isoluminol, theromatic acridinium ester, imidazole, acridinium salt and oxalate ester. Likewise, a bioluminescent compound may be used to label the peptide. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In yet another embodiment, colorimetric detection is used, based on chromogenic compounds (chromophores) with high extinction coefficients.

In situ detection of the labeled peptide may be accomplished by removing a histological specimen from a subject and examining it by microscopy under appropriate conditions to detect the label. Those of ordinary skill will readily perceive that any of a wide variety of histological methods (such as staining procedures) can be modified in order to achieve such in situ detection.

The term "diagnostically labeled" means that the peptide has attached to it a diagnostically detectable label. There are many different labels and methods of labeling known to those of ordinary skill in the art. Examples of the types of labels which can be used in conjunction with apelin peptides include radioactive isotopes, paramagnetic isotopes, and compounds which can be imaged by positron emission tomography (PET). Those of ordinary skill in the art will know of other suitable labels for binding to the apelin peptides disclosed herein, or will be able to ascertain such, by routine experimentation. Furthermore, the binding of these labels to the peptide or derivative can be done using standard techniques known to those of ordinary skill in the art.

For diagnostic in vivo radioimaging, the type of detection instrument available is a major factor in selecting a given radionuclide. The radionuclide chosen must have a type of decay which is detectable by a given type of instrument. In general, any conventional method for visualizing diagnostic imaging can be utilized in accordance with embodiments disclosed herein. Another factor in selecting a radionuclide for in vivo diagnosis is that the half-life of a radionuclide be long enough so that it is still detectable at the time of maximum uptake by the target issue, but short enough so that deleterious radiation of the host is minimized. In one embodiment, a radionuclide used for in vivo imaging does not emit particles, but produces a large number of photons in a 140-200 keV range, which may be readily detected by conventional gamma cameras.

For in vivo diagnosis, radionuclides may be bound to peptide either directly or indirectly by using an intermediary functional group. Intermediary functional groups that are often used to bind radioisotopes, which exist as metallic ions, to peptides are the chelating agents, DTPA and EDTA. Examples of metallic ions which can be bound to peptides are 99 Tc, 123 I, 111 In, 131 I, 97 Ru, 67 Cu, 67 Ga, 125 I, 68 Ga, 72 As, 89 Zr, and 201 TI. Generally, the dosage of peptide labeled for detection for diagnostic use will vary depending on considerations such as age, condition, sex, and extent of disease in the patient, counterindications, if any, and other variables, to be adjusted by the individual physician.

In another embodiment, the apelin peptides disclosed herein may be used as affinity ligands for binding the peptide's receptor in assays, preparative affinity chromatography or solid phase separation. Such compositions may also be used to enrich, purify or isolate cells to which the peptide or derivative binds, preferably through a specific receptor-ligand interaction. The peptide or derivative may be immobilized using common methods known in the art, e.g. binding to CNBr-activated Sepharose or Agarose, NHS-Agarose or Sepharose, epoxy-activated Sepharose or Agarose, EAH-Sepharose or Agarose, streptavidin-Sepharose or Agarose in conjunction with biotinylated peptide or derivatives. In general the apelin peptides may be immobilized by any other method which is capable of immobilizing these compounds to a solid phase for the indicated purposes. See, for example Affinity Chromatography: Principles and Methods (Pharmacia LKB Biotechnology). Thus, one embodiment is a composition comprising any of the peptides, derivatives or peptidomimetics described herein, bound to a solid support or a resin. The compound may be bound directly or via a spacer, such as an aliphatic chain having about 2-12 carbon atoms.

By "solid phase" or "solid support" or "carrier" is intended any support or carrier capable of binding the peptide or derivative. Well-known supports, or carriers, in addition to Sepharose or Agarose described above are glass, polystyrene, polypropylene, polyethylene, dextran, nylon, amylases, natural and modified celluloses such as nitrocellulose, polyacrylamides, polyvinylidene difluoride, other agaroses, and magnetite, including magnetic beads. The carrier can be totally insoluble or partially soluble. The support material may have any possible structural configuration so long as the coupled molecule is capable of binding to receptor material. Thus, the support configuration may be spherical, as in a bead, or cylindrical, as in the inside surface of a test tube or microplate well, or the external surface of a rod. Alternatively, the surface may be flat such as a sheet, test strip, bottom surface of a microplate well, etc.

Production of Peptides and Derivatives

The peptides disclosed herein may be prepared using recombinant DNA technology. However, given their length, they may be more easily prepared using solid-phase synthesis, such as that generally described by Merrifield, J. Amer. Chem. Soc., 85:2149-54 (1963), although other equivalent chemical syntheses known in the art are also useful. Solid-phase peptide synthesis may be initiated from the C-terminus of the peptide by coupling a protected alpha-amino acid to a suitable resin. Such a starting material can be prepared by attaching an alpha-amino-protected amino acid by an ester linkage to a chloromethylated resin or to a hydroxymethyl resin, or by an amide bond to a BHA resin or MBHA resin.

The preparation of the hydroxymethyl resin is described by Bodansky et al., 1966. Chloromethylated resins are commercially available from BioRad Laboratories, Richmond, Calif. and from Lab. Systems, Inc. The preparation of such a resin is described by Stewart et al., 1969. BHA and MBHA resin supports are commercially available and are generally used only when the desired polypeptide being synthesized has an unsubstituted amide at the C-terminus.

The amino acids can be coupled to the growing peptide chain using techniques well known in the art for the formation of peptide bonds. For example, one method involves converting the amino acid to a derivative that will render the carboxyl group of the amino acid more susceptible to reaction with the free N-terminal amino group of the growing peptide chain. Specifically, the C-terminal of the protected amino acid can be converted to a mixed anhydride by the reaction of the C-terminal with ethyl chloroformate, phenyl chloroformate, sec-butyl chloroformate, isobutyl chloroformate, or pivaloyl chloride or the like acid chlorides. Alternatively, the C-terminal of the amino acid can be converted to an active ester, such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole. Another coupling method involves the use of a suitable coupling agent, such as N,N'-dicyclohexylcarbodiimide or N,N'-diisopropylcarbodiimide. Other appropriate coupling agents, apparent to those skilled in the art, are disclosed in Gross et al. 1979, which is hereby incorporated by reference.

The alpha-amino group of each amino acid employed in the peptide synthesis must be protected during the coupling reaction to prevent side reactions involving their active alpha-amino function. Certain amino acids contain reactive side-chain functional groups (e.g., sulfhydryl, amino, carboxyl, and hydroxyl) and such functional groups must also be protected with suitable protecting groups to prevent a chemical reaction from occurring at either (1) the alpha-amino group site or (2) a reactive side chain site during both the initial and subsequent coupling steps.

In the selection of a particular protecting group to be used in synthesizing the peptides, the following general rules are typically followed. Specifically, an alpha-amino protecting group (1) should render the alpha-amino function inert under the conditions employed in the coupling reaction, (2) should be readily removable after the coupling reaction under conditions that will not remove side-chain protecting groups and will not alter the structure of the peptide fragment, and (3) should substantially reduce the possibility of racemization upon activation, immediately prior to coupling.

On the other hand, a side-chain protecting group (1) should render the side chain functional group inert under the conditions employed in the coupling reaction, (2) should be stable under the conditions employed in removing the alpha-amino protecting group, and (3) should be readily removable from the desired fully-assembled peptide under reaction conditions that will not alter the structure of the peptide chain.

It will be apparent to those skilled in the art that the protecting groups known to be useful for peptide synthesis vary in reactivity with the agents employed for their removal. For example, certain protecting groups, such as triphenylmethyl and 2-(p-biphenyl)isopropyloxycarbonyl, are very labile and can be cleaved under mild acid conditions. Other protecting groups, such as t-butyloxycarbonyl (BOC), t-amyloxycarbonyl, adamantyl-oxycarbonyl, and p-methoxybenzyloxycarbonyl, are less labile and require moderately strong acids for their removal, such as trifluoroacetic, hydrochloric, or boron trifluoride in acetic acid. Still other protecting groups, such as benzyloxycarbonyl (CBZ or Z), halobenzyloxycarbonyl, p-nitrobenzyloxycarbonyl cycloalkyloxycarbonyl, and isopropyloxycarbonyl, are even less labile and require even stronger acids, such as hydrogen fluoride, hydrogen bromide, or boron trifluoroacetate in trifluoroacetic acid, for their removal. Suitable protecting groups, known in the art are described in Gross et al. 1981.

Among the classes of amino acid protecting groups useful for protecting the alpha-amino group or for protecting a side chain group are included the following:

(1) For an alpha-amino group, three typical classes of protecting groups are: (a) aromatic urethane-type protecting groups, such as fluorenylmethyloxycarbonyl (FMOC), CBZ, and substituted CBZ, such as, p-chlorobenzyloxycarbonyl, p-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type protecting groups, such as BOC, t-amyloxycarbonyl, isopropyloxycarbonyl, 2-(p-biphenyl)isopropyloxycarbonyl, allyloxycarbonyl and the like; and (c) cycloalkyl urethane-type protecting groups, such as cyclopentyloxycarbonyl, adamantyloxycarbonyl, and cyclohexyloxycarbonyl. The alpha-amino protecting groups BOC and FMOC are commonly used and may provide the widest selection for commericially available protected amino acids.

(2) For the side chain amino group present in Lys, protection may be by any of the groups mentioned above in (1) such as BOC, 2-chlorobenzyloxycarbonyl and the like.

(3) For the guanidino group of Arg, protection may be provided by nitro, tosyl, CBZ, adamantyloxycarbonyl, 2,2,5,7,8-pentamethylchroman-6-sulfonyl, 2,3,6-trimethyl-4-methoxyphenylsulfonyl, or BOC groups.

(4) For the hydroxyl group of Ser or Thr, protection may be, for example, by t-butyl; benzyl (BZL); or substituted BZL, such as p-methoxybenzyl, p-nitrobenzyl, p-chlorobenzyl, o-chlorobenzyl, and 2,6-dichlorobenzyl.

(5) For the carboxyl group of Asp or Glu, protection may be, for example, by esterification using such groups as BZL, t-butyl, cyclohexyl, cyclopentyl, and the like.

(6) For the imidazole nitrogen of His, the benzyloxymethyl (BOM) or tosyl moiety is suitably employed as a protecting group.

(7) For the phenolic hydroxyl group of Tyr, a protecting group such as tetrahydropyranyl, tert-butyl, trityl, BZL, chlorobenzyl, 4-bromobenzyl, and 2,6-dichlorobenzyl are suitably employed. One such protecting group is bromobenzyloxycarbonyl.

(8) For the side chain amino group of Asn or Gln, xanthyl (Xan) may be employed.

(9) For Met, the amino acid may be left unprotected.

(10) For the thio group of Cys, p-methoxybenzyl is typically employed.

The first C-terminal amino acid of the growing peptide chain is typically protected at the alpha-amino position by an appropriately selected protecting group such as BOC and the carboxyl residue attached to a support, such as an amine functionalized support. Following the coupling of the BOC-protected amino acid to the resin support, the alpha-amino protecting group is usually removed, typically by using trifluoroacetic acid (TFA) in methylene chloride or TFA alone. The alpha-amino group de-protection reaction can occur over a wide range of temperatures, but is usually carried out at a temperature between about 0° C. and room temperature.

Other standard alpha-amino group de-protecting reagents, such as HCl in dioxane, and conditions for the removal of specific alpha-amino protecting groups are within the skill of those working in the art, such as those described in Lubke et al., 1975, which is hereby incorporated by reference. Following the removal of the alpha-amino protecting group, the unprotected alpha-amino group, generally still side-chain protected, can be coupled in a stepwise manner in the intended sequence.

An alternative to the stepwise approach is the fragment condensation method in which pre-formed peptides of short length, each representing part of the desired sequence, are coupled to a growing chain of amino acids bound to a solid phase support. For this stepwise approach, a particularly suitable coupling reagent is N,N'-dicyclohexylcarbodiimide or diisopropylcarbodiimide. Also, for the fragment approach, the selection of the coupling reagent, as well as the choice of the fragmentation pattern needed to couple fragments of the desired nature and size are important for success and are known to those skilled in the art.

Each protected amino acid or amino acid sequence is usually introduced into the solid-phase reactor in amounts in excess of stoichiometric quantities, and the coupling is suitably carried out in an organic solvent, such as dimethylformamide (DMF), $CH_2Cl_2$ or mixtures thereof. If incomplete coupling occurs, the coupling procedure is customarily repeated before removal of the N-amino protecting group in preparation for coupling to the next amino acid. Following the removal of the alpha-amino protecting group, the remaining alpha-amino and side-chain-protected amino acids can be coupled in a stepwise manner in the intended sequence. The success of the coupling reaction at each stage of the synthesis may be monitored. A method of monitoring the synthesis is by the ninhydrin reaction, as described by Kaiser et al, 1970. The coupling reactions can also be performed automatically using well-known commercial methods and devices, for example, a Beckman 990 Peptide Synthesizer.

Upon completion of the desired peptide sequence, the protected peptide may be cleaved from the resin support, and all protecting groups removed. The cleavage reaction and removal of the protecting groups may be suitably accomplished concomitantly or consecutively with de-protection reactions. When the bond anchoring the peptide to the resin is an ester bond, it can be cleaved by any reagent that is capable of breaking an ester linkage and of penetrating the resin matrix. One especially useful method is by treatment with liquid anhydrous hydrogen fluoride. This reagent will usually not only cleave the peptide from the resin, but will also remove all acid-labile protecting groups and, thus, will directly provide the fully de-protected peptide. When additional protecting groups that are not acid-labile are present, additional de-protection steps must be carried out. These steps can be performed either before or after the hydrogen fluoride treatment described above, according to specific needs and circumstances.

When a chloromethylated resin is used, the hydrogen fluoride cleavage/de-protection treatment generally results in the formation of the free peptide acids. When a benzhydrylamine resin is used, the hydrogen fluoride treatment generally results in the free peptide amides. Reaction with hydrogen fluoride in the presence of anisole and dimethylsulfide at 0° C. for one hour will typically remove the side-chain protecting groups and, concomitantly, release the peptide from the resin.

When it is desired to cleave the peptide without removing protecting groups, the protected peptide-resin can be subjected to methanolysis, thus yielding a protected peptide in which the C-terminal carboxyl group is methylated. This methyl ester can be subsequently hydrolyzed under mild alkaline conditions to give the free C-terminal carboxyl group. The protecting groups on the peptide chain can then be removed by treatment with a strong acid, such as liquid hydrogen fluoride. A particularly useful technique for methanolysis is that of Moore et al., 1977, in which the protected peptide-resin is treated with methanol and potassium cyanide in the presence of a crown ether.

Other methods for cleaving a protected peptide from the resin when a chloromethylated resin is employed include (1) ammoniolysis and (2) hydrazinolysis. If desired, the resulting C-terminal amide or hydrazide can be hydrolyzed to the free C-terminal carboxyl moiety, and the protecting groups can be removed conventionally. The protecting group present on the N-terminal alpha-amino group may be removed either before, or after, the protected peptide is cleaved from the support. Purification of the apelin peptides disclosed herein may be achieved using chromatographic techniques, such as preparative HPLC (including reverse phase HPLC), gel permeation, ion exchange, partition chromatography, affinity chromatography (including monoclonal antibody columns), and the like, or other conventional techniques such as countercurrent distribution or the like.

An aspect of the present apelin peptides includes a method of treating an apelin pathway disorder by administering the apelin peptide or a pharmaceutical formulation thereof to a subject having the apelin pathway disorder.

The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Human subjects include fetal, neonatal, infant, juvenile and adult subjects.

The term "apelin pathway disorder," as used herein, refers to a disorder resulting from the abnormality of the apelin pathway. In some embodiments, the apelin pathway disorder is a cardiac disease, such as, but are not limited to, systemic arterial hypertension, systemic hypertension, abdominal aortic aneurysm, pulmonary arterial hypertension, heart failure, myocardial ischemic-reperfusion injury, ischemic heart disease, cardiac allograft vasculopathy, myocardial infarction, and high blood pressure.

Reducing Cardiac Reperfusion Injury Following Myocardial Infarction

In some embodiments, there are provided methods of reducing cardiac reperfusion injury following myocardial infarction in a subject comprising administering to the subject an effective amount of an apelin receptor agonist comprising a peptidomimetic of Formula (I) or Formula (II) of the disclosure, or pharmaceutically acceptable salts thereof. In some embodiments, the apelin peptide to prevent damage following myocardial infarction may be a peptidomimetic of Formula (I) or Formula (II) of the disclosure, or pharmaceutically acceptable salts thereof. In some embodiments, combinations of apelin peptides may be employed. In some embodiments, the administering step is carried out intravenously.

As used herein, the term "cardiac reperfusion injury" refers to an injury of a heart, caused by putting the heart into an ischemic condition such as by acute coronary syndromes, thomboembolic events, surgery or resuscitation from cardiac arrest.

As disclosed herein, APLN is a central regulator of the myocardial response to infarction and ischemia and pharmacologically targeting this pathway provides a means of developing new therapeutic agents. Apelin is predominantly expressed in the endocardial and vascular endothelial cells while the APJ receptor (apelin receptor) is localized to endothelial and smooth muscle cells as well as cardiomyocytes, allowing for autocrine and paracrine effects of apelin in the heart (Pitkin S. L., et al. *Pharmacol. Rev.* 62:331-342, (2010); Chen M. M., et al. *Circulation.* 108:1432-1439, (2003); Kleinz M J, et al. *Regul Pept.* 126:233-240, (2005)). Apelin mediates positive inotropic effect on isolated cardiomyocytes (Wang C, et al. *Am J Physiol Heart Circ Physiol.* 294:H2540-2546, (2008)), isolated perfused rat heart (Szokodi I, et al. *Circ Res.* 91:434-440, (2002)) and in vivo (Berry M F, et al. *Circulation.* 110:11187-193, (2004)) and mediates endothelium-dependent vasodilation (Pitkin S L et al. *Br J Pharmacol.* 160:1785-1795, (2010)). Genetic variation in the APJ receptor modifies the progression of heart failure in patients with dilated cardiomyopathy (Sarzani R, et al. *J Card Fail.* 13:521-529, (2007)) and the apelin/APJ system is compromised in human heart failure (Chen M. M., et al. *Circulation.* 108:1432-1439, (2003); Chong K S, et al. *Eur J Heart Fail.* 8:355-360, (2006)). In patients with chronic heart failure, apelin administration increased cardiac index and lowered peripheral vascular resistance in the absence of hypotension providing a promising new drug target for heart failure (Japp A G, et al. *Circulation.* 121: 1818-1827, (2010)).

Apelin promotes the phosphorylation of Akt and increases the proliferation of endothelial cells in vitro indicating a pro-angiogenic role (Kidoya H, et al. *EMBO J.* 27:522-534, (2008); Kidoya H, et al. *Blood.* 115:3166-3174, (2010); Tao J, et al. *Am J Physiol Heart Circ Physiol.* 301:H1471-1486, (2011)). Given the plethora of biochemical and cellular effects of apelin, it was postulated that loss of apelin might enhance the susceptibility to myocardial ischemic injury. Apelin peptides disclosed herein may prevent myocardial ischemic reperfusion injury, which can be demonstrated using the Langendorff protocol (described in Example section). Apelin peptides disclosed herein may rescue the heart from ischemic reperfusion injury compared to native isoforms (e.g., native isoform 2).

Tachycardia is directly correlated with native apelin isoforms binding to the receptor. (Cheng, X., et al., *European Journal of Pharmacology,* 470, 171-175 (2003)). Apelin peptides disclosed herein may demonstrate an ability to induce tachycardia.

Modulating Vascular Tone and Blood Pressure

Native apelin peptides have been shown to play a central role in vascular disease in other pathological states including pulmonary hypertension (Alastalo, supra; Kim, J., et al. *Nat. Med.* 19:74-82 (2013)) and diabetes (Sawane, M., et al. *Diabetes* 62:1970-80 (2013); Day, R. T., et al. *Am. J. Physiol. Renal Physiol.* 304:F788-800 (2013)) It was indicated that a loss of apelin function is associated with worsening vascular disease with direct implications that apelin peptides can reverse or prevent the progression of these disorders. Vascular tone refers to the degree of constriction experienced by a blood vessel relative to its maximally dilated state.

In some embodiments, there are provided methods of modulating vascular tone in a subject comprising administering to the subject an effective amount of an apelin receptor agonist comprising an apelin peptide comprising a peptidomimetic of Formula (I) or Formula (II) of the disclosure, or pharmaceutically acceptable salts thereof. In some embodiments, combinations of apelin peptides may be employed.

In some embodiments, there are provided methods of reducing blood pressure in a subject comprising administering to the subject an effective amount of an apelin receptor agonist comprising an apelin peptide comprising a peptidomimetic of Formula (I) or Formula (II), or pharmaceutically acceptable salts thereof. In some embodiments, the administering step is carried out intravenously.

Modulating Apelin Receptor

In some embodiments, there are provided methods of modulating an apelin pathway disorder comprising contacting the apelin receptor with an apelin peptide comprising a peptidomimetic of Formula (I) or Formula (II) of the disclosure, or pharmaceutically acceptable salts thereof. In some embodiments, combinations of apelin peptides may be employed. In some such embodiments, the contacting step is performed in vivo. In some such embodiments, the apelin peptide is an apelin receptor agonist.

In some embodiments, there are provided methods of modulating an apelin pathway disorder in a subject comprising administering to the subject a therapeutically effective amount of an apelin peptide comprising a peptidomimetic of Formula (I) or Formula (II) of the disclosure, or pharmaceutically acceptable salts thereof. In some embodiments, combinations of apelin peptides may be employed. In some embodiments, the administering step is carried out intravenously.

Modulating apelin receptor may be useful in numerous biological contexts where the receptor is expressed. In some embodiments, apelin peptides disclosed herein may be used to treat and/or reduce HIV-1 infection. Cayabyab et al., *J. Virol.* 74: 11972-11976 (2000) observed that in addition to the chemokine receptors CCR5 and CXCR4, primary HIV-1 isolates can also use APJ as a co-receptor. CAT reporter assays showed that synthetic apelin peptides inhibited HIV-1 entry into CD4-APJ-expressing cells.

As used herein, the singular forms "a", "and," and "the" include plural referents unless the context clearly indicates otherwise.

The following Examples are being submitted to illustrate embodiments of the present disclosure. Nevertheless, one skilled in the art, without departing from the spirit and scope of the invention, can make various changes and modifications of the invention to adapt it to various usages and conditions. The following Examples are intended to be illustrative only and are not intended to limit the scope of the present disclosure.

EXAMPLES

Reagents, Solvents and Purification

Commercially available chemical and biological reagents were purchased from Sigma-Aldrich Canada, Chem-Impex International Inc., Fisher Scientific Ltd., Alfa Aesar Ltd., R&D Systems, Tocris Bioscience, Harvard Apparatus, Caledon or VWR International, and used without further purification unless otherwise stated. All solvents were of American Chemical Society (ACS) grade and were used without further purification. All anhydrous reactions were conducted under positive pressure of argon using flame-dried glassware. Solvents for anhydrous reactions were distilled prior to use: dichloromethane and dichloroethane were distilled over calcium hydride, tetrahydrofuran and diethyl ether were distilled over sodium with benzophenone as an indicator, and methanol was distilled over magnesium. HPLC grade acetonitrile, dimethylformamide, 2-propanol, hexanes and methanol were used without further purification. Commercially available ACS grade solvents (>99.0% purity) were used for column chromatography without further purification. Deionized water was obtained from a Milli-Q reagent water filtration system (Millipore Co., Milford, Mass.). The removal of solvents in vacuo was performed by evaporation under reduced pressure using a Büchi rotary evaporator. Automated Solid Phase Peptide Synthesis was performed on a PreludeX (Gyros protein technologies). All reactions and fractions from column chromatography were monitored by thin layer chromatography (TLC) using glass plates with a UV fluorescent indicator (normal $SiO_2$, Merck 60 $F_{254}$). Visualization was performed following: UV absorption by fluorescence quenching, staining with phosphomolybdic acid in ethanol (10 g/100 mL), ninhydrin (ninhydrin:acetic acid:n-butanol, 0.6 g:6 mL:200 mL) or potassium permanganate ($KMnO_4$:$K_2CO3$:NaOH:$H_2O$, 1.5 g:10 g:0.12 g:200 mL). Flash chromatography was performed using Merck type 60, 230-400 mesh silica gel. Semi-preparative and analytical scale high performance liquid chromatography (HPLC) were performed on a Gilso393 chromatograph equipped with model 322 pump heads, a model 171 diode array detector, a FC203B fraction collector and a Rheodyne 7725i injector fitted with a 1000 pL sample loop. Columns used for purification were: Supelco As centis Si, C18 100 Å, 5 μm, 250 mm×4.6 mm; Restek Viva, BiPhenyl 300 Å, 5 μm, 250 mm×4.6 mm; and Vydac BiPhenyl, 300 Å, 5 μm, 250 mm×4.6 mm. HPLC solvents were filtered through a Millipore filtration system under vacuum prior to use. Peptides were purified to >95% purity as assessed by analytical reinjection.

Characterization

Optical rotations were measured on a Perkin Elmer 241 polarimeter with a microcell (10 cm, 1 mL) at ambient temperature and are reported in units of $10^{-1}$ deg $cm^2$ $g^{-1}$. All reported optical rotations were referenced against air and measured at the sodium D line (λ=589.3 nm).

Infrared spectra (IR) were recorded on a Nicolet Magna 750 or a 20SX FT-IR spectrometer. Cast refers to the evaporation of a solution on a NaCl plate.

Nuclear magnetic resonance (NMR) spectra were recorded on an Agilent/Varian Inova 600, Inova 400, Inova 300, DD2 MR 400, VNMRS 700 or Unity 500 spectrometer at 27° C. For $^1H$ (300, 400, 500, 600. or 700 MHz) spectra, δ values were referenced to $CDCl_3$ (7.26 ppm), $D_2O$ (4.79 ppm) or $CD_3OD$ (3.30 ppm), and for $^{13}C$ (100, 125, 150 or 175 MHz) spectra, δ values were referenced to $CDCl_3$ (77.0 ppm) or $CD_3OD$ (49.0 ppm), as the solvents. Reported splitting patterns are abbreviated as s=singlet, d=doublet, t=triplet, q=quartet, sept=septet, m=multiplet.

Mass spectra (MS) were recorded on a Kratos AEIMS-50, Bruker 9.4T Apex-Qe FTICR (high resolution, HRMS) or on a Perspective Biosystems Voyager™ Elite MALDI-TOF MS using 4-hydroxy-α-cyanocinnamic acid (HCCA) as a matrix. MS/MS was performed on a Bruker Ultraflextreme MALDI/TOF/TOF. LCMS was performed on an Agilent Technologies 6130 LCMS using a Core-Shell C18 column (1.7 μm, 100 Å, Phenomenex Kintex).

General Apelin Peptide SPPS Elongation Method

A suspension of resin in DMF (10 mL) was bubbled under Ar gas for 15 minutes to swell. The N-terminal Fmoc group was removed by bubbling a solution of 20% piperidine in DMF (3×10 mL) for 3 minutes, washing considerably with DMF (3×10 mL) after each deprotection. Fmoc-deprotection was monitored by TLC, with the dibenzofulvene-piperidine adduct appearing as aas a bright purple spot under UV. To pre-activate the amino acid solution, one of the following procedures was followed: (1) DIPEA (2.2 eq) was added to a solution of Fmoc-protected amino acid (1.1 eq compared to resin loading), HOBt (1.1 eq), and PyBOP (1.1 eq) in DMF (10 mL) and stirred for 5 minutes, or (2) DIPEA (6.0 equivalents) was added to a solution of Fmoc-protected amino acid (3.0 equivalents compared to resin loading), HATU (3.0 equivalents), and HOAt (1-hydroxy-7-azabenzotriazole) (3.0 equivalents) in DMF (10 mL) and stirred for 5 minutes. The activated amino acid solution was added to the resin and bubbled under Ar gas for 1-3 h. The resin was washed with DMF (3×10 mL) and the extent of coupling was assessed by either: i) cleaving a small sample of resin with a solution of 95:2.5:2.5 TFA:TIPS:$H_2O$ for 1 h and MALDI-TOF analysis or ii) performing a Kaiser test to detect the presence of free amines. A solution of 20% acetic anhydride in DMF (10 mL) was added to the resin and bubbled under Ar gas for 10 minutes to end-cap any unreacted amines. The resin was rinsed thoroughly with DMF (3×10 mL) and subjected to Fmoc-deprotection to further elongate the peptide, or rinsed with $CH_2Cl_2$ (3×10 mL) and MeOH (3×10 mL), dried thoroughly, and stored under Ar gas at −20° C.

General Method for Apelin Peptide Resin Cleavage

Resin-bound apelin peptide was suspended in 95:2.5:2.5 TFA:TIPS:H2O with shaking under an Ar atmosphere for 2-3 hours. The resin was removed via filtration through glass wool, rinsed with TFA, and the solution concentrated in vacuo. Cold diethyl ether (1 mL, or 2×5 mL) was added to triturate the crude peptide. The diethyl ether and peptide precipitate were decanted into a tube and centrifuged for 1 minute to pellet the peptide. The diethyl ether was then decanted, and the pellet was dissolved in 10% aqueous acetonitrile, 0.1% TFA.

Apelin Peptide Purification Methods

Peptides were purified using C18 RP-HPLC using aqueous 0.1% TFA (solvent A) and 0.1% TFA in acetonitrile (solvent B) as eluents.

Example 1

Synthesis of D-Leu Peptides of Pyr-1-Apelin-13 A2 8 and Apelin-17 A2 9

D-Substituted apelin A2 peptides were easily accessible due to the commercial availability of Fmoc-protected D-amino acids. Following the Fmoc-SPPS strategy outlined in FIG. 3, D-Leu peptides of pyr-1-apelin-13 A2 8 and apelin-17 A2 9 were synthesized.

Example 2

Figure 4:
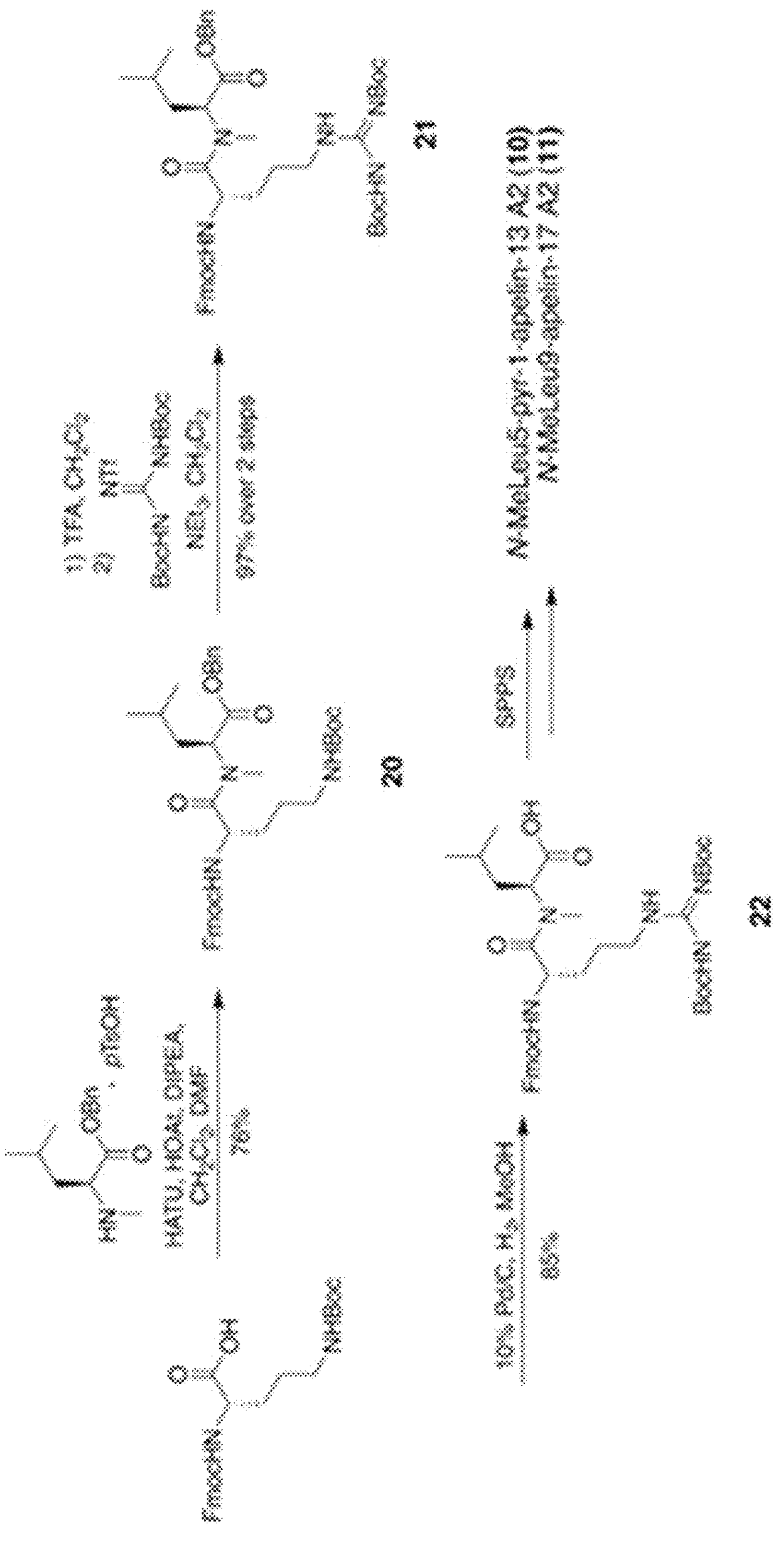
FIG. 4 is a synthetic scheme of dipeptide 22 for the preparation of N-methyl leucine apelin A2 peptides 10 and 11.

Synthesis of Dipeptide 22 for the Preparation of α-Methyl Leucine Apelin A2 Peptides 10 and 11

α-methylated Leu dipeptide 20 was synthesized through the HATU coupling of commercially available α-methylleucine benzyl ester p-TsOH salt with Fmoc-Orn(Boc)-OH (Orn=ornithine) (FIG. 4). The ornithine 8-amine was deprotected under acidic conditions, and then guanidinylated with 1,3-di-Boc-2-(trifluoromethylsulfonyl)guanidine to produce di-Boc protected arginine dipeptide 21. Benzyl ester removal under Pd-catalyzed hydrogenolysis generated free acid 22, which was incorporated into α-MeLeu apelin 13 and 17 A2 peptides 10 (SEQ ID NO:10) and 11 (SEQ ID NO:11) respectively.

Example 3

Synthesis of Dipeptide 29 for the Preparation of α-Methyl Leucine Apelin A2 Peptides 12 and 13

Figure 5:
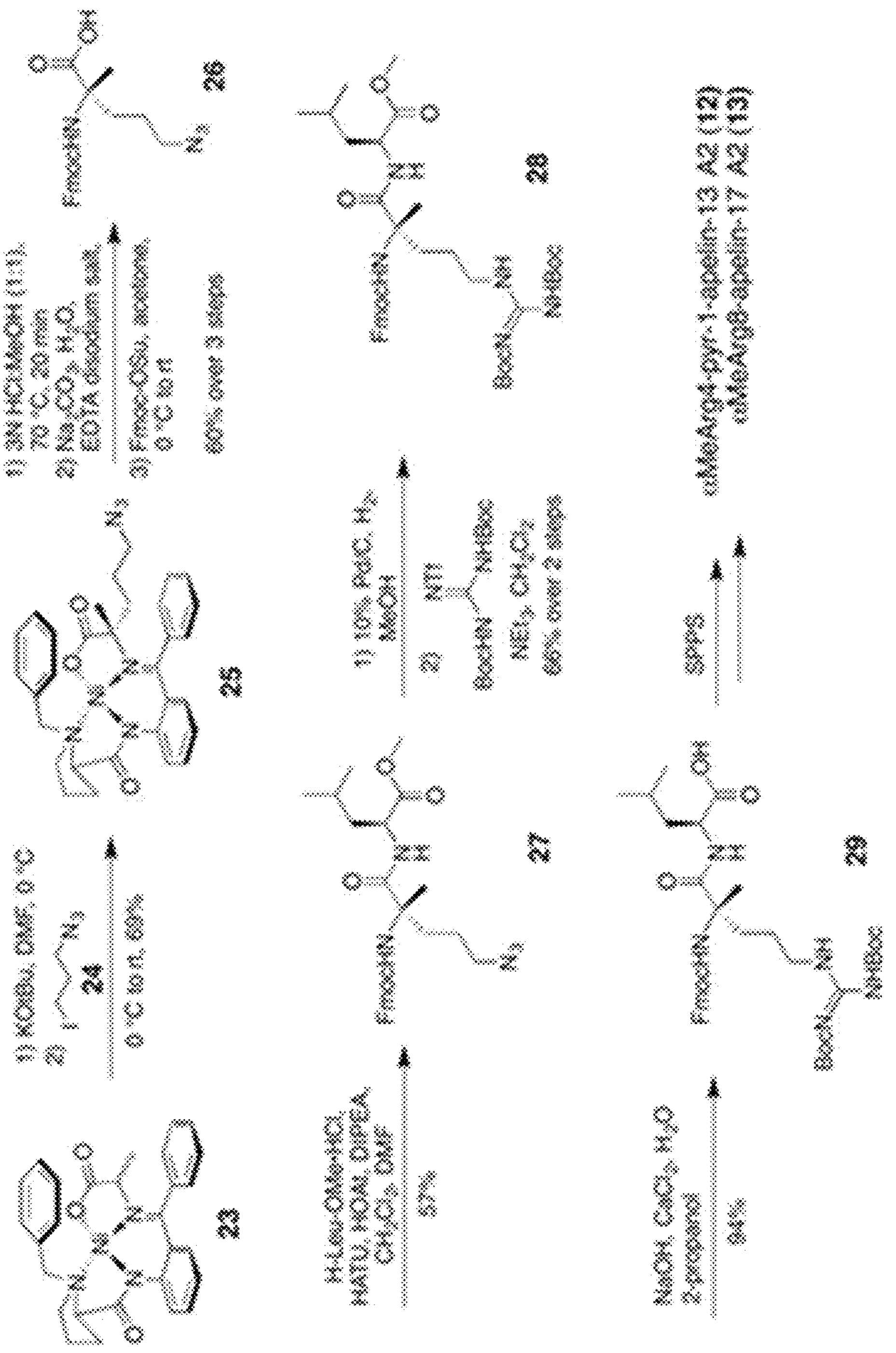
FIG. 5 is a synthetic scheme of dipeptide 29 for the preparation of α-methyl arginine apelin A2 peptides 12 and 13.

The synthesis of dipeptide 29 is outlined in FIG. 5. Steric occlusion of the susceptible amide bond through α-methylation had previously been successful in conferring resistance to ACE2 by the incorporation of Aib N-terminal to the monocarboxypeptidase cleavage site. (Wang, W., et al. *J. Am. Heart Assoc.* 2, e000249 (2013)). Ni-Schiff base complex 23 was used to enantioselectively prepare target α-methylated amino acids due to: ease of synthesis; recyclability of the chiral ligand; and ability to separate individual diastereomers by flash chromatography Ala-Ni(II)-(5)-BPB complex 23 was synthesized according to literature protocol (Belokon', Y. N., et al. *Tetrahedron: Asymmetr:* 9, 4249-4252 (1998)) and was used to divergently synthesize both α-methyl arginine and α-methyl leucine amino acids.

For the synthesis of α-methyl arginine, 23 was deprotonated with KOtBu and alkylated with azido-3-iodopropane (24) to generate α, α-disubstituted Ni-complex 25. The desired (S,S)-diastereomer was purified by silica flash chromatography in 69% yield, and the absolute stereochemistry was confirmed by X-ray crystallography (CCDC 1528624. Complex 25 was hydrolyzed under acidic conditions and the resulting amino acid was Fmoc-protected (26). A HATU-mediated peptide coupling with H-Leu-OMe HCl salt afforded dipeptide 27, which was subsequently converted to αMe-Arg containing dipeptide 28 through azide hydrogenolysis and guanidinylation. Methyl ester deprotection gave the SPPS-compatible dipeptide 29 for the eventual preparation of αMeArg peptides 12 and 13.

Example 4

Synthesis of Dipeptide 33 for the Preparation of α-Methyl Leucine Apelin A2 Peptides 14 and 15

Figure 6:
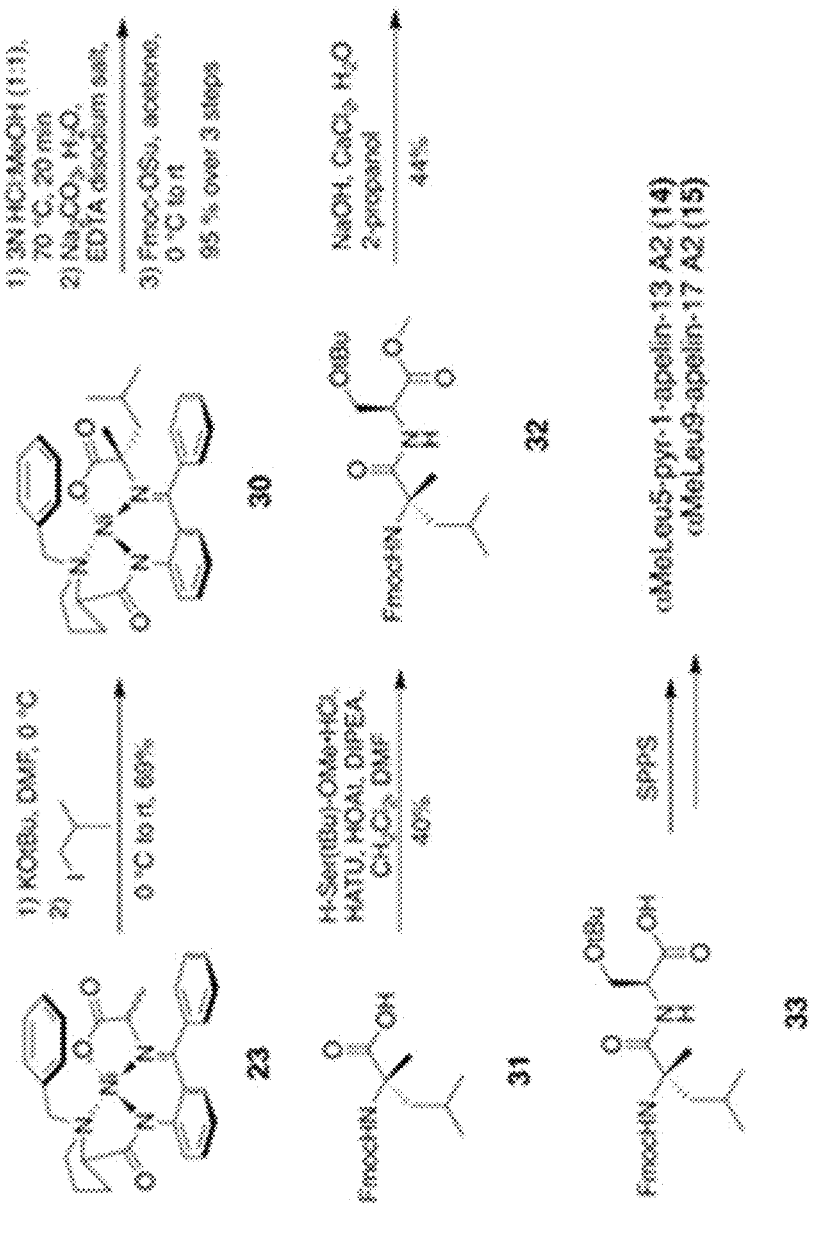
FIG. 6 is a synthetic scheme of dipeptide 33 for the preparation of α-methyl leucine apelin A2 peptides 14 and 15.

The synthesis of dipeptide 33 is outlined in FIG. 6. To prepare α-methyl leucine, 23 was alkylated with 2-methyl-1-iodopropane to generate the desired (S,5)-diastereomer 30, with the absolute stereochemistry confirmed by X-ray crystallography. Acid hydrolysis followed by Fmoc-protection produced amino acid 31, which was subsequently coupled to H-Ser(tBu)-OMe to give dipeptide 32. Methyl ester deprotection gave the SPPS-compatible dipeptide 33, which was used for αMeLeu apelin peptides 14 and 15.

Example 5

Synthesis of Azatripeptide 39 for the Preparation of Aza-Arginine Apelin A2 Peptides 16 and 17

Figure 7:
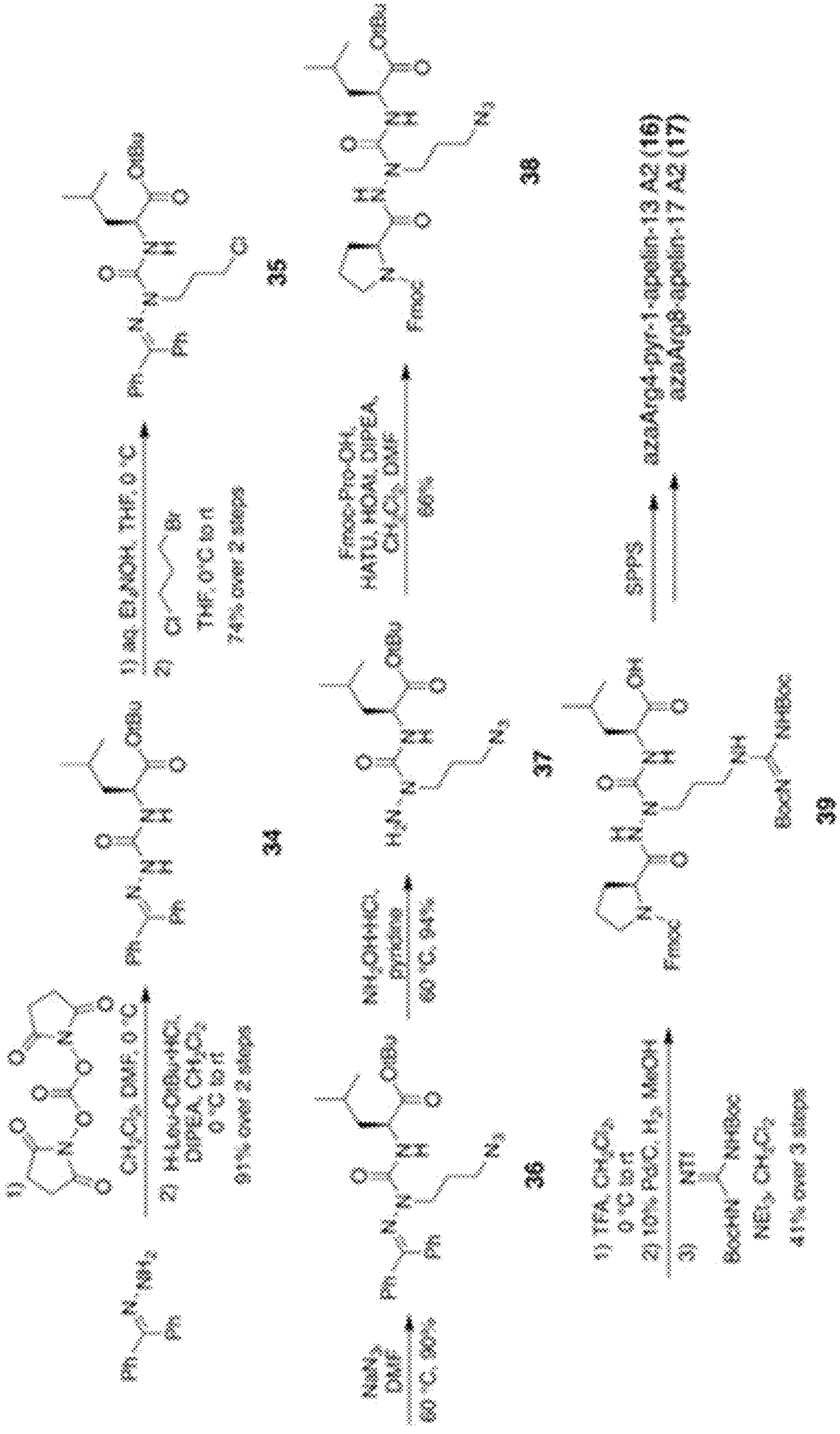
FIG. 7 is a synthetic scheme of dipeptide 39 for the preparation of aza-arginine apelin A2 peptides 16 and 17.

The synthesis of dipeptide 39 is outlined in FIG. 7. Azadipeptide 34 was prepared by the sequential addition of disuccinimidyl carbonate, then a solution of H-Leu-OtBu in DIPEA (N,N-diisopropylethylamine) to benzophenone hydrazone analogous to previously established literature protocol. (Traore, M., et al., *Org. Lett.* 16, 3588-3591 (2014), Garcia-Ramos, Y., et al., *J. Pept. Sci.* 19, 725-729 (2013)). Regioselective semicarbazone alkylation was achieved with tetraethylammonium hydroxide and 3-chloro-1-bromopropane to yield chloroalkylated product 35. Displacement of the primary alkyl chloride with sodium azide afforded 36, which was deprotected to semicarbazide 37 with hydroxylamine hydrochloride. Semicarbazide 37 was aminoacylated with the next N-terminal amino acid (Fmoc-Pro-OH) to generate azatripeptide 38. The SPPS compatible tripeptide 39 was synthesized following tert-butyl ester deprotection, hydrogenolysis of the azide, and guanidinylation of the primary amine. Tripeptide 39 was incorporated into azaArg apelin peptides 16 and 17.

Example 6

Synthesis of Azatripeptide 45 for the Preparation of Aza-Leucine Apelin A2 Peptides 18 and 19

Figure 8:
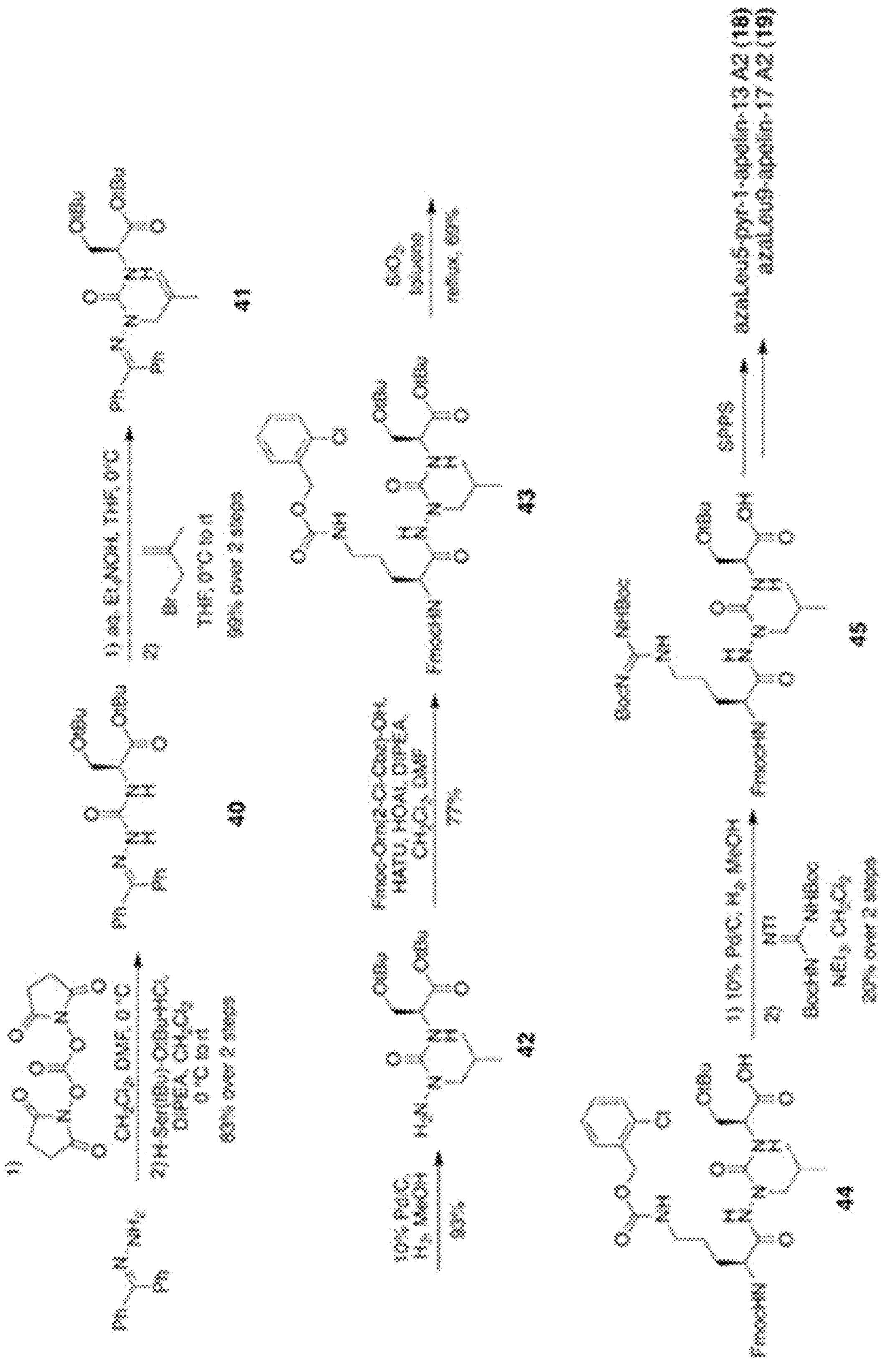
FIG. 8 is a synthetic scheme of dipeptide 45 for the preparation of aza-arginine apelin A2 peptides 18 and 19.

The synthesis of dipeptide 45 is outlined in FIG. 8. To prepare a synthetic azaLeu tripeptide, 40 was prepared by the sequential addition of disuccinimidyl carbonate, then a solution of H-Ser(tBu)-OtBu in DIPEA to benzophenone hydrazone. Semicarbazone alkylation was accomplished using tetraethylammonium hydroxide and 3-bromo-2-methylpropene to yield 41. Concomitant Pd-catalyzed hydrogenation and hydrogenolysis afforded semicarbazide 42, which was coupled to Fmoc-Orn(2-Cl-Cbz)-OH to generate azatripeptide 43. Chemoselective tert-butyl ester deprotection to free acid 44 was accomplished by addition of silica in refluxing toluene to protected azatripeptide 43. Subsequent 2-chloro-Cbz deprotection and guanidinylation of the resultant primary amine yielded azatripeptide 45, which was further employed to generate azaLeu-containing peptides 18 and 19.

Example 7

Synthesis and Characterization of Apelin Peptides

Compounds 23 and 24

Compounds 23 and 24 were prepared according to literature protocols described in the literatures. See, *Tetrahedron: Asymmetry,* 9, 4249-4252 (1998); WO 2011047215.

Fmoc-pBrPhe-2-Cl-Trt (6)

2-Chlorotrityl chloride resin (1.05 mmol) was transferred to a SPPS vessel, washed with $CH_2Cl_2$ (2×10 mL), DMF (2×10 mL), and finally suspended in DMF and bubbled under Ar gas for 10 minutes. Fmoc-p-bromo-L-phenylalanine (1.0 mmol) was suspended in dry $CH_2Cl_2$ (10 mL) with DIPEA (5.0 equivalents) and added to the swollen resin. This solution was bubbled under Ar gas for 2.5 h. The functionalized resin was washed considerably with $CH_2Cl_2$ (3×10 mL) and DMF (3×10 mL), and then unreacted sites were capped by bubbling with dry MeOH (5 mL) under Ar gas for 45 minutes. The resin was dried thoroughly under Ar, weighed and divided into 0.2 mmol portions, and stored under an Ar atmosphere at −20° C. "Trt" refers to trityl.

Fmoc-His(Trt)-Lys(Boc)-Gly-Pro-Nle-Aib-pBrPhe-2-Q-Trt (7)

Functionalized resin 6 was elongated by manual SPPS, introducing amino acids in the following order: Fmoc-Aib-OH, Fmoc-Nle-OH, Fmoc-Pro-OH, Fmoc-Gly-OH, Fmoc-Lys(Boc)-OH, and Fmoc-His(Trt)-OH. A small sample of the resin was cleaved and analysed by MALDI-TOF: Calculated for $C_{53}H_{68}BrN_{10}O_{10}$ 1083.4, found 1083.0 (M+H)+.

Synthesis of D-Leu Substituted A2 Peptides

D-Leu5-Pyr-1-Apelin-13 A2 (8)

Advanced intermediate 7 (0.1 mmol) was subjected to manual SPPS, introducing amino acids in the following order: Fmoc-Ser(tBu)-OH, Fmoc-D-Leu-OH, Fmoc-Arg(Pmc)-OH, Fmoc-Pro-OH, Fmoc-Arg(Pmc)-OH, and pyr-Glu-OH. A portion (0.05 mmol) of resin-bound peptide was cleaved and purified using a $C_{18}$ RP-HPLC analytical column (Method A), eluting at 20.6 min. The desired peptide was isolated as a white solid after lyophilization (11.3 mg, 14%). Monoisotopic MW calculated for $C_{69}H_{111}$ $BrN_{22}O_{16}$ 791.3860, found high resolution (FTICR-ESI-MS) 791.3846 $(M+2H)^{2}+$.

D-Leu9-Apelin-17 A2 (9)

Advanced intermediate 7 (0.1 mmol) was subjected to manual SPPS, introducing amino acids in the following order: Fmoc-Ser(tBu)-OH, Fmoc-D-Leu-OH, Fmoc-Arg(Pmc)-OH, Fmoc-Pro-OH, Fmoc-Arg(Pmc)-OH, Fmoc-Gln(Trt)-OH, Fmoc-Arg(Pmc)-OH, Fmoc-Arg(Pmc)-OH, Fmoc-Phe-OH, and Fmoc-Lys(Boc)-OH. A portion (0.05 mmol) of resin-bound peptide was cleaved and purified using a $C_{18}$ RP-HPLC analytical column (Method A), eluting at 11.2 min. The desired peptide was isolated as a white solid after lyophilization (9.9 mg, 9.1%). Monoisotopic MW calculated for $C_{96}H_{161}BrN_{34}O_{20}$ 547.2947, found high resolution (FTICR-ESI-MS) 547.2942 $(M+4H)^{4}+$.

Synthesis of α-Methyl Leucine A2 Peptides

Benzyl A-((5,)-2-((((9H-fluoren-9-yl)methoxy)carbonyl)amino)-5-((tert-butoxycarbonyl) amino) pentanoyl)-A-methyl-L-leucinate (20)

Fmoc-Orn(Boc)-OH (1.23 g, 2.70 mmol), HATU (1.03 g, 2.70 mmol), HOAt (4.5 mL [0.6 M solution in DMF], 2.70 mmol), and DIPEA (1.28 mL, 7.36 mmol) were dissolved in dry DMF (10 mL) and stirred for 5 minutes to preactivate the amino acid. A solution of N-Me-Leu-OBn p-TsOH (para-toluenesulfonic acid) salt (1.00 g, 2.45 mmol) and DIPEA (0.43 mL, 2.45 mmol) in dry $CH_2Cl_2$ (10 mL) was added and the reaction was stirred for 17 h at room temperature. The reaction was washed with 10% aqueous $NaHCO_3$ (20 mL), 10% aqueous citric acid (20 mL) and brine (20 mL). The organic layer was dried over $Na_2SO_4$, filtered, and concentrated in vacuo. The dipeptide was purified using flash chromatography (silica gel, 25% EtOAc in hexanes), obtaining 20 as a crunchy white solid (1.25 g, 76%). ($R_f$ 0.9 on $SiO_2$, 1:3 hexanes:EtOAc); $[\alpha]_D^{26}$ 500-17.4 (c 1.0 $CH_2Cl_2$); IR ($CH_2Cl_2$ cast) 3315, 3066, 3037, 2957, 2870, 1714, 1645, 1513, 1451, 1251, 1172 $cm^{-1}$; $^1H$ ($CDCl_3$, 500 MHz): δ 7.76 (d, J=7.5 Hz, 2H, Ar—H), 7.59 (d, J=7.5 Hz, 2H, Ar—H), 503 7.43-7.27 (m, 9H, Ar—H), 5.65 (d, J=8.5 Hz, 1H, Fmoc-NH), 5.35 (dd, J=10.8, 5.0 Hz, 1H, Leu-CHα), 5.19-5.06 (m, 2H, Bn-OCH2504), 4.68 (ddd, J=7.7, 7.7, 4.8 Hz, 1H, Orn-CHα), 4.51 (s, 1H, Boc-NH), 4.37 (ddd, J=10.6, 7.1, 7.1 Hz, 2H, Fmoc-$CH_2$), 4.21 (t, J=7.1 Hz, 1H, Fmoc-CH), 3.09-3.04 (m, 2H, Orn-$CH_2$δ), 2.93 (s, 3H, N—$CH_3$), 1.81-1.65 (m, 3H, 2×Leu-$CH_2$P, Orn-$CH_2$p), 1.56-1.46 (m, 4H, Orn-$CH_2$β, 2×Orn-$CH_2$γ, 507 Leu-$CH(CH_3)_2$), 1.44 (s, 9H, —$C(CH_3)_3$), 1.01-0.84 (m, 6H, —$CH(CH_3)_2$); $^{13}C$ (CDCl3508, 125 MHz): δ 172.6, 171.3, 156.0, 155.9, 143.9, 143.8, 141.3, 141.3, 135.4, 128.7, 128.5, 128.4, 127.7, 127.1, 127.1, 125.2, 120.0, 79.1, 510 67.1, 67.0, 54.9, 50.7, 47.2, 40.1, 36.8, 31.1, 30.0, 28.5, 25.4, 24.9, 23.2, 21.4; HRMS (ES) Calculated for $C_{39}H_{50}N_3O_7$ 672.3643, found 672.3642 $(M+H)^{+}$511.

Benzyl(11S,14S,E)-11-((((9H-fluoren-9-yl)methoxy) carbonyl)amino)-6-((tert-butoxycarbonyl)amino)-14-isobutyl-2,2,13-trimethyl-4,12-dioxo-3-oxa-5,7,13-triazapentadec-5-en-15-oate (21)

The guanidinylation reaction was adapted from a literature procedure.[58] TFA (5 mL) was added to a solution of dipeptide 20 (0.701 g, 1.04 mmol) in dry $CH_2Cl_2$ (10 mL) and stirred for 1 h. The reaction was concentrated in vacuo, using diethyl ether co-evaporations to remove residual TFA. The yellow oil was resuspended in dry $CH_2Cl_2$ (20 mL) and 1,3-di-Boc-2-(trifluoromethylsulfonyl)guanidine (0.449 g, 1.15 mmol) and triethylamine (0.32 mL, 2.30 mmol) were added and stirred for 80 minutes. The reaction was washed with 2 N aqueous sodium bisulfate (10 mL) and 10% $NaHCO_3$ (10 mL), dried over $Na_2SO_4$, filtered, and concentrated in vacuo. The dipeptide was purified using flash chromatography (silica gel, 20% EtOAc in hexanes), obtaining 21 as a crunchy white solid (0.820 g, 97%). ($R_f$ 0.5 on $SiO_2$, 3:1 hexanes:EtOAc); $[\alpha]_D^{26}$ −12.5 (c 1.21 $CHCl_3$); IR ($CHCl_3$ cast) 3331, 2959, 2871, 1721, 1640, 1451, 1415, 1330, 1156, 1134 $cm^{-1}$; $^1H$ ($CDCl_3$, 500 MHz): δ 8.29 (t, J=5.4 Hz, 1H, Arg-N$\underline{H}\varepsilon$), 7.76 (d, J=7.6 Hz, 2H, Ar—$\underline{H}$), 7.60 (d, J=7.6 Hz, 2H, Ar—$\underline{H}$), 7.43-7.27 (m, 9H, Ar—$\underline{H}$), 5.68 (d, J=8.5 Hz, 1H, Fmoc-N$\underline{H}$), 5.37-5.28 (m, 1H, Leu-C$\underline{H}\alpha$), 5.23-5.05 (m, 2H, —OC$\underline{H}_2$Ph), 4.67 (td, J=8.1, 4.3 Hz, 1H, Arg-C$\underline{H}\alpha$), 4.44-4.31 (m, 2H, Fmoc-C$\underline{H}_2$), 4.21 (t, J=6.9 Hz, 1H, Fmoc-C$\underline{H}$), 3.36 (ddd, J=7.4, 5.0, 3.2 Hz, 2H, Arg-C$\underline{H}_2\delta$), 2.93 (s, 3H, N—C$\underline{H}_3$), 1.82-1.75 (m, 1H, Leu-C$\underline{H}_2\beta$), 1.75-1.66 (m, 2H, Leu-C$\underline{H}_2\beta$, Arg-C$\underline{H}_2\beta$), 1.63-1.55 (m, 3H, Arg-C$\underline{H}_2\beta$, 2×Arg-C$\underline{H}_2\gamma$) 1.49 (m, 10H, Leu-C$\underline{H}(CH_3)_2$, —C(C$\underline{H}_3)_3$), 1.48 (s, 9H, —C(C$\underline{H}_3)_3$), 0.93 (d, J=6.6 Hz, 3H, Leu-CH(C$\underline{H}_3)_2$), 0.90 (d, J=6.5 Hz, 3H, Leu-CH(C$\underline{H}_3)_2$); $^{13}C$ ($CDCl_3$, 125 MHz): δ 172.5, 171.2, 163.6, 156.2, 156.0, 153.3, 143.9, 143.8, 141.3, 141.3, 135.4, 128.7, 128.6, 128.4, 127.7, 127.1, 127.1, 125.2, 125.2, 120.0, 83.1, 79.2, 67.1, 67.0, 54.9, 50.8, 47.2, 40.3, 36.8, 31.2, 29.9, 28.3, 28.1, 27.9, 27.9, 24.9, 23.2, 21.4; HRMS (ES) Calculated for $C_{45}H_{60}N_5O_9$ 814.4386, found 814.4378 (M+H)$^+$.

(11S,14S,E)-11-((((9H-fluoren-9-yl)methoxy)carbonyl)amino)-6-((tert-butoxycarbonyl)amino)-14-isobutyl-2,2,13-trimethyl-4,12-dioxo-3-oxa-5,7,13-triazapentadec-5-en-15-oic Acid (22)

A solution of 21 (0.501 g, 0.62 mmol) was dissolved in methanol (50 mL) and had 10% Pd/C (20 mg) added. The suspension was stirred under hydrogen gas for 22 h, filtered through a pad of Celite, and concentrated in vacuo. The crude residue was purified using flash chromatography (silica gel, 5% MeOH in $CH_2Cl_2$, 0.1% AcOH), yielding 22 as a white solid (0.378 g, 85%). ($R_f$ 0.2 on $SiO_2$, 1% AcOH in EtOAc); $[\alpha]_D^{26}$ −2.8 (c 1.0 $CH_2Cl_2$); IR ($CH_2Cl_2$ cast) 3326, 3140, 3066, 2959, 2872, 1721, 1641, 1618, 1451, 1415, 1331, 1253, 1136 $cm^{-1}$; $^1H$ ($CDCl_3$, 500 MHz): δ 8.48 (s, 1H, Arg-N$\underline{H}\varepsilon$), 7.76 (d, J=7.5 Hz, 2H, Ar—$\underline{H}$), 7.61 (d, J=7.5 Hz, 2H, Ar—$\underline{H}$), 7.40 (t, J=7.5 Hz, 2H, Ar—$\underline{H}$), 7.32 (tdd, J=7.5, 3.4, 1.2 Hz, 2H, Ar—$\underline{H}$), 6.05 (d, J=7.6 Hz, 1H, Fmoc-N—$\underline{H}$), 5.37 (dd, J=10.7, 5.1 Hz, 1H, Leu-C$\underline{H}\alpha$), 4.80 (dd, J=5.4, 5.3 Hz, 1H, Arg-C$\underline{H}\alpha$), 4.38 (dd, J=10.6, 7.2 Hz, 2H, Fmoc-C$\underline{H}_2$), 4.21 (t, J=7.1 Hz, 1H, Fmoc-C$\underline{H}$), 3.55-3.45 (m, 1H, Arg-C$\underline{H}_2\delta$), 3.14-3.05 (m, 1H, Arg-C$\underline{H}_2\delta$), 2.98 (s, 3H, N—C$\underline{H}_3$), 1.92-1.56 (m, 6H, 2×Leu-$CH_2\beta$, 2×Arg-$CH_2\beta$, 2×Arg-C$\underline{H}_2\gamma$), 1.52 (s, 9H, —C$(CH_3)_3$), 1.49 (m, 10H, Leu-C$\underline{H}(CH_3)_2$, —C(C$\underline{H}_3)_3$), 0.96 (d, J=6.6 Hz, 3H, Leu-CH(C$\underline{H}_3)_2$), 0.93 (d, J=6.5 Hz, 3H, Leu-CH(C$\underline{H}_3)_2$); $^{13}C$ ($CDCl_3$, 125 MHz): δ 172.3, 172.1, 162.8, 156.3, 155.7, 153.2, 144.9, 143.8, 141.4, 141.3, 127.7, 127.7, 127.1, 127.1, 125.2, 125.2, 120.0, 119.9, 83.1, 80.6, 66.9, 54.7, 51.1, 47.3, 40.6, 36.1, 30.7, 28.4, 28.1, 28.1, 24.8, 23.2, 21.4; HRMS (ES) Calculated for $C_{38}H_{54}N_5O_9$ 724.3916, found 724.3924 (M+H)$^+$.

N-MeLeu5-Pyr-1-Apelm-13 A2 (10)

Advanced intermediate 7 (0.1 mmol) was subjected to manual SPPS, introducing amino acids in the following order: Fmoc-Ser(tBu)-OH, 22, Fmoc-Pro-OH, Fmoc-Arg (Pmc)-OH. The resin was split into half, and Fmoc-SPPS was continued on 0.1 mmol scale, coupling pyr-Glu-OH. No endcapping was performed following addition of 22. A portion (0.05 mmol) of resin-bound peptide was cleaved as previously described and purified using a C18 RP-HPLC analytical column (Method A), eluting at 11.2 min. The desired peptide was isolated as a white solid after lyophilization (6.0 mg, 7%). Monoisotopic MW calculated for $C_{70}H_{114}BrN_{22}O_{16}$ 532.5983, found high resolution (FTICR-ESI-MS) 532.5972 (M+3H)$^{3+}$.

N-MeLeu9-Apelin-17 A2 (11)

The remaining 0.1 mmol carried over from the synthesis of 10 was coupled with: Fmoc-Gln(Trt)-OH, Fmoc-Arg (Pmc)-OH, Fmoc-Arg(Pmc)-OH, Fmoc-Phe-OH, and Fmoc-Lys(Boc)-OH. No endcapping was performed following addition of 22. A portion (0.05 mmol) of resin-bound peptide was cleaved as previously described and purified using a C18 RP-HPLC analytical column (Method A), eluting at 11.3 min. The desired peptide was isolated as a white solid after lyophilization (23.8 mg, 22%). Monoisotopic MW calculated for $C_{97}H_{163}BrN_{34}O_{20}$ 550.7986, found high resolution (FTICR-ESI-MS) 550.7983 (M+4H)$^{4+}$.

Synthesis of α-Methyl Arginine A2 Peptides

1-Azido-3-Iodopropane (24)

Compound 24 was prepared according to literature procedures.[43] A solution of 1-chloro-3-iodopropane (2.63 mL, 24.5 mmol) and sodium azide (1.91 g, 29.4 mmol) in dry DMF (60 mL) was stirred at room temperature for 24 h. The reaction was diluted by the addition of water (100 mL) and diethyl ether washes (2×100 mL) were used to extract organic components. The diethyl ether fractions were dried over $Na_2SO_4$, filtered and concentrated in vacuo until a small volume (~10 mL) of ether remained. The reaction was diluted in acetone (60 mL) and following the addition of sodium iodide (5.50 g, 36.7 mmol), the reaction was heated at 60° C. for 24 h. The solution was concentrated in vacuo until a small volume (~10 mL) remained, then diluted with diethyl ether (100 mL) and washed with $H_2O$ (2×100 mL). The organic layer was dried over $Na_2SO_4$, vacuum filtered through a small plug of alumina, and concentrated in vacuo, obtaining the desired product as a light yellow oil (3.91 g, 76%). IR ($CH_2Cl_2$ cast) 2927, 2869, 2098, 1449, 1428, 1347, 1290, 1224, 1173 $cm^{-1}$; $^1H$ ($CDCl_3$, 500 MHz): δ 3.44 (t, J=6.4 Hz, 2H, —$CH_2N_3$), 3.25 (t, J=6.6 Hz, 2H, —$CH_2I$), 2.04 (app pentet, J=6.5 Hz, 2H, —$CH_2$—); $^{13}C$ ($CDCl_3$, 125 MHz): δ 51.5, 32.4, 2.3.

(2S)-2-(3'-Azidopropyl)-2-Methyl-Glycine-Ni(II)-(S)-BPB (25)

Complex 25 was prepared according to literature procedure.[43] Nickel complex 23 (6.49 g, 12.7 mmol) and potassium tert-butoxide (2.13 g, 19.0 mmol) were added to an RBF and dissolved in dry DMF (50 mL) at 0° C. under an Ar atmosphere. This solution was stirred for 3 minutes, followed by the addition of a solution of 24 (5.01 g, 19.0 mmol) in dry DMF (10 mL). The reaction was stirred at 0° C. for 45 minutes, then warmed to room temperature for 75 minutes. 5% aqueous acetic acid (200 mL) was added to quench the reaction, followed by extraction with $CH_2Cl_2$ (3×75 mL). Pooled organic layers were washed with brine (2×75 mL), dried over $Na_2SO_4$, filtered and concentrated in vacuo. The desired diastereomer was purified by flash chromatography (silica gel; 2.5% MeOH in EtOAc), yielding 25 as a red solid (5.18 g, 69%). Crystals of 25 were obtained after dissolution in minimal $CH_2Cl_2$, dilution with hexanes and slow evaporation. ($R_f$ 0.6 on $SiO_2$, 9:1 EtOAc:MeOH); $[\alpha]_D^{26}$ 1853.4 (c 1.0 $CH_2Cl_2$); IR ($CH_2Cl_2$ cast) 3060, 2937, 2869, 2097, 1673, 1639, 1574, 1439, 1359, 1253, 1165 $cm^{-1}$;

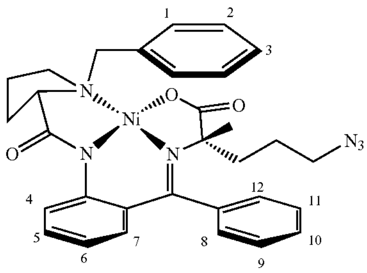

$^1H$ ($CDCl_3$, 500 MHz): δ 8.12-8.07 (m, 2H, Ar—$H_1$), 8.05 (dd, J=8.7, 0.9 Hz, 1H, Ar—$H_4$), 7.55-7.48 (m, 2H, Ar—$H_8$, Ar—$H_9$), 7.47-7.41 (m, 3H, Ar—$H_2$, Ar—$H_{11}$), 7.35-7.28 (m, 2H, ArH$_3$, Ar—$H_{10}$), 7.16 (ddd, J=8.5, 5.8, 2.7 Hz, 1H, Ar—$H_5$), 7.08 (dt, J=7.6, 1.3 Hz, 1H Ar—$H_{12}$), 6.69-6.62 (m, 2H, Ar—$H_6$, Ar—$H_7$), 4.50 (d, J=12.7 Hz, 1H, Ph-C$H_2$—N), 3.70 (dd, J=18.7, 11.8 Hz, 2H, Ph-C$H_2$—N, Pro-C$H_2$δ), 3.51-3.42 (m, 2H, Pro-CHα, —$CH_2N_3$), 3.32-3.20 (m, 2H, —$CH_2N_3$, Pro-C$H_2$γ), 2.71 (dddd, J=12.8, 7.1, 5.8, 2.6 Hz, 1H, Pro-C$H_2$β, 2.58-2.43 (m, 2H, Pro-C$H_2$β, —C$H_2CH_2N_3$), 2.26-2.04 (m, 3H, —$CH_2CH_2N_3$, Pro-C$H_2$γ, Pro-C$H_2$δ, 1.86 (ddd, J=13.8, 12.4, 4.2 Hz, 1H, —$CH_2CH_2CH_2N_3$), 1.76 (ddd, J=13.7, 12.4, 4.6 Hz, 1H, —$CH_2CH_2CH_2N_3$), 1.28 (s, 3H, —$CH_3$); $^{13}C$ ($CDCl_3$, 125 MHz): δ 182.0, 180.6, 172.8, 141.6, 136.4, 133.4, 133.4, 131.8, 131.7, 130.2, 129.6, 129.1, 129 0.0, 128.5, 128 0.1, 127.3, 127.1, 124.0, 120.8, 77 0.4, 70.0, 63.5, 57.2, 51.3, 37.5, 30.7, 29.4, 25.5, 23.4; HRMS (ES) Calculated for $C_{31}H_{32}N_6NaNiO_3$ 617.1782, found 617.1785 $(M+Na)^+$.

(S)-2-((((9H-fluoren-9-yl)methoxy)carbonyl)amino)-5-azido-2-methylpentanoic Acid (26)

A solution of 3N HCl:MeOH (1:1, 40 mL) was heated to 70° C. and had 25 (2.60 g, 4.37 mmol) dissolved in MeOH (10 mL) added dropwise over 5 minutes. The reaction mixture was stirred for 50 minutes at 70° C., turning from dark red to green as the reaction proceeded. The reaction was cooled to room temperature, concentrated in vacuo and resuspended in 10% aqueous sodium carbonate (20 mL). EDTA disodium salt (3.25 g, 8.73 mmol) was added and stirred for 0.5 h at room temperature. The reaction was cooled to 0° C. and had a solution of Fmoc-OSu (1.62 g, 4.80 mmol) dissolved in acetone (20 mL) added to it. This reaction was slowly warmed to room temperature and stirred for 16 h. The following day, the reaction was diluted with EtOAc (50 mL) and washed with 1 N HCl (3×20 mL). The organic layer was dried over $MgSO_4$, filtered, and concentrated in vacuo. The product was purified by flash chromatography (silica gel, 1-5% MeOH in $CH_2Cl_2$ gradient), yielding 26 as a white solid (1.64 g, 95%). ($R_f$ 0.4 on $SiO_2$, 9:1 EtOAc:MeOH); $^1H$ ($CDCl_3$, 500 MHz): δ 7.77 (d, J=7.5 Hz, 2H, Ar—H), 7.58 (d, J=7.5 Hz, 2H, Ar—H), 7.40 (td, J=7.4, 3.1 Hz, 2H, Ar—H), 7.32 (tdd, J=7.4, 2.6, 1.1 Hz, 2H, Ar—H), 5.57 (br s, 1H, Fmoc-NH), 4.48-4.36 (m, 2H, Fmoc-C$H_2$), 4.21 (t, J=6.2 Hz, 1H, Fmoc-CH), 3.32-3.19 (m, 2H, —$CH_2N_3$), 2.28-2.17 (m, 1H, Orn-C$H_2$γ), 2.02-1.90 (m, 1H, Orn-C$H_2$γ), 1.60 (br s, 3H, —$CH_3$), 1.50-1.39 (m, 2H, Orn-C$H_2$β); $^{13}C$ ($CDCl_3$, 125 MHz): δ 170.1, 153.9, 143.8, 141.4, 127.7, 127.1, 125.0, 120.0, 66.6, 51.1, 47.2, 34.0, 33.4, 23.7, 23.5; HRMS (ES) Calculated for $C_{21}H_{21}N_4O_4$ 393.1568, found 393.1566 $(M-H)^-$.

Methyl ((S)-2-((((9H-fluoren-9-yl)methoxy)carbonyl)amino)-5-azido-2-methyl-pentanoyl)-L-leucinate (27)

Compound 26 (1.61 g, 4.09 mmol), HATU (1.55 g, 4.09 mmol), HOAt (0.68 mL [0.6 M solution in DMF], 0.41 mmol), and DIPEA (2.85 mL, 16.4 mmol) were dissolved in dry DMF (25 mL) and stirred for 5 minutes to preactivate the amino acid. A solution of H-Leu-OMe.HCl (0.780 g, 4.29 mmol) in dry $CH_2Cl_2$ (25 mL) was added and the reaction was stirred for 16 h at room temperature. The reaction was concentrated in vacuo, resuspended in EtOAc (50 mL), and washed with 10% citric acid, water, and brine (50 mL). The organic layer was dried over $Na_2SO_4$, filtered, and concentrated in vacuo. Crude 27 was purified using flash chromatography (silica gel, 33% EtOAc in hexanes), obtaining the desired dipeptide as a yellow oil (1.22 g, 57%). ($R_f$ 0.5 on $SiO_2$, 2:1 hexane:EtOAc); $[\alpha]_D^{26}$−1.2 (c 1.0 $CHCl_3$); IR ($CHCl_3$ cast) 3342, 2956, 2872, 2097, 1731, 1664, 1495, 1450, 1249, 1089 $cm^{-1}$; $^1H$($CDCl_3$, 500 MHz): δ7.76 (dd, J=7.4, 1.0 Hz, 2H, Ar—H), 7.59 (ddd, J=7.5, 4.0, 1.0 Hz, 2H, Ar—H), 7.44-7.35 (m, 2H, Ar—H), 7.32 (dddd, J=7.5, 7.5, 2.2, 1.2 Hz, 2H, Ar—H), 6.38 (br s, 1H, Leu-NH), 5.83 (br s, 1H, Fmoc-NH), 4.60 (ddd, J=8.6, 8.0, 4.7 Hz, 1H, Leu-CHα), 4.49-4.35 (m, 2H, Fmoc-C$H_2$), 4.20 (t, J=6.6 Hz, 1H, Fmoc-CH), 3.72 (s, 3H, —$OCH_3$), 3.34-3.18 (m, 2H, Arg-C$H_2$δ), 2.47-2.23 (m, 1H, Arg-C$H_2$β), 1.84-1.76 (m, 1H, Arg-C$H_2$β), 1.70-1.40 (m, 8H, Arg-C$H_3$, 2×Arg-C$H_2$γ, 2×Leu-C$H_2$β, —$CH(CH_3)_2$), 0.93 (m, 6H, —$CH(CH_3)_2$); $^{13}C$ ($CDCl_3$, 125 MHz): δ 173.4, 173.1, 154.6, 143.9, 143.9, 141.4, 127.7, 127.1, 127.1, 125.0, 120.0, 66.5, 59.4, 52.4, 51.2, 51.1, 47.3, 41.3, 33.9, 25.0, 24.0, 23.5, 22.8, 21.9; HRMS (ES) Calculated for $C_{28}H_{35}N_5NaO_5$ 544.2530, found 544.2527 (M+Na)+.

methyl ((S)-2-((((9H-fluoren-9-yl)methoxy)carbonyl)amino)-5-((Z)-2,3-bis(tert-butoxycarbonyl)quanidino)-2-methylpentanoyl)-L-leucinate (28)

The guanidinylation reaction was adapted from a literature procedure.[58] Dipeptide 27 (1.16 g, 2.23 mmol) was dissolved in MeOH (50 mL) and had 10% Pd/C (20 mg) added. The suspension was stirred under hydrogen gas for 2 h, filtered through a pad of Celite, and concentrated in vacuo. The crude residue was suspended in $CH_2Cl_2$ (30 mL) and 1,3-di-Boc-2-(trifluoromethylsulfonyl)guanidine (0.961 g, 2.45 mmol) and triethylamine (0.69 mL, 4.91 mmol) were added. This reaction was stirred at room temperature under Ar for 18 h, concentrated in vacuo, and purified using flash chromatography (silica gel, 35% EtOAc in hexanes), yielding 28 as a white solid (1.08 g, 66%). ($R_f$ 0.4 on $SiO_2$, 3:1 hexane:EtOAc); $[\alpha]_D^{26}$ 3.2 (c 1.0 $CHCl_3$); IR ($CHCl_3$ cast) 3332, 2959, 1723, 1644, 1619, 1495, 1451, 1369, 1332, 1234, 1155, 1135, 1057 $cm^{-1}$; $^1H$ ($CDCl_3$, 500 MHz): δ 8.28 (s, 1H, Arg-N$H_\varepsilon$), 7.76 (dt, J=7.5, 0.9 Hz, 2H, Ar—H), 7.60 (ddq, J=7.7, 5.0, 1.0 Hz, 2H, Ar—H), 7.46-7.36 (m, 2H, Ar—H), 7.32 (dddd, J=7.4, 7.4, 3.8, 1.2 Hz, 2H, Ar—H), 6.39 (br s, 1H, Leu-NH), 5.82 (br s, 1H, Fmoc-NH), 4.62-4.53 (m, 1H, Leu-CHα), 4.46-4.36 (m, 2H, Fmoc-$CH_2$), 4.21 (t, J=6.7 Hz, 1H, Fmoc$CH_2$), 3.71 (s, 3H, —$OCH_3$), 3.44-3.32 (m, 2H, Arg-$CH_2$δ), 2.35-2.19 (m, 1H, Arg-$CH_2$β), 1.82-1.71 (m, 1H, Arg-$CH_2$β), 1.70-1.51 (m, 8H, Arg-$CH_3$, 2×Arg-$CH_2$γ, 2×Leu-$CH_2$β, —$CH(CH_3)_2$), 1.49 (s, 9H, —$C(CH_3)_3$), 1.48 (s, 9H, —$C(CH_3)_3$), 0.93 (d, J=6.2 Hz, 6H, —$CH(CH_3)_2$); $^{13}C$ ($CDCl_3$, 125 MHz): δ 173.5, 173.2, 163.5, 156.2, 153.2, 143.9, 143.9, 141.3, 127.7, 127.1, 127.1, 125.0, 120.0, 83.1, 79.3, 66.5, 59.5, 52.4, 51.1, 47.3, 41.2, 40.6, 28.3, 28.1, 25.0, 24.0, 23.7, 22.8, 21.8; HRMS (ES) Calculated for $C_{39}H_{56}N_5O_9$ 738.4073, found 738.4069 $(M+H)^+$.

((S)-2-((((9H-fluoren-9-yl)methoxy)carbonyl)amino)-5-((Z)-2,3-bis(tert-butoxy-carbonyl)quanidino)-2-methylpentanoyl)-L-leucine (29)

Methyl ester deprotection conditions were adapted from a literature protocol.[44] Dipeptide 28 (1.06 g, 1.44 mmol) was dissolved in aqueous 2-propanol (70% 2-propanol in water, 50 mL) and had $CaCl_2.2H_2O$ (5.88 g) added to generate a 0.8 M $Ca^{2+}$ solution. Sodium hydroxide (0.115 g, 2.87 mmol) was added and the reaction was stirred for 3.5 h. Acetic acid (0.164 mL, 2.87 mmol) was added to neutralize residual base, and the reaction was concentrated in vacuo. The crude residue was dissolved in minimal MeOH and the dipeptide was precipitated by the addition of $H_2O$ and collected by vacuum filtration, yielding 29 as a white solid (0.982 g, 94%). ($R_f$ 0.05 on $SiO_2$, 1:1 hexane:EtOAc); $[\alpha]_D^{26}$−6.0 (c 1.0 MeOH); IR (MeOH cast) 3347, 2957, 1722, 1641, 1450, 1416, 1368, 1331, 1135 $cm^{-1}$; $^1H$ ($CD_3OD$, 500 MHz): δ 7.89 (s, 1H, Arg-$NH_\varepsilon$), 7.78 (dt, J=7.6, 0.9 Hz, 2H, Ar—H), 7.70-7.64 (m, 2H, Ar—H), 7.41-7.34 (m, 2H, Ar—H), 7.30 (td, J=7.4, 1.1 Hz, 3H, Ar—H), 4.38 (d, J=6.6 Hz, 2H, Fmoc-$CH_2$), 4.25-4.19 (m, 2H, Fmoc-CH, LeuCHα), 3.33-3.27 (m, 2H, Arg-$CH_2$δ), 2.03-1.94 (m, 1H, Arg-$CH_2$β), 1.84-1.75 (m, 1H, Arg-$CH_2$β), 1.68-1.52 (m, 4H, —$CH(CH_3)_2$, 2×Leu-$CH_2$β, Arg-$CH_2$γ), 1.50 (d, J=3.7 Hz, 10H, —$C(CH_3)_3$, Arg-$CH_2$γ), 1.44 (s, 9H, —$C(CH_3)_3$), 1.40 (s, 3H, Arg-$CH_3$), 0.88 (d, J=6.4 Hz, 3H, —$CH(CH_3)_2$, 0.87 (d, J=6.4 Hz, 3H, —$CH(CH_3)_2$; $^{13}C$ ($CDCl_3$, 125 MHz): δ 176.3, 172.4, 164.6, 157.5, 154.1, 145.3, 142.7, 128.9, 128.2, 126.2, 121.0, 84.5, 80.4, 79.5, 67.8, 60.6, 49.6, 49.3, 41.8, 28.6, 28.3, 26.1, 24.7, 23.7, 22.1; HRMS (ES) Calculated for $C_{38}H_{54}N_5O_9$ 724.3916, found 724.3913 (M+H)+.

α-MeArg4-pyr-1-apelin-13 A2 (12)

Advanced intermediate 7 (0.2 mmol) was subjected to manual SPPS (solid phase peptide synthesis), introducing amino acids in the following order: Fmoc-Ser(tBu)-OH, 29, Fmoc-Pro-OH, Fmoc-Arg(Pmc)-OH. The resin was split into half, and Fmoc-SPPS was continued on 0.1 mmol scale, coupling pyr-Glu-OH. No endcapping was performed following addition of 29. A portion (0.05 mmol) of resin-bound peptide was cleaved as previously described and purified using a C18 RP-HPLC analytical column (Method A), eluting at 13.4 min. The desired peptide was isolated as a white solid after lyophilization (8.5 mg, 11%). Monoisotopic MW calculated for $C_{70}H_{114}BrN_{22}O_{16}$ 532.5983, found high resolution (FTICR-ESI-MS) 532.5973 $(M+3H)^{3+}$.

α-MeArg8-apelin-17 A2 (13)

The remaining 0.1 mmol carried over from the synthesis of 12 was coupled with: FmocGln(Trt)-OH, Fmoc-Arg(Pmc)-OH, Fmoc-Arg(Pmc)-OH, Fmoc-Phe-OH, and Fmoc-Lys(Boc)-OH. No endcapping was performed following addition of 29. A portion (0.05 mmol) of resin-bound peptide was cleaved as previously described and purified using a C18 RP-HPLC analytical column (Method A), eluting at 13.0 min. The desired peptide was isolated as a white solid after lyophilization (12.5 mg, 11%). Monoisotopic MW calculated for $C_{97}H_{163}BrN_{34}O_{20}$ 550.7986, found high resolution (FTICR-ESI-MS) 550.7974 $(M+4H)^{4+}$.

Synthesis of α-methyl Leucine A2 Peptides (2S)-2-(2'-methylpropyl)-2-methyl-qlycine-Ni(II)-(S)-BPB (30)

Alkylation conditions were adapted from literature protocol.[42] Nickel complex 23 (3.20 g, 6.25 mmol) and potassium tert-butoxide (1.05 g, 9.37 mmol) were added to an RBF and dissolved in dry DMF (25 mL) at 0° C. under an Ar atmosphere. This solution was stirred for 3 minutes, followed by the addition of 1-iodo-2-methylpropane (2.16 mL, 18.7 mmol). The reaction was stirred at 0° C. for 30 minutes, then warmed to room temperature for an additional 75 minutes. 5% aqueous acetic acid (100 mL) was added to quench the reaction, followed by extraction with $CH_2Cl_2$ (3×75 mL). The pooled organic layers were washed with brine (2×75 mL), dried over $Na_2SO_4$, filtered and concentrated in vacuo. The desired diastereomer was purified by flash chromatography (silica gel; 2.5% MeOH in EtOAc), yielding 30 as a red solid (2.43 g, 69%). Crystals of 30 were obtained after dissolution in minimal $CH_2Cl_2$, dilution with hexanes and slowevaporation. ($R_f$ 0.6 on $SiO_2$, 9:1 EtOAc:MeOH); $[\alpha]_D^{26}$ 1683.7 (c 1.0 $CHCl_3$); IR ($CHCl_3$ cast) 2959, 2870, 1668, 1639, 1535, 1439, 1360, 1253, 1170 $cm^{-1}$;

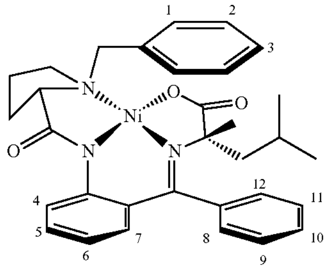

$^1H$ ($CDCl_3$, 500 MHz): δ 8.12-8.06 (m, 3H Ar—$H_1$, Ar—H4), 7.51-7.43 (m, 2H, Ar—$H_8$, Ar—$H_9$), 7.42-7.36 (m, 3H, Ar—$H_2$, Ar—$H_{11}$), 7.34-7.22 (m, 2H, Ar—$H_3$, Ar—$H_{10}$), 7.12 (ddd, J=8.6, 6.7, 1.9 Hz, 1H, Ar—$H_5$), 7.06-7.00 (m, 1H, Ar—$H_{12}$), 6.64-6.53 (m, 2H, Ar—$H_6$, Ar—$H_7$), 4.48 (d, J=12.7 Hz, 1H, Ph-$CH_2$—N), 3.74-3.64 (m, 2H, Ph-$CH_2$—N, Pro-$CH_2$δ), 3.45 (dd, J=10.6, 6.1 Hz, 1H, Pro-CHα), 3.26-3.10 (m, 1H, Pro-$CH_2$γ), 2.74-2.65 (m, 1H, Pro-$CH_2$β), 2.56-2.37 (m, 2H, Pro-$CH_2$β, Leu-CHy), 2.13-2.00 (m, 2H, Pro-$CH_2$γ, Pro-$CH_2$δ), 1.73-1.60 (m, 2H, Leu-$CH_2$β), 1.27 (d, J=6.6 Hz, 3H, Leu-$CH_3$O), 1.22 (s, 3H, Leu-$CH_3$β), 1.14 (d, J=6.7 Hz, 3H, Leu-$CH_3$δ); $^{13}C$ ($CDCl_3$, 125 MHz): δ 182.9, 180.6, 172.3, 141.7, 136.8, 133.6, 133.5, 131.7, 131.6, 130.5, 129.4, 129.0, 128 0.9, 128 0.4, 127.8, 126.9, 123.8, 120.6, 77.5, 70.2, 63.6, 57.1, 48.5, 30.7, 30.7, 25 0.6, 24.5, 23.3, 23.3; HRMS (ES) Calculated for $C_{32}H_{36}N_3NiO_3$ 568.2105, found 568.2100 $(M+H)^+$.

(S)-2-((((9H-fluoren-9-yl)methoxy)carbonyl)amino)-2,4-dimethylpentanoic Acid (31)

A solution of 3N HCl:MeOH (1:1, 10 mL) was heated to 70° C. and had 30 (2.36 g, 4.16 mmol) dissolved in MeOH (5 mL) added dropwise over 5 minutes. The reaction mixture was stirred for 40 minutes, turning from dark red to green as the reaction proceeded. The reaction was cooled to room temperature, concentrated in vacuo and resuspended in 10% aqueous sodium carbonate (25 mL). EDTA disodium salt (3.09 g, 8.31 mmol) was added and stirred for 0.5 h at room temperature. The reaction was cooled to 0° C. and had a solution of Fmoc-OSu (1.54 g, 4.57 mmol) dissolved in acetone (25 mL) added to it. This reaction was slowly warmed to room temperature and stirred for 22 h. The following day, the reaction was diluted with EtOAc (50 mL) and washed with 1 N HCl (3×50 mL). The organic layer was dried over $MgSO_4$, filtered, and concentrated in vacuo. The product was purified by flash chromatography (silica gel, 1-5% MeOH in $CH_2Cl_2$ gradient), yielding 31 as a white solid (1.45 g, 95%). ($R_f$ 0.35 on $SiO_2$, 7.5% MeOH in $CH_2Cl_2$); $^1$H ($CDCl_3$, 500 MHz): δ 7.80-7.74 (m, 2H, Ar—H), 7.64-7.57 (m, 2H, ArH), 7.43-7.38 (m, 2H, Ar—H), 7.37-7.29 (m, 2H, Ar—H), 5.92 (br s, 1H, N—H), 4.46-4.33 (m, 2H, Fmoc-$CH_2$), 4.32 (t, 1H, J=6.0 Hz Fmoc-CH), 2.26-2.19 (m, 1H, Leu-$CH_2$β), 1.83-1.73 (m, 1H, Leu-$CH_2$β), 1.70-1.55 (m, 4H, Leu-CHγ, Leu-$CH_3$β), 0.96-0.82 (m, 6H, 2×Leu$CH_3$δ); $^{13}$C ($CDCl_3$, 125 MHz): δ 179.4, 155.2, 143.9, 141.6, 127.8, 127.1, 124.8, 120.0, 65.1, 47.3, 24.9, 24.7, 23.8, 23.0; HRMS (ES) Calculated for $C_{22}H_{24}NO_4$ 366.1711, found 366.1706 $(M-H)^-$.

methyl N—((S)-2-((((9H-fluoren-9-yl)methoxy) carbonyl)amino)-2,4-dimethyl-pentanoyl)-O-(tert-butyl)-L-serinate (32)

Amino acid 31 (1.53 g, 4.16 mmol), HATU (1.58 g, 4.16 mmol), HOAt (0.69 mL [0.6 M solution in DMF], 0.42 mmol), and DIPEA (2.90 mL, 16.6 mmol) were dissolved in dry DMF (25 mL) and stirred for 5 minutes to preactivate the amino acid. A solution of H-Ser(tBu)-OMe.HCl (0.925 g, 4.37 mmol) in dry $CH_2Cl_2$ (25 mL) was added and the reaction was stirred for 20 h at room temperature. The reaction was concentrated in vacuo, resuspended in EtOAc (50 mL), and washed with 10% citric acid, water, and brine (50 mL). The organic layer was dried over $Na_2SO_4$, filtered, and concentrated in vacuo. Crude 32 was purified using flash chromatography (silica gel, 25% EtOAc in hexanes), obtaining the desired product as a whitesolid (0.872 g, 40%). ($R_f$ 0.2 on $SiO_2$, 3:1 hexanes:EtOAc); $[\alpha]_D^{26}$ 20.4 (c 1.0 $CHCl_3$); IR ($CHCl_3$ cast) 3440, 3384, 2973, 2956, 2872, 1730, 1669, 1493, 1364, 1241, 1099 $cm^{-1}$; $_1$H ($CDCl_3$, 500 MHz): δ 7.76 (dd, J=7.6, 0.9 Hz, 2H, Ar—H), 7.64-7.58 (m, 2H, Ar—H), 7.39 (ddd, J=6.8, 6.8, 0.8 Hz, 2H, Ar—H), 7.31 (ddd, J=7.4, 6.8, 1.1 Hz, 2H, Ar—H), 6.64 (br s, 1H, SerNH), 6.09 (s, 1H, Fmoc-NH), 4.74-4.68 (m, 1H, Ser-CHα), 4.43-4.30 (m, 2H, Fmoc-$CH_2$), 4.22 (t, J=6.8 Hz, 1H, Fmoc-CH), 3.81 (d, J=8.8 Hz, 1H, Ser-$CH_2$β), 3.75 (s, 3H, —$OCH_3$), 3.57 (d, J=8.8 Hz, 1H, Ser-$CH_2$β), 2.44-2.31 (m, 1H, Leu-$CH_2$β), 1.73-1.52 (m, 5H, Leu$CH_2$β, Leu-CHγ, Leu-CH3β), 1.13 (s, 9H, —$C(CH_3)_3$), 0.94-0.82 (m, 6H, 2×Leu-$CH_3$δ); $^{13}$C ($CDCl_3$, 125 MHz): δ 173.9, 170.7, 154.4, 144.1, 144.0, 141.3, 127.6, 127.1, 125.1, 120.0, 73.4, 66.4, 61.9, 59.6, 53.1, 52.4, 47.3, 45.1, 27.3, 25.2, 24.7, 23.7, 23.6; HRMS (ES) Calculated for $C_{30}H_{41}N_2O_6$ 525.2959, found 525.2956 (M+H)+.

N—((S)-2-((((9H-fluoren-9-yl)methoxy)carbonylamino)-2,4-dimethylpentanoyl)-O-(tert-butyl)-L-serine (33)

Methyl ester deprotection conditions were adapted from literature procedure.[44] Dipeptide 32 (0.853 g, 1.63 mmol) was dissolved in aqueous 2-propanol (70% 2-propanol in water, 50 mL) and had $CaCl_2.2H_2O$ (5.88 g) added to generate a 0.8 M $Ca^{2+}$ solution. Sodium hydroxide (0.130 g, 3.25 mmol) was added and the reaction was stirred for 4 h. Acetic acid (0.186 mL, 3.25 mmol) was added to neutralize residual base, and the reaction was concentrated in vacuo. The crude residue purified by flash chromatography (silica gel, 50% EtOAc in hexanes 0.1% AcOH), yielding dipeptide 33 as a white sticky solid (0.368 g, 44%). ($R_f$ 0.3 on $SiO_2$, 0.1% AcOH in EtOAc); $[\alpha]_D^{26}$ 27.0 (c 1.0 $CHCl_3$); IR ($CHCl_3$ cast) 3386, 3320, 3068, 3018, 2974, 2876, 1727, 1665, 1497, 1450, 1240, 1194, 1105 $cm^{-1}$; $^1$H ($CDCl_3$, 500 MHz): δ 7.76 (dd, J=7.7, 0.9 Hz, 2H, Ar—H), 7.59 (ddd, J=7.5, 2.0, 1.0 Hz, 2H, Ar—H), 7.40 (ddd, J=7.5, 7.5, 0.9 Hz, 2H, Ar—H), 7.31 (ddd, J=7.7, 7.5, 1.2, Hz, 2H, Ar—H), 6.78 (br s, 1H, Ser-NH), 5.73 (s, 1H, Fmoc-NH), 4.67-4.56 (m, 1H, Ser-CHα), 4.48-4.34 (m, 2H, Fmoc-$CH_2$), 4.20 (t, J=6.6 Hz, 1H, Fmoc-CH), 3.95-3.88 (m, 1H, Ser-$CH_2$β), 3.54-3.48 (m, 1H, Ser-$CH_2$β, 2.19-2.07 (m, 1H, Leu-$CH_2$β), 1.72-1.59 (m, 2H, Leu-$CH_2$β, Leu-CHγ), 1.54 (s, 3H, Leu-$CH_3$β), 1.19 (s, 9H, —$C(CH_3)_3$), 0.94-0.82 (m, 6H, 2×Leu-$CH_3$δ); $^{13}$C ($CDCl_3$, 125 MHz): δ 174.3, 172.0, 154.9, 143.8, 141.4, 129.1, 128.2, 127.7, 127.1, 125.0, 120.0, 74.7, 66.6, 61.0, 59.9, 52.7, 47.2, 45.8, 27.7, 24.4, 24.0, 23.6; HRMS (ES) Calculated for $C_{29}H_{37}N_2O_6$ 509.2657, found 509.2657 $(M-H)^-$.

α-MeLeu5-pyr-1-apelin-13 A2 (14)

Advanced intermediate 7 (0.2 mmol) was subjected to manual SPPS, introducing amino acids in the following order: 33, Fmoc-Pro-OH, and Fmoc-Arg(Pmc)-OH. The resin was split into half, and Fmoc-SPPS was continued on 0.1 mmol scale, coupling pyr-Glu-OH. No endcapping was performed following addition of 33. A portion (0.05 mmol) of resin-bound peptide was cleaved as previously described and purified using a $C_{18}$ RP-HPLC analytical column (Method A), eluting at 13.7 min. The desired peptide was isolated as a white solid after lyophilization (8.5 mg, 11%). Monoisotopic MW calculated for $C_{70}H_{114}BrN_{22}O_{16}$ 532.5983, found high resolution (FTICR-ESI-MS) 532.5972 $(M+3H)^{3+}$. "Pmc" refers to 2,2,5,7,8-pentamethylchroman-6-sulfonyl.

α-MeLeu9-apelin-17 A2 (15)

The remaining 0.1 mmol carried over from the synthesis of 14 was coupled with FmocGln(Trt)-OH, Fmoc-Arg (Pmc)-OH, Fmoc-Arg(Pmc)-OH, Fmoc-Phe-OH, and Fmoc-Lys(Boc) OH. A portion (0.05 mmol) of resin-bound peptide was cleaved as previously described and purified using a $C_{18}$ RP-HPLC analytical column (Method A), eluting at 11.5 min. The desired peptide was isolated as a white solid after lyophilization (14.3 mg, 13%). Monoisotopic MW calculated for $C_{97}H_{163}BrN_{34}O_{20}$ 550.7986, found high resolution (FTICR-ESI-MS) 550.7974 $(M+4H)^{4+}$.

Synthesis of aza-arginine A2 Peptides tert-butyl (2-(diphenylmethylene)hydrazine-1-carbonyl)-L-leucinate (34)

Semicarbazone 34 was prepared by modifying a literature procedure.[46] A solution of benzophenone hydrazone (4.39 g, 22.4 mmol) in dry $CH_2Cl_2$ (50 mL) was cooled to 0° C. and cannulated into a 0° C. solution of disuccinimidyl carbonate (7.41 g [85% purity], 24.6 mmol) in dry $CH_2Cl_2$ (50 mL) and dry DMF (10 mL). The reaction was warmed to room temperature for 45 minutes, then cooled down to 0° C. A 0° C. solution of H-Leu-OtBu.HCl (5.00 g, 22.4 mmol) and DIPEA (7.79 mL, 44.7 mmol) in dry $CH_2Cl_2$ (50 mL) was then cannulated into the reaction vessel and allowed to slowly come up to room temperature over 16 h. The reaction was concentrated in vacuo and purified by flash chromatography (silica gel, 20% EtOAc in hexanes), yielding a light yellow sticky solid (8.29 g, 91%). ($R_f$ 0.8 on $SiO_2$, 1:1 hexanes:EtOAc); $[\alpha]_D^{26}$ 36.7 (c 1.27 $CHCl_3$); IR ($CHCl_3$ cast) 3414, 3355, 3188, 3062, 2957, 2871, 1732, 1682, 1519, 1446, 1368, 1153, 1113 $cm^{-1}$; $^1H$ ($CDCl_3$, 400 MHz): δ 7.59 (s, 1H, =N—NH), 7.57-7.46 (m, 5H, Ar—H), 7.40-7.29 (m, 3H, Ar—H), 7.29-7.22 (m, 2H, Ar—H), 6.68 (d, J=9.0 Hz, 1H, Leu-NH), 4.52 (ddd, J=8.8, 8.8, 5.6 Hz, 1H, Leu-CHα), 1.85-1.74 (m, 1H, Leu-CHγ), 1.74-1.60 (m, 2H, Leu-$CH_2$β), 1.50 (s, 9H, —$C(CH_3)_3$), 1.00 (d, J=6.5 Hz, 6H, 2×Leu-$CH_3$δ); $^{13}C$ ($CDCl_3$, 125 MHz): δ 172.6, 154.9, 148.2, 137.0, 131.9, 129.8, 129.7, 129.4, 129.3, 128.8, 128.5, 128.3, 128.1, 127.2, 126.5, 81.7, 51.9, 42.4, 28.1, 25.0, 23.0, 22.1; HRMS (ES) Calculated for $C_{24}H_{32}N_3O_3$ 410.2438, found 410.2438 $(M+H)^+$.

tert-butyl (1-(3-chloropropyl)-2-(diphenylmethylene)hydrazine-1-carbonyl)-L-leucinate (35)

Alkylation conditions were initially adapted from a literature procedure.[45] Semicarbazone 34 (2.47 g, 6.03 mmol) was dissolved in THF (50 mL) and cooled to 0° C. Aqueous tetraethylammonium hydroxide (22.2 mL [20% solution], 30.1 mmol) was added and stirred for 30 minutes, followed by the addition of 1-bromo-3-chloropropane (4.47 mL, 45.2 mmol) at 0° C. The reaction was slowly warmed to room temperature and was quenched after 72 h by the addition of 10% citric acid (20 mL) followed by brine (20 mL). Organic components were extracted with EtOAc (3×100 mL), dried over $Na_2SO_4$, filtered and concentrated in vacuo. Alkylated semicarbazone 204 was purified by flash chromatography (silica gel, 15% EtOAc in hexanes) and was isolated as a yellow oil (2.16 g, 74%). (Rf 0.85 on $SiO_2$, 2:1 hexanes: EtOAc); $[\alpha]_D^{26}$ 67.5 (c 1.42 $CHCl_3$); IR ($CHCl_3$ cast) 3414, 3061, 2959, 2870, 1734, 1682, 1499, 1446, 1368, 1154 $cm^{-1}$; $^1H$ ($CDCl_3$, 500 MHz): δ 7.55-7.41 (m, 6H, Ar—H), 7.41-7.30 (m, 4H, Ar—H), 6.69 (d, J=8.7 Hz, 1H, Leu-NH), 4.47 (ddd, J=8.8, 8.7, 5.6 Hz, 1H, Leu-CHα), 3.46 (dt, J=14.7, 6.8 Hz, 1H, N—$CH_2$), 3.38-3.27 (m, 3H, N—$CH_2$, 2×N—$CH_2CH_2$), 1.80-1.72 (m, 3H, 2×-$CH_2$Cl, Leu-CHγ), 1.66 (ddd, J=13.6, 8.0, 5.6 Hz, 1H, Leu-$CH_2$β), 1.61-1.51 (m, 1H, Leu$CH_2$β), 1.48 (s, 9H, —$C(CH_3)_3$), 0.98 (d, J=6.6 Hz, 6H, 2×Leu-$CH_3$δ); $^{13}C$ ($CDCl_3$, 125 MHz): δ 172.8, 159.4, 158.3, 138.6, 135.7, 130.2, 129.8, 128.9, 128.8, 128.6, 128.2, 81.3, 52.7, 44.1, 42.4, 42.1, 30.0, 28.1, 25.1, 22.9, 22.2; HRMS (ES) Calculated for $C_{27}H_{37}ClN_3O_3$ 486.2518, found 486.2518 $(M+H)^+$.

tert-butyl (1-(3-azidopropyl)-2-(diphenylmethylene) hydrazine-1-carbonyl)-L-leucinate (36)

This reaction was adapted from a literature procedure.[45] Chloroalkylated semicarbazone 35 (2.08 g, 4.27 mmol) and sodium azide (0.833 g, 12.8 mmol) were dissolved in DMF (50 mL) and heated at 60° C. for 20 h. The reaction was cooled and had $H_2O$ (150 mL) added to it, followed by EtOAc (3×150 mL) washes to extract organic components. Pooled EtOAc layers were dried over $Na_2SO_4$, filtered, and concentrated in vacuo. The product was purified using flash chromatography (silica gel, 10% EtOAc in hexanes), generating azide 36 as a yellow oil (1.90 g, 90%). (Rf 0.2 on $SiO_2$, 9:1 hexanes:EtOAc); $[\alpha]_D^{26}$ 53.8 (c 1.00 $CHCl_3$); IR ($CHCl_3$ cast) 3411, 3061, 2958, 2871, 2097, 1734, 1683, 1499, 1446, 1368, 1257, 1154 $cm^{-1}$; $^1H$ ($CDCl_3$, 500 MHz): δ 7.54-7.40 (m, 6H, Ar—H), 7.40-7.26 (m, 4H, Ar—H), 6.74 (d, J=8.7 Hz, 1H, Leu-NH), 4.47 (ddd, J=8.8, 8.7, 5.6 Hz, 1H, Leu-CHα), 3.42 (dt, J=14.7, 7.0 Hz, 1H, N—$CH_2$), 3.27 (dt, J=14.7, 6.8 Hz, 1H, N—$CH_2$), 3.05 (t, J=7.1 Hz, 2H, —$CH_2N_3$), 1.76 (ddsept, J=12.9, 7.8, 6.5 Hz, 1H, Leu-CHγ), 1.70-1.62 (m, 1H, Leu-$CH_2$β), 1.61-1.55 (m, 1H, Leu-$CH_2$β), 1.56-1.49 (m, 2H, —$CH_2CH_2N_3$), 1.48 (s, 9H, —$C(CH_3)_3$), 0.99 (d, J=6.6 Hz, 3H, Leu-$CH_3$δ), 0.98 (d, J=6.6 Hz, 3H, Leu-$CH_3$δ); $^{13}C$ ($CDCl_3$, 125 MHz): δ 172.8, 158.5, 158.4, 138.6, 135.8, 130.2, 129.8, 128.9, 128.8, 128.5, 128.3, 81.3, 52.7, 48.9, 43.4, 42.1, 28.1, 26.2, 25.1, 22.9, 22.2; HRMS (ES) Calculated for $C_{27}H_{37}N_6O_3$ 493.2922, found 493.2922 $(M+H)^+$.

tert-butyl (1-(3-azidopropyl)hydrazine-1-carbonyl)-L-leucinate (37)

This procedure was adapted from literature protocols.[46,59,] Azide 36 (1.89 g, 3.84 mmol) was dissolved in a solution of hydroxylamine hydrochloride (1.07 g, 15.4 mmol) in pyridine (75 mL) and heated to 60° C. for 22 h. The reaction was cooled to room temperature, then concentrated in vacuo, using $CH_2Cl_2$ and EtOAc co-evaporations to remove residual pyridine. The product was purified using flash chromatography (silica gel, 60% EtOAc in hexanes, 0.1% DIPEA) yielding semicarbazide 37 as a yellow oil (1.19 g, 94%). (Rf 0.5 on $SiO_2$, 1:1 hexanes:EtOAc); $[\alpha]_D^{26}$ 5.0 (c 0.92 $CHCl_3$); IR ($CHCl_3$ cast) 3406, 3335, 3216, 2958, 2934, 2871, 2098, 1732, 1654, 1510, 1368, 1257, 1155 $cm^{-1}$; $^1H$ ($CDCl_3$, 500 MHz): δ 6.67 (d, J=8.8 Hz, 1H, Leu-NH), 4.33 (ddd, J=8.9, 8.8, 5.5 Hz, 1H, Leu-CHα), 3.64 (s, 2H, $H_2$N—N), 3.62-3.51 (m, 2H, N—$CH_2$), 3.36 (t, J=6.7 Hz, 2H, —$CH_2N_3$), 1.84 (app p, J=6.8 Hz, 2H, —$CH_2CH_2N_3$), 1.71 (ddsept, J=8.2, 8.0, 6.5 Hz, 1H, Leu-CHγ), 1.59 (ddd, J=13.6, 8.1, 5.5 Hz, 1H, Leu-$CH_2$β), 1.53-1.47 (m, 1H, Leu$CH_2$β), 1.45 (s, 9H, —$C(CH_3)_3$), 0.95 (d, J=6.6 Hz, 6H, 2×Leu-$CH_3$δ); $^{13}C$ ($CDCl_3$, 125 MHz): δ 173.5, 158.7, 81.3, 52.3, 49.2, 48.0, 42.4, 28.1, 26.3, 25.0, 22.9, 22.1; HRMS (ES) Calculated for $C_{14}H_{29}N_6O_3$ 329.2296, found 329.2290 $(M+H)^+$.

(9H-fluoren-9-yl)methyl (S)-2-(2-(3-azidopropyl)-2-(((S)-1-(tert-butoxy)-4-methyl-1-oxopentan-2-yl) carbamoyl)hydrazine-1-carbonyl)pyrrolidine-1-carboxylate (38)

A solution of Fmoc-Pro-OH (1.65 g, 4.88 mmol), HATU (1.86 g, 4.88 mmol), HOAt (0.81 mL [0.6 M solution], 0.49 mmol) and DIPEA (2.13 mL, 12.2 mmol) were dissolved in dry DMF (20 mL) and preactivated for 5 minutes before the addition of a solution of semicarbazide 37 (1.34 g, 4.07 mmol) in dry $CH_2Cl_2$ (20 mL). The reaction mixture was stirred under Ar gas for 18 h then concentrated in vacuo. The crude reaction mixture was resuspended in EtOAc (75 mL) and washed with 10% citric acid (50 mL), water (50 mL) and brine (50 mL). Pooled aqueous layers were washed with EtOAc (2×75 mL), and pooled organic fractions were dried over $Na_2SO_4$, filtered and concentrated in vacuo. The product was purified by flash chromatography (silica gel, 50% EtOAc in hexanes) yielding azatripeptide 38 as a white solid (1.74 g, 66%). (Rf 0.4 on $SiO_2$, 1:1 hexanes:EtOAc); $[\alpha]_D^{26}$−7.2 (c 0.83 $CHCl_3$); IR ($CHCl_3$ cast) 3357, 3229, 2957, 2872, 2097, 1690, 1529, 1452, 1424, 1367, 1257, 1155 $cm^{-1}$; $^1H$ ($CDCl_3$, 500 MHz): δ 8.20 (s, 1H, C(O)NH—N), 7.80-7.74 (m, 2H, Ar—H), 7.61-7.54 (m, 2H, Ar—H), 7.47-7.37 (m, 2H, Ar—H), 7.31 (t, J=7.5 Hz, 2H, Ar—H), 6.04 (d, J=8.2 Hz, 1H, Leu-NH), 4.47 (dd, J=10.5, 7.1 Hz, 1H, Fmoc-$CH_2$), 4.42-4.29 (m, 2H, Fmoc-$CH_2$, Leu-CHα), 4.25 (t, J=6.8 Hz, 1H, Fmoc-CH), 4.19 (dd, J=7.4, 4.5 Hz, 1H, Pro-CHα), 3.67-3.54 (m, 3H, 2×N—$CH_2$, Pro-$CH_2$δ), 3.55-3.46 (m, 1H, Pro-$CH_2$δ), 3.44-3.33 (m, 2H, —$CH_2N_3$), 2.27 (ddd, J=11.5, 5.3, 4.9 Hz, 1H, Pro-$CH_2$β), 2.17-2.06 (m, 2H, Pro-$CH_2$β, Pro-$CH_2$γ), 2.01-1.93 (m, 1H, Pro-$CH_2$γ), 1.82-1.72 (m, 2H, —$CH_2CH_2N_3$), 1.63 (ddd, J=13.4, 6.7, 6.5 Hz, 1H, Leu-CHγ), 1.54 (ddd, J=7.1, 6.7, 6.7 Hz, 1H, Leu-$CH_2$β), 1.48-1.38 (m, 10H, Leu-$CH_2$β, —$C(CH_3)_3$), 0.84 (d, J=6.5, 3H, Leu-$CH_3$δ), 0.83 (d, J=6.5, 3H, Leu-$CH_3$δ); $^{13}C$ ($CDCl_3$, 125 MHz): δ 173.5, 170.9, 156.8, 156.0, 143.7, 141.4, 127.9, 127.1, 125.0, 120.1, 81.3, 68.0, 59.2, 52.6, 49.2, 47.2, 47.1, 46.2, 41.9, 28.8, 28.0, 27.2, 25.0, 24.7, 22.8, 22.1; HRMS (ES) Calculated for $C_{34}H_{46}N_7O_6$ 648.3504, found 648.3503 $(M+H)^+$.

(2-((S)-1-(((9H-fluoren-9-yl)methoxy)carbonyl)pyrrolidine-2-carboxamido)-7-((tert-butoxycarbonyl)amino)-11,11-dimethyl-9-oxo-10-oxa-2,6,8-triazadodec-7-enoyl)-L-leucine (39)

A solution of azatripeptide 38 (0.803 g, 1.24 mmol) in dry $CH_2Cl_2$ (20 mL) was cooled to 0° C. and had TFA (10 mL) added and stirred for 15 minutes. The reaction was warmed to room temperature for 90 minutes and concentrated in vacuo, using toluene co-evaporations to remove residual TFA. The product was resuspended in MeOH (20 mL), 10% Pd/C (25 mg) was added, and the reaction was stirred under an atmosphere of hydrogen gas for 75 minutes. The reaction mixture was filtered through a pad of Celite, concentrated in vacuo to dryness, and resuspended in dry $CH_2Cl_2$ (20 mL) with triethylamine (0.76 mL, 5.45 mmol) and 1,3-di-Boc-2 (trifluoromethylsulfonyl) guanidine (0.801 g, 2.05 mmol) for 40 h. Solvents were removed in vacuo and 39 was purified using flash chromatography (silica gel, 90% EtOAc in hexanes, 0.1% AcOH), yielding a white solid (0.413 g, 41%). (Rf 0.05 on $SiO_2$, 0.1% AcOH in EtOAc); $[\alpha]_D^{26}$−42.4 (c 1.00 $CH_3OH$); IR ($CH_3OH$ cast) 3328, 2959, 1721, 1688, 1642, 1530, 1419, 1335, 1156, 1136 $cm^{-1}$; $^1H$ ($CDCl_3$, 500 MHz): δ 9.47 (br s, 1H, Arg-$NH_\varepsilon$), 8.53 (s, 1H, C(O)NH—N), 7.75 (d, J=7.5 Hz, 2H, Ar—H), 7.56 (d, J=7.5 Hz, 1H, Ar—H), 7.54 (d, J=7.5 Hz, 1H, Ar—H), 7.39 (app t, J=7.4 Hz, 2H, Ar—H), 7.30 (app t, J=7.5 Hz, 2H, Ar—H), 6.47 (br s, 1H, Leu-NH), 4.39 (dd, J=10.4, 7.1 Hz, 1H, Fmoc-$CH_2$), 4.30-4.23 (m, 2H, Fmoc-$CH_2$, Leu-CHα), 4.23-4.17 (m, 2H, Fmoc-CH, Pro-CHα), 3.84-3.69 (m, 1H, Arg-N—$CH_2$β), 3.64-3.57 (m, 1H, Pro-$CH_2$δ), 3.56-3.48 (m, 2H, Pro-$CH_2$δ, Arg-$CH_2$δN), 3.46-3.38 (m, 1H, Pro-$CH_2$δ), 3.35-3.26 (m, 1H, Arg-$CH_2$δN), 2.21-2.09 (m, 2H, Pro-$CH_2$β, Arg-$CH_2$γ), 2.09-2.01 (m, 1H, Arg-$CH_2$γ), 1.93-1.86 (m, 1H, Pro-$CH_2$β), 1.84-1.72 (m, 2H, Pro-$CH_2$γ), 1.70-1.54 (m, 3H, Leu-$CH_\gamma$, 2×Leu$CH_2$β), 1.49 (m, 9H, —$C(CH_3)_3$), 1.46 (s, 9H, —$C(CH_3)_3$), 0.95-0.77 (m, 6H, 2×Leu-$CH_3$δ); $^{13}C$ ($CDCl_3$, 125 MHz): δ 171.8, 163.1, 158.7, 156.5, 155.3, 153.1, 143.7, 141.3, 129.0, 128.2, 127.8, 127.1, 127.1, 125.3, 125.0, 120.0, 83.4, 79.8, 67.8, 58.7, 53.1, 47.1, 44.9, 39.9, 37.9, 29.7, 28.3, 28.1, 27.2, 24.9, 24.5, 22.8, 21.8; HRMS (ES) Calculated for $C_{41}H_{56}N_7O_{10}$ 806.4094, found 806.4088 $(M-H)^-$.

azaArg4-pyr-1-apelin-13 A2 (16)

Advanced intermediate 7 (0.2 mmol) was subjected to manual SPPS, introducing amino acids in the following order: Fmoc-Ser(tBu)-OH, 39, and Fmoc-Arg(Pmc)-OH. The resin was split into half, and Fmoc-SPPS was continued on 0.1 mmol scale, coupling pyr-Glu-OH. No endcapping was performed following addition of 39. A portion (0.05 mmol) of resin-bound peptide was cleaved as previously described and purified using a $C_{18}$ RP-HPLC analytical column (Method A), eluting at 13.5 min. The desired peptide was isolated as a white solid after lyophilization (5.5 mg, 7%). Monoisotopic MW calculated for $C_{68}H_{111}BrN_{23}O_{16}$ 528.2582, found high resolution (FTICR-ESI-MS) 528.2571 $(M+3H)^{3+}$.

azaArg8-apelin-17 A2 (17)

The remaining 0.1 mmol carried over from the synthesis of 16 was coupled with FmocGln(Trt)-OH, Fmoc-Arg (Pmc)-OH, Fmoc-Arg(Pmc)-OH, Fmoc-Phe-OH, and Fmoc-Lys(Boc) OH. A portion (0.05 mmol) of resin-bound peptide was cleaved as previously described and purified using a $C_{18}$ RP-HPLC analytical column (Method A), eluting at 11.1 min. The desired peptide was isolated as a white solid after lyophilization (15.6 mg, 14%). Monoisotopic MW calculated for $C_{95}H_{160}BrN_{35}O_{20}$ 547.5435, found high resolution (FTICR-ESI-MS) 547.5430 $(M+4H)^{4+}$.

Synthesis of aza-leucine A2 Peptides tert-butyl O-(tert-butyl)-N-(2-(diphenylmethylene) hydrazine-1-carbonyl)-L-serinate (40)

This molecule was prepared by adapting a literature procedure.[46] A solution of benzophenone hydrazone (1.55 g, 7.88 mmol) in dry $CH_2Cl_2$ (30 mL) was cooled to 0° C. and cannulated into a 0° C. solution of disuccinimidyl carbonate (2.61 g [85% purity], 8.67 mmol) in dry $CH_2Cl_2$ (30 mL) and dry DMF (5 mL). The reaction was warmed to room temperature for 45 min, then cooled down to 0° C. A 0° C. solution of H-Ser(tBu)-OtBu.HCl (2.00 g, 7.88 mmol) and DIPEA (2.75 mL, 15.8 mmol) in dry $CH_2Cl_2$ (20 mL) was then cannulated into the reaction vessel and allowed to slowly come up to room temperature over 24 h. The reaction was concentrated in vacuo and purified by flash chromatography (silica gel, 25% EtOAc in hexanes), yielding a light yellow sticky solid (2.94 g, 83%). (Rf 0.4 on $SiO_2$, 1:1 hexanes:EtOAc); $[\alpha]_D^{26}$ 28.0 (c 1.0 $CH_2Cl_2$); IR ($CH_2Cl_2$ cast) 3425, 3173, 3059, 2975, 2932, 1751, 1743, 1693, 1518, 1367, 1161 $cm^{-1}$; $^1H$ ($CDCl_3$, 500 MHz): δ 7.61 (s, 1H, =N—NH), 7.58-7.45 (m, 5H, Ar—H), 7.38-7.29 (m, 3H, Ar—H), 7.29-7.23 (m, 2H, Ar—H), 7.17 (d, J=8.9 Hz, 1H, Ser-NH), 4.55 (ddd, J=8.9, 3.3, 2.9 Hz, 1H, Ser-CHα), 3.88 (dd, J=8.6, 2.9 Hz, 1H, Ser-$CH_2$β), 3.64 (dd, J=8.6, 3.3 Hz, 1H, Ser-$CH_2$β), 1.50 (s, 9H, C(O)O$C(CH_3)_3$), 1.22 (s, 9H, —$CH_2OC(CH_3)_3$); $^{13}C$ ($CDCl_3$, 125 MHz): δ 169.9, 155.2, 147.9, 137.1, 131.9, 129.7, 129.2, 128.5, 128.2, 127.1, 81.6, 73.1, 62.7, 53.8, 28.1, 27.5; HRMS (ES) Calculated for $C_{25}H_{34}N_3O_4$ 440.2544, found 440.2549 $(M+H)^+$.

tert-butyl O-(tert-butyl)-N-(2-(diphenylmethylene)-1-(2-methylallyl)hydrazine-1-carbonyl)-L-serinate (41)

Alkylation conditions were adapted from a literature procedure.[45] Semicarbazone 40 (0.945 g, 2.15 mmol) was dissolved in THF (10 mL) and cooled to 0° C. Aqueous tetraethylammonium hydroxide (7.91 mL [20% solution], 10.8 mmol) was added and stirred for 30 minutes, followed by the addition of 3-bromo-2-methylpropene (1.63 mL, 16.1 mmol) at 0° C. The reaction was slowly warmed to room temperature and was quenched after 60 h by the addition of 10% citric acid (15 mL) followed by brine (15 mL). Organic components were extracted with EtOAc (3×75 mL), dried over $Na_2SO_4$, filtered and concentrated in vacuo. Alkylated semicarbazone 41 was purified by flash chromatography (silica gel, 20% EtOAc in hexanes) and was isolated as a yellow oil (1.06 g, 99%). (Rf 0.6 on $SiO_2$, 3:1 hexanes:EtOAc); $[\alpha]_D^{26}$ 6.1 (c 0.75 CH2Cl2); IR ($CH_2Cl_2$ cast) 3421, 3062, 2974, 2935, 2877, 1745, 1687, 1496, 1366, 1154, 1098 $cm^{-1}$; $^1H$ ($CDCl_3$, 500 MHz): δ 7.50-7.39 (m, 6H, Ar—H, Ser-NH), 7.39-7.34 (m, 1H, Ar—H), 7.32-7.27 (m, 4H, Ar—H), 4.71 (dq, J=1.4, 1.1 Hz, 1H, =CHH), 4.58 (ddd, J=8.9, 3.2, 3.2 Hz, 1H, Ser-CHα), 4.48-4.43 (m, 1H, =CHH), 3.98 (d, J=17.0 Hz, 1H, Leu-$NCH_2$β), 3.88-3.79 (m, 2H, Ser-$CH_2$β, Leu-NCH2β), 3.62 (dd, J=8.6, 3.3 Hz, 1H, Ser-$CH_2$β), 1.48 (s, 9H, $C(O)OC(CH_3)_3$), 1.41-1.32 (m, 3H, —$CH_3$), 1.17 (s, 9H, —$CH_2OC(CH_3)_3$); $^{13}C$ ($CDCl_3$, 125 MHz): δ 170.2, 158.5, 154.1, 139.8, 139.2, 135.9, 129.5, 129.4, 128.3, 128.2, 128.0, 111.8, 81.3, 72.9, 62.8, 54.7, 50.6, 28.1, 27.4 19.5; HRMS (ES) Calculated for $C_{29}H_{40}N_3O_4$ 494.3013, found 494.3010 $(M+H)^+$.

tert-butyl O-(tert-butyl)-N-(1-isobutylhydrazine-1-carbonyl)-L-serinate (42)

Alkylated semicarbazone 41 (2.19 g, 4.43 mmol) was dissolved in MeOH (50 mL) and had 10% Pd/C (20 mg) added. The suspension was stirred under hydrogen gas for 20 h, filtered through a pad of Celite, and concentrated in vacuo. The crude residue purified using flash chromatography (silica gel, 50% EtOAc in hexanes), yielding semicarbazide 42 as a yellow oil (1.37 g, 93%). ($R_f$ 0.6 on $SiO_2$, 3:1 hexanes:EtOAc); $[\alpha]_D^{26}$ 20.8 (c 0.45 $CH_2Cl_2$); IR ($CH_2Cl_2$ cast) 3420, 3331, 3217, 2974, 2934, 2873, 1741, 1656, 1509, 1366, 1232, 1157, 1100 $cm^{-1}$; $^1H$ ($CDCl_3$, 500 MHz): δ 7.04 (d, J=9.0 Hz, 1H, Ser-NH), 4.45 (ddd, J=9.0, 3.1, 3.0 Hz, 1H, Ser-CHα), 3.78 (dd, J=8.6, 3.1 Hz, 1H, Ser-$CH_2$β), 3.56 (s, 2H, $H_2$N—N), 3.52 (dd, J=8.6, 3.2 Hz, 1H, Ser-$CH_2$β), 3.36 (dd, J=13.9, 7.7 Hz, 1H, Leu-NCH2β), 3.26 (dd, J=13.9, 7.4 Hz, 1H, Leu-$NCH_2$β), 2.01-1.89 (m, 1H, Leu-CHγ), 1.46 (s, 9H, $C(O)OC(CH_3)_3$), 1.14 (s, 9H, —$CH_2OC(CH_3)_3$), 0.92 (d, J=6.7 Hz, 3H, Leu-$CH_3$δ), 0.91 (d, J=6.7 Hz, 3H, Leu-$CH_3$δ); $^{13}C$ ($CDCl_3$, 125 MHz): δ 170.8, 159.1, 81.1, 72.8, 63.1, 57.4, 54.4, 28.1, 27.4, 26.1, 19.9; HRMS (ES) Calculated for $C_{16}H_{34}N_3O_4$ 332.2544, found 332.2539 $(M+H)^+$.

tert-butyl N-(2-((S,)-2-((((9H-fluoren-9-yl)methoxy)carbonyl)amino)-5-((((2-chloro-benzyl)oxy)carbonyl)amino)pentanoyl)-1-isobutylhydrazine-1-carbonyl)-O-(tert-butyl)-L-serinate (43)

A solution of Fmoc-Orn(2-Cl-Cbz)-OH (2.59 g, 4.91 mmol), HATU (1.87 g, 4.91 mmol), HOAt (0.82 mL [0.6 M solution], 0.49 mmol) and DIPEA (2.14 mL, 12.3 mmol) were dissolved in dry DMF (20 mL) and preactivated for 5 minutes before the addition of a solution of semicarbazide 42 (1.36 g, 4.09 mmol) in dry $CH_2Cl_2$ (20 mL). This reaction was stirred under Ar for 30 h then concentrated in vacuo. The crude reaction was resuspended in EtOAc (100 mL) and washed with 10% citric acid (2×100 mL) and brine (100 mL). Pooled aqueous layers were washed with EtOAc (2×100 mL), and pooled organic fractions were dried over $Na_2SO_4$, filtered and concentrated in vacuo. The reaction was purified by flash chromatography (silica gel, 40% EtOAc in hexanes) yielding azatripeptide 43 as a white solid (2.64 g, 77%), with a 17% recovery of 42. ($R_f$ 0.2 on $SiO_2$, 1:1 hexanes:EtOAc); $[\alpha]_D^{26}$ 11.8 (c 1.00 $CHCl_3$); IR ($CHCl_3$ cast) 3321, 3007, 2974, 2934, 2873, 1700, 1657, 1523, 1450, 1367, 1247, 1157 $cm^{-1}$; $^1H$ ($CDCl_3$, 500 MHz): δ 8.31 (s, 1H, C(O)NH—N), 7.79-7.74 (m, 2H, Fmoc-Ar—H), 7.59 (d, J=7.5 Hz, 2H, Fmoc-Ar-H), 7.39 (m, 4H, 2×Fmoc-Ar—H, 2×2-Cl—Ar—H), 7.34-7.28 (m, 2H, Fmoc-Ar—H), 7.27-7.23 (m, 2H, 2×2-Cl—Ar—H), 5.82 (d, J=8.2 Hz, 1H, Ser-NH), 5.53 (d, J=7.8 Hz, 1H, Orn-NHα), 5.27-5.20 (m, 2H, —$OCH_2$(2-Cl)Ph, Orn-$NH_ε$), 5.16 (d, J=13.0 Hz, 1H, —$OCH_2$(2-Cl)Ph), 4.48-4.38 (m, 3H, Ser-CHα, Orn-CHα, Fmoc-$CH_2$), 4.38-4.32 (m, 1H, Fmoc-$CH_2$), 4.21 (t, J=7.0 Hz, 1H, Fmoc-CH), 3.71 (dd, J=8.8, 2.8 Hz, 1H, Ser-$CH_2$β), 3.54-3.45 (m, 2H, Ser-$CH_2$β, Orn-$CH_2$δ), 3.44-3.36 (m, 1H, Leu-NCH2β), 3.33-3.24 (m, 1H, Leu-$NCH_2$β), 3.24-3.15 (m, 1H, Orn-$CH_2$δ), 2.00-1.90 (m, 1H, Orn-$CH_2$β), 1.86-1.77 (m, 1H, Leu-CHγ), 1.75-1.56 (m, 3H, Om-$CH_2$β, 2×Orn-$CH_2$γ), 1.41 (s, 9H, $C(O)OC(CH_3)_3$), 1.08 (s, 9H, —$CH_2OC(CH_3)_3$, 0.89 (d, J=6.6 Hz, 6H, 2×Leu-$CH_3$δ); $^{13}C$ ($CDCl_3$, 125 MHz): δ 173.7, 170.2, 157.1, 156.7, 156.4, 143.6, 141.3, 134.1, 133.5, 129.7, 129.5, 129.4, 127.8, 127.1, 126.8, 125.1, 120.0, 81.6, 72.9, 67.3, 64.1, 62.6, 55.4, 54.5, 52.1, 47.1, 39.7, 29.8, 28.0, 27.3, 26.9, 26.2, 20.0, 20.0; HRMS (ES) Calculated for $C_{44}H_{59}ClN_5O_9$ 836.3996, found 836.4008 $(M+H)^+$.

N-(2-((S)-2-((((9H-fluoren-9-yl)methoxy)carbonyl)amino)-5-((((2-chlorobenzyl)oxy)carbonyl)amino)pentanoyl)-1-isobutylhydrazine-1-carbonyl)-O-(tert-butyl)-L-serine (44)

Azatripeptide 43 (1.21 g, 1.44 mmol) was dissolved in toluene (100 mL) and had flash-grade silica (25.0 g) added. This suspension was refluxed at 115° C. for 95 minutes, checking TLC and LC-MS every 30 minutes. The reaction was cooled to room temperature and a 10% MeOH in $CH_2Cl_2$ solution (100 mL) was added, then filtered through a pad of Celite. The reaction was concentrated in vacuo, and purified by flash chromatography (silica gel, 0-2% MeOH in EtOAc, 0.1% AcOH). The desired product was obtained as a sticky white solid (0.770 g, 69%). ($R_f$ 0.3 on $SiO_2$, 1:4 hexanes:EtOAc, 0.1% AcOH); $[\alpha]_D^{26}$ 14.5 (c 1.00 $CHCl_3$); IR ($CHCl_3$ cast) 3313, 3018, 2971, 2874, 1697, 1528, 1450, 1249, 1193, 1104 $cm^{-1}$; $^1H$ ($CDCl_3$, 500 MHz): δ 8.10 (s, 1H, C(O)NH—N), 7.71 (d, J=7.6 Hz, 2H, Fmoc-Ar—H), 7.54 (d, J=7.5 Hz, 2H, Fmoc-Ar-H), 7.40-7.29 (m, 4H, 2×Fmoc-Ar—H, 2×2-Cl—Ar—H), 7.29-7.16 (m, 4H, 2×Fmoc-Ar—H, 2×2-Cl—Ar—H), 6.05 (br s, 1H, Ser-NH), 5.53 (br s, 1H, Orn-NHα), 5.22-5.11 (m, 2H, —$OCH_2$(2-Cl)Ph), 4.42-4.37 (m, 2H, Ser-CHα, Fmoc-$CH_2$), 4.35-4.27 (m, 1H, Orn-CHα), 4.21 (dd, J=10.1, 8.7 Hz, 1H, Fmoc-$CH_2$), 4.14 (t, J=8.3 Hz, 1H, Fmoc-CH), 3.76-3.68 (m, 1H, Ser-$CH_2$β), 3.52-3.46 (m, 1H, Ser-$CH_2$β), 3.33-3.13 (m, 4H, 2×Orn-$CH_2$δ, 2×Leu-NCH2β), 1.89-1.80 (m, 1H, Orn-$CH_2$β), 1.79-1.65 (m, 2H, Om-$CH_2$β, Leu-CHγ), 1.62-1.54 (m, 2H, Orn-$CH_2$γ), 1.02 (s, 9H, —$CH_2OC(CH_3)_3$), 0.83 (d, J=6.5 Hz, 3H, Leu-$CH_3$δ), 0.81 (d, J=6.5 Hz, 3H, Leu-$CH_3$δ); $^{13}C$ ($CDCl_3$, 125 MHz): δ 171.8, 170.4, 159.7, 158.3, 156.6, 143.6, 141.2, 134.2, 133.4, 129.6, 129.5, 129.3, 127.8, 127.1, 126.9, 125.1, 120.0, 73.6, 67.3, 63.9, 62.1, 55.7, 55.2, 52.5, 47.0, 39.9, 29.7, 27.3, 27.0, 25.9, 20.0; HRMS (ES) Calculated for $C_{40}H_{49}ClN_5O_9$ 778.3224, found 778.3208 $(M-H)^-$.

N—((S)-5-((((9H-fluoren-9-yl)methoxy)carbonyl) amino)-10-((tert-butoxycarbonyl) amino)-2-isobutyl-14,14-dimethyl-4,12-dioxo-13-oxa-2,3,9,11-tetraaza-pentadec-10-enoyl)-O-(tert-butyl)-L-serine (45)

A solution of 44 (0.730 g, 0.94 mmol) in MeOH (50 mL) had 10% Pd/C (25 mg) added, and the suspension was stirred under an atmosphere of hydrogen gas for 135 minutes. The reaction mixture was filtered through a pad of Celite, concentrated in vacuo to dryness, and resuspended in dry $CH_2Cl_2$ (30 mL) with triethylamine (0.59 mL, 4.21 mmol) and 1,3-di-Boc-2-(trifluoromethylsulfonyl)guanidine (0.549 g, 1.40 mmol) for 30 h. Solvents were removed in vacuo and the azatripeptide product was purified using flash chromatography (silica gel, 90% EtOAc in hexanes, 0.1% AcOH), yielding white solid 45 (0.161 g, 20%). ($R_f$ 0.1 on $SiO_2$, 1:4 hexanes:EtOAc, 0.1% AcOH); $[\alpha]_D^{26}$ 2.3 (c 0.85 $CHCl_3$); IR ($CHCl_3$ cast) 3326, 2978, 2934, 1722, 1644, 1531, 1368, 1331, 1136, 1054 $cm^{-1}$; $^1H$ ($CDCl_3$, 500 MHz): δ 8.94 (br s, 1H, C(O)NH—N), 8.46 (br s, 1H, Arg-$NH_\varepsilon$), 7.75 (d, J=7.6 Hz, 2H, Ar—H), 7.58 (d, J=7.6 Hz, 2H, Ar—H), 7.39 (t, J=7.5 Hz, 2H, Ar—H), 7.30 (t, J=7.5 Hz, 2H, Ar—H), 6.16 (br s, 1H, Arg-NHα), 6.08 (s, 1H, Ser-NH), 4.49-4.40 (m, 3H, Arg-CHα, Ser-CHα, Fmoc-$CH_2$), 4.34-4.28 (m, 1H, Fmoc-$CH_2$), 4.18 (t, J=7.0 Hz, 1H, Fmoc-CH), 3.81-3.75 (m, 1H, Ser-$CH_2$β), 3.61-3.49 (m, 1H, Ser-$CH_2$β), 3.49-3.24 (m, 4H, 2×Arg-$CH_2$δ, 2×Leu-N$CH_2$β), 1.92-1.83 (m, 1H, Arg-$CH_2$β), 1.81-1.60 (m, 4H, Arg-$CH_2$β, 2×Arg-$CH_2$γ, Leu-CHγ), 1.50 (s, 9H, Arg-C($CH_3$)$_3$), 1.47 (s, 9H, Arg-C($CH_3$)$_3$), 1.12 (s, 9H, —$CH_2$OC($CH_3$)$_3$), 0.91-0.85 (m, 6H, 2×Leu-$CH_3$δ); $^{13}C$ ($CDCl_3$, 125 MHz): δ 171.1, 170.2, 163.3, 162.4, 157.7, 156.5, 153.2, 143.7, 141.3, 127.8, 127.1, 125.0, 120.0, 83.6, 79.9, 74.7, 67.3, 61.5, 55.8, 54.0, 53.1, 47.1, 40.4, 29.4, 28.3, 28.0, 27.3, 27.0, 25.5, 20.2, 20.1; HRMS (ES) Calculated for $C_{43}H_{64}N_7O_{11}$ 854.4658, found 854.4654 $(M+H)^+$. azaLeu5-pyr-1-apelin-13 A2 (18).

Advanced intermediate 7 (0.2 mmol) was subjected to manual SPPS, introducing amino acids in the following order: 45, Fmoc-Pro-OH, and Fmoc-Arg(Pmc)-OH. The resin was split into half, and Fmoc-SPPS was continued on 0.1 mmol scale, coupling pyr-Glu-OH. No endcapping was performed following addition of 45. A portion (0.05 mmol) of resin-bound peptide was cleaved as previously described and purified using a $C_{18}$ RP-HPLC analytical column (Method A), eluting at 13.3 min. The desired peptide was isolated as a white solid after lyophilization (4.8 mg, 6%). Monoisotopic MW calculated for $C_{68}H_{111}BrN_{23}O_{16}$ 528.2582, found high resolution (FTICR-ESI-MS) 528.2576 $(M+3H)^{3+}$.

azaLeu9-pyr-1-apelin-13 A2 (19)

The remaining 0.1 mmol carried over from the synthesis of 18 was coupled with Fmoc-Gln(Trt)-OH, Fmoc-Arg (Pmc)-OH, Fmoc-Arg(Pmc)-OH, Fmoc-Phe-OH, and Fmoc-Lys(Boc)-OH. A portion (0.05 mmol) of resin-bound peptide was cleaved as previously described and purified using a $C_{18}$ RP-HPLC analytical column (Method A), eluting at 11.3 min. The desired peptide was isolated as a white solid after lyophilization (4.4 mg, 4%). Monoisotopic MW calculated for $C_{95}H_{160}BrN_{35}O_{20}$ 547.5435, found high resolution (FTICR-ESI-MS) 547.5420 $(M+4H)^{4+}$.

Example 8

In Vitro NEP Stability

Figure 9A:
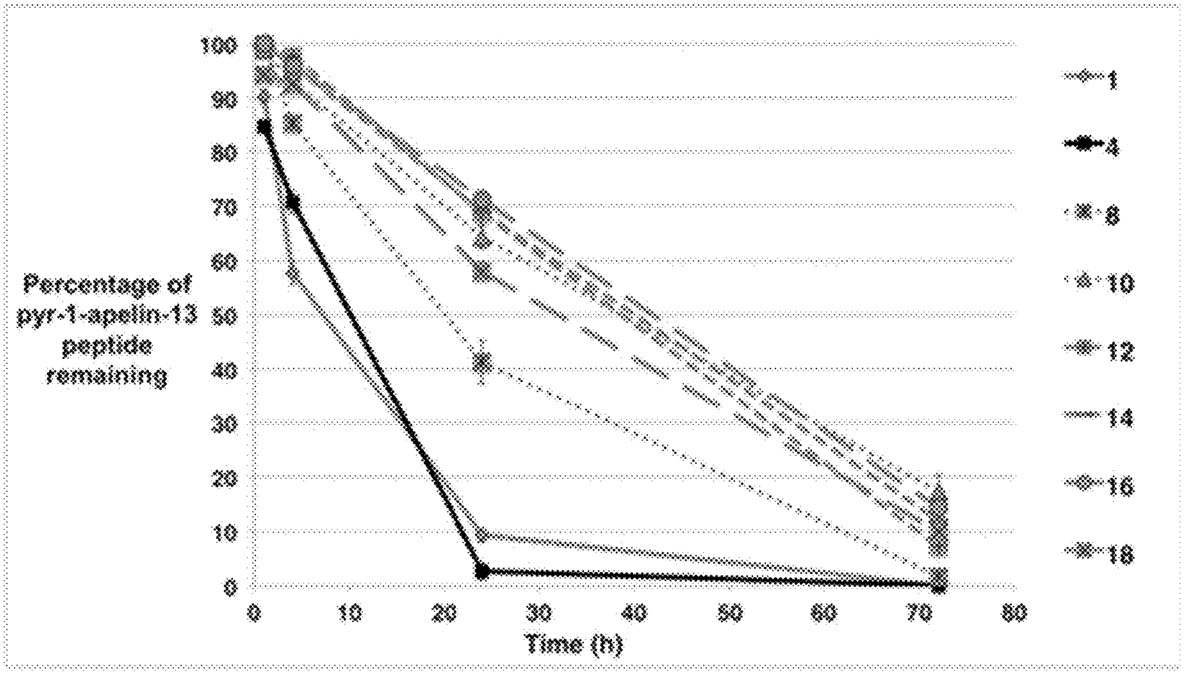
FIGS. 9 A-B demonstrate in vitro NEP degradation trends for pyr-1-apelin-13 peptides (FIG. 9A) and apelin-17 peptides (FIG. 9B) according to embodiments of the disclosure.
Figure 9B:
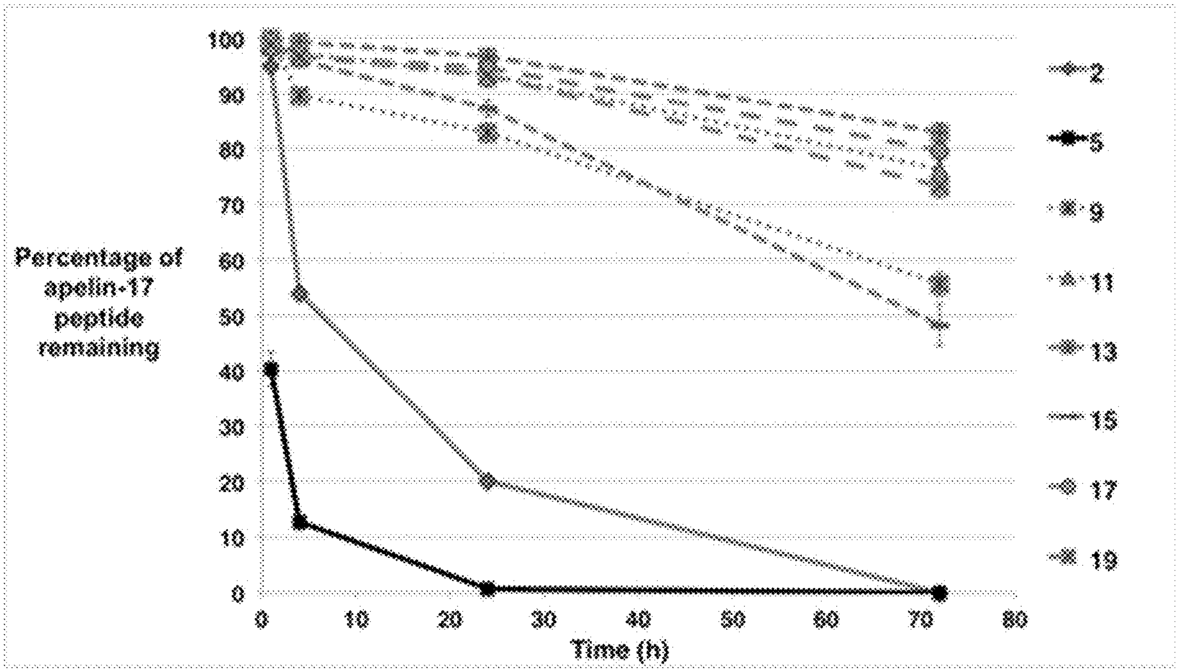

This experiment compared the in vitro NEP stability of the Arg/Leu peptides of the embodiments to native apelin isoforms and their A2 substituted counterparts. Peptides were incubated with recombinant human NEP (rhNEP, Sino Biological) at 37° C. for up to 72 h, and the extent of degradation was analyzed via LC-MS because of the overlapping elution patterns of peptide fragments. FIG. 9 demostrates in vitro NEP degradation trends for a) pyr-1-apelin-13 peptides and b) apelin-17 peptides, comparing native apelin isoforms (1, 2), ACE2-resistant peptides (4, 5) and novel Arg/Leu substituted peptides 8-19. Native apelin isoforms (1, 2) and their respective A2 substituted peptides (4, 5) were degraded by NEP at rates comparable to those previously reported. (McKinnie, S. M. K., et al. *ChemBioChem:* 17, 1495-1498 (2016)). Peptide 5 interestingly showed increased susceptibility to NEP despite all synthetic modifications being at minimum 6 amino acids (P6') away from the site of endoprotease cleavage. Distal amino acid substitutions have been shown to modulate NEP proteolysis in the breakdown of Ap and synthetic substrates (Almenoff, J. et al., *Biochemistry:* 22, 590-599 (1983)) and previous in vitro plasma degradation experiments observed that C-terminal modifications to apelin peptides markedly affected the presence of key peptide fragments (Murza, A. et al., *Biopolymers:* 101, 297-303 (2014)). When examining the impact of Arg/Leu-substitution, all peptides 8-19 showed dramatically improved proteolytic stability to NEP compared to either native peptide (1, 2) or the corresponding A2 substituted peptides (4, 5). Overall, Arg/Leu-substituted apelin-17 A2 peptides showed an enhanced stability compared to the pyr-1-apelin-13 A2 peptides. However, the proteolysis of these peptides was not due to degradation at either location associated with NEP endoprotease activity. Instead, peptides were slowly degraded between Nle-Aib within the A2-modified C-terminus. NEP does have significant carboxydipeptidase activity as exemplified in the degradation of neurological enkephalin pentapeptides (Nalivaeva, N. N. et al., *Handbook of Proteolytic Enzymes:* 3rd Edn, Elsevier Ltd., 612-619 (2013)) and key amino acids have been implicated in binding and orienting the C-terminus of the peptide substrate to facilitate proteolysis. (Dion, N., et al., *Biochem. J.:* 311, 623-627 (1995); Bateman Jr., R. C., et al., *J. Biol. Chem.:* 264, 6151-6157 (1989); McMurray, J. J. et al., *J. Med.:* 371, 993-1004 (2014)). C-terminal dipeptide excision was not observed with native isoforms 1-3, likely due to the unfavorable geometry of proline in the P1' position. Pro to Aib substitution in the A2 peptide series was observed to enable an additional NEP in vitro proteolytic site.

This experiment investigates the ability of synthetic peptides 8-19 to inhibit the inherent proteolytic activity of NEP. Following preincubation of NEP with equimolar concentrations of 8-19, degradation of 1 was nearly identical in either the presence or absence of peptides, suggesting that in vitro proteolytic activity is not significantly impacted.

Example 9

In Vitro Peptide Stability—Plasma

This experiment explored the in vitro plasma stability of synthetic apelin peptides 8-19. Triplicate assessments were performed in human blood plasma and analyzed by RP-HPLC (Table 3). (Wang, W., et al., *Hypertension:* 68, 365-37 (2016)).

TABLE 3

| Arg-Leu | pyr-1-apelin-13 peptides | | | apelin-17 peptides | | |
|---|---|---|---|---|---|---|
| modification | peptide | % apelin 30 min | % apelin 60 min | peptide | % apelin 30 min | % apelin 60 min |
| none (native) | 1 | 45 ± 8 | 12 ± 2 | 2 | 51 ± 17 | 39 ± 7 |
| none (A2) | 4 | 77 ± 19 | 65 ± 14 | 5 | 43 ± 1 | 35 ± 5 |
| D-Leu | 8 | 32 ± 2 | 22 ± 1 | 9 | 80 ± 3 | 80 ± 4 |
| NMeLeu | 10 | 77 ± 3 | 59 ± 6 | 11 | 49 ± 10 | 47 ± 7 |
| αMeArg | 12 | +i | 62 ± 6 | 13 | 61 ± 10 | 55 ± 4 |
| αMeLeu | 14 | 45 ± 6 | 38 ± 3 | 15 | 77 ± 4 | 48 ± 7 |
| azaArg | 16 | 83 ± 3 | 57 ± 1 | 17 | 96 ± 6 | 94 ± 3 |
| azaLeu | 18 | 19 ± 5 | 2 ± 1 | 19 | 82 ± 1 | 68 ± 4 |

Arg/Leu substitution had a varying impact on the different apelin isoforms. With the exception of 11, apelin-17 A2 peptides showed enhanced stability compared to native 2 or A2-substituted peptide 5. Most notably, azaArg8 peptide 17 showed very little degradation during the time course examined. In contrast, there was a much greater range of in vitro stabilities when examining the Arg/Leu substituted pyr-1-apelin-13 A2 peptides. Peptides substituted at the Arg4 position (12, 16) or directly on the susceptible amide bond (10) showed comparable stability to that of 4, while Leu5-modified peptides (8, 14, 18) showed enhanced proteolysis compared to native 1 or A2-modified peptide 4. Based on the previous kinetic studies (McKinnie, S. M. K., et al., *ChemBioChem:* 17, 1495-1498 (2016)) and combined in vitro NEP and plasma pharmacokinetics, NEP proteolysis appears to be more significant in the degradation of apelin-17 isoforms. However, the enhanced in vitro stabilities of Arg/Leu-modified peptides to both NEP and nonspecific plasma proteolysis were encouraging prior to interrogating their individual physiological activities.

Example 10

Binding Affinity of Apelin Peptides

This experiment evaluated the ability of peptides of the present embodiments to bind to the wild-type rat apelin receptor, in order to examine the impact of synthetic modification within the critical RPRL motif of the apelin peptides. Membrane preparations from CHO cells stably expressing the wild-type rat apelin receptor tagged at its C-terminus with EGFP were generated as previously described (Gerbier, R, et al., *FASEB J.,* 29, 314-322 (2015)) and the affinities of native isoforms 1 and 2, parent peptides 4 and 5, and Arg/Leu-peptides 8-19 were determined by their abilities to displace [$^{125}$I]-pyr-1-apelin-13 (0.2 nM). Native isoforms 1 and 2 inhibited specific binding to the wild-type rat apelin receptor with inhibitory constant (Ki) values of 0.3 and 0.05 nM respectively (Table 3).

TABLE 3

| Arg-Leu | pyr-1-apelin-13 peptides | | apelin-17 peptides | |
|---|---|---|---|---|
| modification | peptide | Affinity* Ki (nM) | peptide | Affinity Ki (nM) |
| none (native) | 1 | 0.3 ± 0.07 (4) | 2 | 0.053 ± 0.009 (4) |
| none (A2) | 4 | 2 ± 0.3 (3) | 5 | 0.19 ± 0.025 (3) |
| D-Leu | 8 | 0.12 ± 0.035 (3) | 9 | 0.14 ± 0.056 (3) |
| NMeLeu | 10 | 0.10 ± 0.048 (3) | 11 | 0.45 ± 0.110 (3) |
| α MeArg | 12 | 0.56 ± 0.033 (3) | 13 | 0.13 ± 0.032 (3) |
| α MeLeu | 14 | 0.17 ± 0.050 (3) | 15 | 0.18 ± 0.079 (3) |
| azaArg | 16 | 1 ± 0.10 (3) | 17 | 0.14 ± 0.009 (3) |
| azaLeu | 18 | 0.13 ± 0.063 (3) | 19 | 0.15 ± 0.015 (3) |

*Affinity values are means ± SE (n), with n representing the number of independent experiments performed in duplicate.

Pyr-1-apelin-13 peptides 8, 10, 14, and 18 showed a modest improvement in receptor binding, while parent peptide pyr-1-apelin-13 A2 (4), azaArg4-pyr-1-apelin-13 A2 (16), and αMeArg4-pyr-1-apelin-13 A2 (12) exhibited a slightly weaker affinity compared to 1 (by a factor 6, 3, and 2 respectively). In contrast, Arg/Leu substitution slightly reduced the binding affinity of all apelin-17 peptides compared to native 2, exhibiting Ki values in the subnanomolar range, about three times less potent. However, these data showed no drastic effect on in vitro apelin receptor binding, thus supporting the hypothesis that the selected synthetic modifications within the RPRL motif of apelin were not deleterious for receptor binding.

Example 11

Binding Physiological Experiments

Figure 10A:
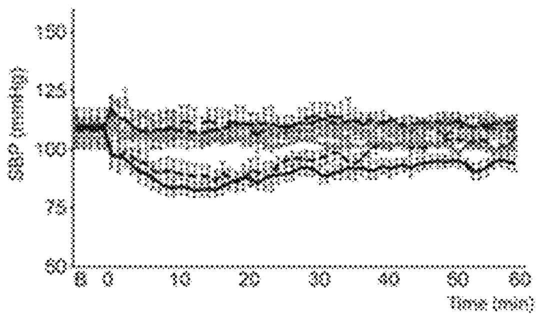
FIGS. 10 A-H demostrates in vivo systolic (SBP, FIG. 10A/FIG. 10E), diastolic (DBP, FIG. 10B/FIG. 10F) and mean arterial blood pressure (MABP, FIG. 10C/FIG. 10G) and heart rate analyses (HR, FIG. 10D/FIG. 10H) following injection of pyr-1-apelin-13 A2 (left) and apelin-17 A2 (right) peptides in anesthetized mice.

Synthetic peptides 8-19 were tested for blood pressure lowering abilities in anesthetized mice. Apelin peptides were injected through the carotid artery, monitoring blood pressure (BP) and heart rate (HR) over 60 minutes. Surprisingly, the potent physiological effects of 4 were not observed with any of the Arg/Leu-substituted pyr-1-apelin-13 A2 peptides (FIG. 10A). Conservative substitutions such as epimerization (8) or N-methylation (10) at the Leu5 position showed no ability to decrease blood pressure in this assay. However, peptides (10, 14, 16) did have a significant and pronounced effect of increasing the murine HR following injection. Tachycardia is directly correlated with native apelin isoforms binding to the receptor (Cheng, X., et al., *European Journal of Pharmacology:* 470, 171-175, 2003) and suggests that these peptides, while not fully functional, still have some inherent physiological activities.

Figure 10B:
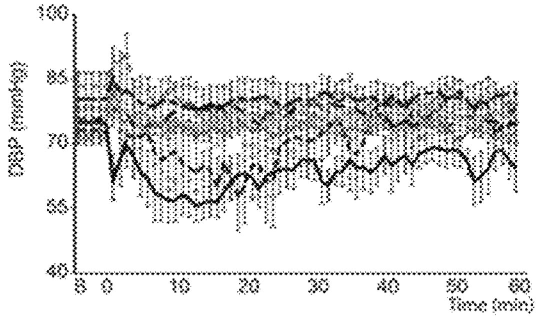
Figure 10C:
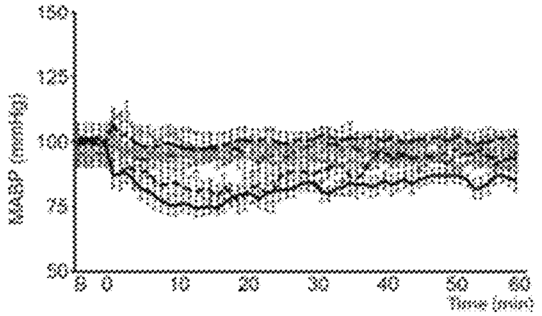
Figure 10D:
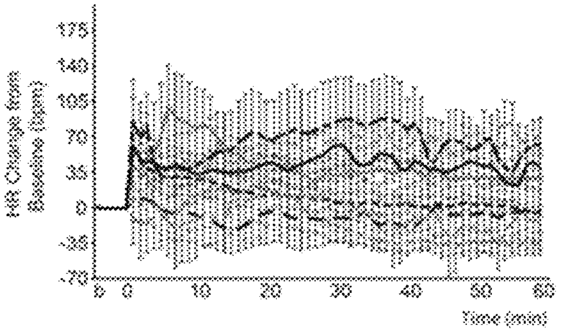
Figure 10E:
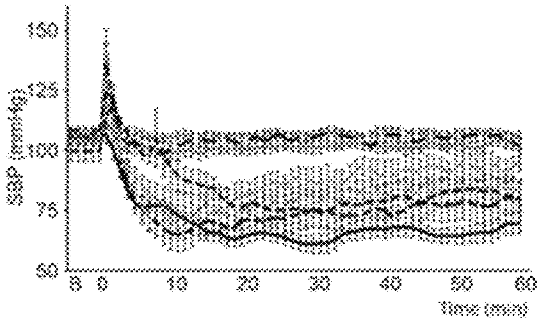
Figure 10F:
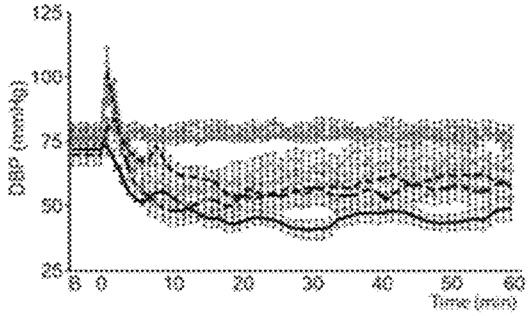
Figure 10G:
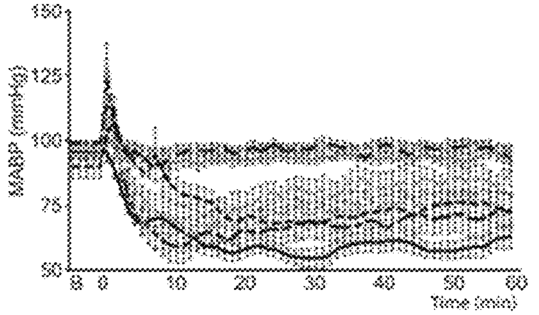
Figure 10H:
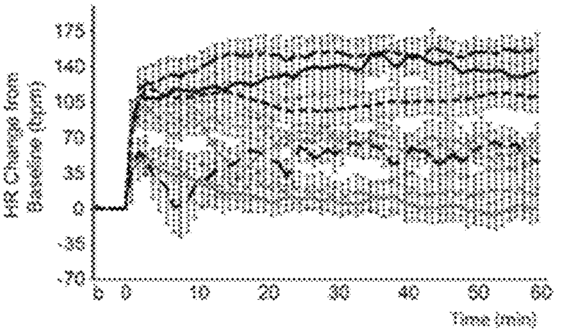
Figure 11B:
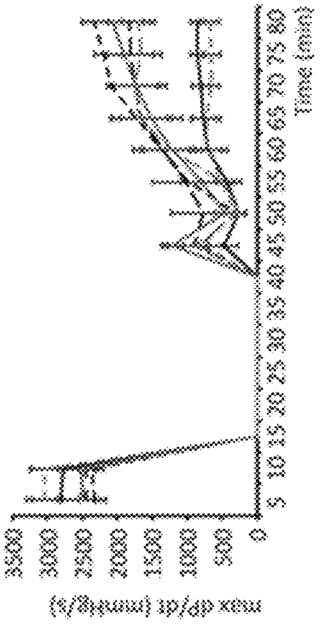
FIGS. 11 A-E demostrates ex vivo heart assessment: heart rate (HR, FIG. 11 A); maximum derivative of change in systolic pressure over time (max dP/dt, FIG. 11 B); left ventricle developed pressure (LVDP, FIG. 11 C), minimum derivative of change in diastolic pressure over time (min dP/dt, FIG. 11 D); and rate-pressure product (RPP, FIG. 11 E), using Langendorff experiments following reperfusion of saline (negative control, sham), native 2 (positive control) and peptides 11, 17-19 after a 30-minute period of ischemia.
Figure 11D:
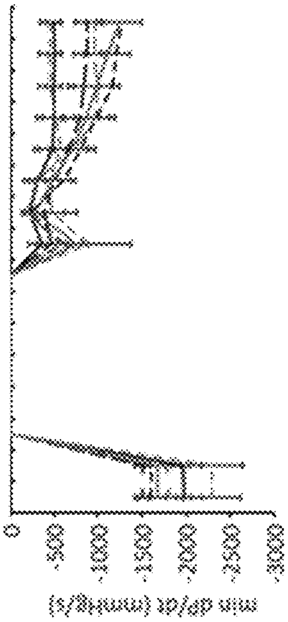
Figure 11A:
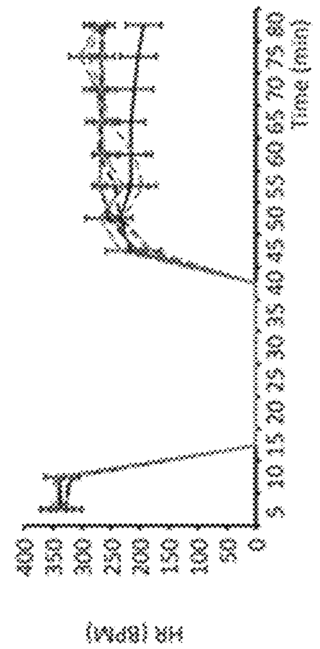
Figure 11C:
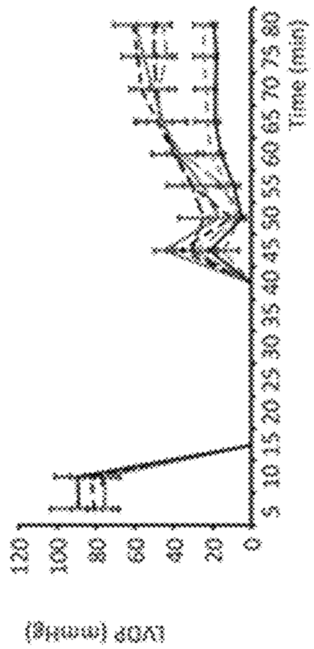
Figure 11E:
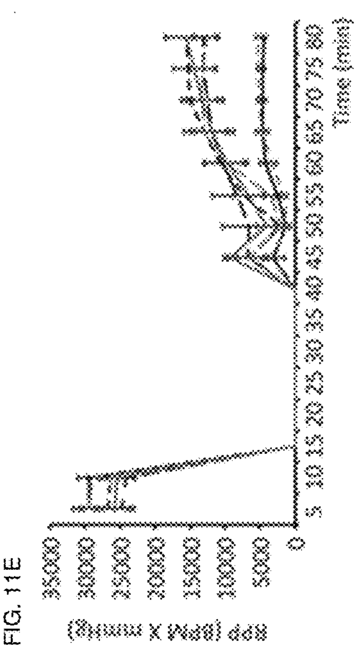

This differential physiological activity was further observed when investigating the impact of the same substitutions on the apelin-17 A2 isoform. All Arg/Leu modifications, even those inactive in the 13 A2 isoform, showed an ability to induce tachycardia. Most significantly, three peptides (11, 17, 19) showed potent hypotensive activity that rivaled or bested that of native 2 or A2 variant 5 (FIG. 10B). Peptides that retained activity involved N-methyl Leu9 peptide 11 and both conformationally flexible aza-peptides 17 and 19, suggesting that these synthetic modifications in the apelin-17 framework were flexible or conservative enough to induce full biological activity upon binding to the apelin receptor.

Example 12

Ischemic Heart Disease

Peptides that showed hypotensive activity were further examined for their abilities to prevent myocardial ischemic reperfusion injury using the Langendorff protocol. Stable isolated rat hearts were exposed to a 30-minute period of ischemia, then reperfused with: saline (vehicle); native 2;

vasoactive peptides 11, 17, 19; or inactive 18; in a post-conditioning protocol. The ex vivo heart was assessed for a variety of parameters (heart rate (HR); left ventricle developed pressure (LVDP); maximum derivative of change in systolic pressure over time (max dP/dt); minimum derivative of change in diastolic pressure over time (min dP/dt); and rate-pressure product (RPP)) indicative of general heart function and performance (FIG. 11).

Following Langendorff experiments, the potent hypotensive apelin-17 A2 peptides 11, 17, and 19 showed an equivalent ability to rescue the heart from ischemic reperfusion injury compared to native isoform 2. In all assessed parameters, these peptides showed full potency, with 17 behaving very analogously to 2, while 11 and 19 showed a slight improvement over the native isoform in max/min dP/dt, LVDP and RPP. It was observed that the inactive pyr-1-apelin-13 A2 peptide 18 behaved comparably to that of the negative saline control.

Synthetic substitution of the site of NEP proteolysis gave rise to three potent peptides (11, 17, and 19) with full beneficial cardiovascular activities, sub-nanomolar receptor affinities, and improved in vitro NEP and plasma stabilities. As well, these peptides showed no ability to inhibit the inherent activity of NEP. Further optimization of the two apelin-17 A2 azapeptide derivatives (17, 19) due to their improved pharmacokinetics is encouraging in the pursuit of an apelin peptide with practical therapeutic applicability. This study additionally provides insight into the limited tolerance to modification within the 'RPRL' motif, and further supports its significant role in the apelinergic system. Most notably, any Arg/Leu modification abolished full agonistic activity within the pyr-1-apelin-13 A2 scaffold. Even conservative substitutions employed such as epimerization, N- or a-methylations, or a-carbon replacement with nitrogen failed to retain full physiological activity despite having comparable in vitro apelin receptor binding. The fact that some of the Arg/Leu modifications show potency in the apelin-17 A2 series suggests that the longer N-terminal extension is capable of facilitating the appropriate receptor interactions and internalization necessary to induce full physiological activity.

The inactivity of both D-Leu substituted peptides 8 and 9 was particularly surprising because of literature precedent that D-Leu pyr-1-apelin-13 retained acceptable abilities to bind (~10-fold decrease in affinity) and inhibit forskolin-induced cAMP accumulation.29 Epimerization within or adjacent to an inducible structural element such as a β-turn would likely be detrimental to activity. However, a recent apelin-17 peptide (P92) with full agonistic activity has been reported with multiple epimerizations, including two flanking both the N-(D-Gln) and C-(D-Leu) termini of the "RPRL" region. Gerbier, et. al., "Development of original metabolically-stable apelin-17 analogs with diuretic and cardiovascular effects," *FASEB J.,* 2017, 31, 687-700. This peptide has additional substitutions that make direct comparison with our peptides difficult, but it is encouraging to know that physiological activity and stability can be enhanced through epimerizations.

Select pyr-1-apelin-13 A2 (10, 14, 16) and apelin-17 A2 (9, 13, 15) peptides had an impact on the heart rate of mice following perfusion without inducing any vasoactive effects. This may be rationalized through the biased agonism of these peptides for G-protein pathways instead of being internalized. It is known that p-arrestin recruitment and internalization initiates vasodilation and additional cardioprotective effects of apelin, and the C-terminal phenylalanine of apelin plays a critical role in this process.

Example 13

In Vitro Protease Experiments

Neprilysin Degradation Assays

Apelin peptides were dissolved in Milli-Q water (1 mM). Recombinant human neprilysin (rhNEP, Sino Biological) was reconstituted in Tris buffer (100 mM Tris, 100 mM NaCl, 10 μM $ZnCl_2$, pH 7.5). To initiate the assay, rhNEP was diluted in Tris buffer (3.1 nM final concentration), and preincubated at 37° C. for 10 minutes prior to the addition of 5 μL of apelin peptide (1 mM) and 1.5 μL internal standard dansyl-Tyr-Val-Gly-OH (1 mM). Aliquots (10 μL) were removed at 0, 1, 4, 24, and 72 h, quenched with 0.1 M EDTA (10 μL), diluted to 100 μL with Milli-Q water and analyzed by LC-MS. Assays were performed in triplicate (n=3) for each time point. Integrated peak areas of the parent apelin peptide and internal standard derived from LC-MS analyses, were extracted using Mass Hunter software (version B.04.00) and compared in positive extracted ion count modus (+EIC, extracted-ion chromatogram). The extent of proteolysis was compared in positive extracted ion count modus (+EIC). The extent of proteolysis was apelin peptide to the internal dansyl-YVG standard (apelin:dansyl-YVG), to the same ratio at the different assay time points. The decrease in apelin:dansyl-YVG ratio was converted to a percentage of cleaved peptide over time.

Neprilysin Inhibition Assays

A solution of rhNEP (3.1 nM in 100 mM Tris, 100 mM 1118 NaCl, 10 μM $ZnCl_2$, pH 7.5) was preincubated with 5 μL of apelin peptide (1 mM) and 1.5 μL internal standard dansyl-Tyr-ValGly-OH (1 mM, dansyl-YVG-OH, Sigma-Aldrich) at 37° C. for 10 min prior to the addition of 5 μL pyr-1-apelin-13 (1 mM). Aliquots (10 μL) were removed at 0, 1, 4, 24, and 72 h, and quenched and analyzed as previously described. Assays were performed in duplicate (n=2) for each time point.

Isolation and Quantification of Apelin Peptides from Plasma

20 μL of plasma was portioned into microfuge tubes and pre-warmed to 37° C. 5 μL of apelin peptide (400 μM) was added and incubated at 37° C. for varying lengths of time. Experiments were quenched by the addition of 20 μL of 10% aqueous TFA. 5 pL of internal standard (1 mM dansyl-Tyr-Val-Gly-OH) was added and experiments were diluted up to 100 μL with 0.1% aqueous TFA. These assays were loaded onto a pre-equilibrated $C_{18}$ spin column (Harvard Apparatus), which had previously been wet with 2×300 μL 50% acetonitrile in 0.1% aqueous TFA and 2×300 μL 0.1% aqueous TFA respectively, centrifuging at 300×g for 2 minutes between each 300 μL aliquot. Quenched plasma assays were centrifuged at 300×g until the sample was loaded. The resultant filtrate was reloaded onto the column along with 100 μL 0.1% aqueous TFA and centrifuged at 300×g two additional times. The desired plasma peptides were washed by the addition of 2×300 μL 0.1% aqueous TFA and centrifuged at 300×g for 2 min, discarding the filtrate after each wash. Desired peptides were eluted by the addition of 300 μL of 40% acetonitrile (human plasma) in 0.1% aqueous TFA and centrifugation at 300×g for 2 minutes. Eluted samples were diluted with 0.1% aqueous trifluoroacetic acid prior to analysis by C18 RP-HPLC. To analyze the remaining percentage of apelin peptides in plasma, incubations. of pyr-1-apelin-13 or apelin-17 in plasma were immediately quenched, worked up and analyzed by $C_{18}$RP-HPLC as previously described, and the ratio of apelin peptide to internal standard was calculated based on the area under the peaks. This 0 minute incubation ratio was used to compare the apelin peptide:internal standard ratios for the time experiments.

Radioligand Binding Experiments

Membrane preparations from CHO cells stably expressing the wild-type rat apelin receptor-EGFP were prepared as previously described (Gerbier et al., New Structural Insights Into The Apelin Receptor: Identification Of Key Residues For Apelin binding; FASEB J. 2015, 29, 314-322; Iturrioz et. al., Development Of Original Metabolically-Stable Apelin-17 Peptides With Diuretic And Cardiovascular Effects; FASEB J. 2017, 31, 687-700.) Crude membrane preparations (1 μg total mass of membranes/assay) were incubated for 3 h at 20° C. with 0.2 nM [$^{125}$I]-pyr-1-apelin-13 (monoiodinated on Lys$^8$ with Bolton-Hunter reagent, Perkin Elmer, Wellesley, Mass., USA) in binding buffer (50 mM HEPES, 5 mM MgCl2 1149 pH 7.5, BSA 1%) alone or in presence of the different compounds at various concentrations. The reaction was stopped by adding 4 mL of cold binding buffer, filtered on Whatman GF/C filters and washed with 5 mL of cold binding buffer. Radioactivity was then counted using a Wizard 1470 Wallac gamma counter (Perkin Elmer, Turku, Finland). Binding experiment data were analyzed with Graph Pad Prism.

Blood Pressure Assays

Mice were anaesthetized with 1.5% isoflurane/oxygen, and body temperature was monitored and maintained at 36° C. by a heating pad. The aorta was cannulated via the right carotid artery using a PV loop catheter (Model 1.2F from Scisense, Transonic) in order to continuously record arterial blood pressure and heart rate (LabScribe 2.0, Scisense). Peptides 1, 2, 4, 5, 8-19 (1.4 μM/kg body weight) or the same volume of saline were injected via the right jugular vein. Results are reported as systolic blood pressure (SBP), diastolic blood pressure (DBP), mean arterial blood pressure (MABP) and heart rate (HR).

Langendorff Isolated Heart Technique

Langendorff heart perfusion and ischemia-reperfusion injury were prepared and cardiac function was measured. Mice were heparinized and anaesthetized with 1.5-2% isoflurane inhalation. The heart was excised, mounted on a Langendorff system, and perfused at a consistent pressure of 80 mmHg with modified Krebs-Henseleit solution (116 mM NaCl, 3.2 mM KCl, 2.0 mM $CaCl_2$), 1.2 mM $MgSO_4$, 25 mM $NaHCO_3$, 1.2 mM $KH_2PO_4$, 11 mM glucose, 0.5 mM EDTA and 2 mM pyruvate), which was kept at 37° C. and continuously oxygenated with 95% $O_2$ and 5% $CO_2$ which maintained the perfusion buffer at pH 7.4. After stabilization and 10 min baseline recording, global ischemia was induced for 30 min followed by 40 min of reperfusion. Apelin 17 (2) or apelin peptides (11, 17, 18, or 19) were given at the start of reperfusion for 10 min at a concentration of 1 pM. Left ventricular functions were obtained continuously by PowerLab system (ADInstruments, Australia). Data was reported as mean value of every 5 min. Left ventricular functions were reported as: Left Ventricular Developed Pressure (LVDP); Heart rate (HR); maximum derivative of change in systolic pressure over time (max dP/dt); minimum derivative of change in diastolic pressure over time (min dP/dt); and Rate Pressure Product (RPP).

Example 14

Elucidation of KLKB1

Isolation and Quantification of Apelin-17A2 (5) from Plasma.

Figure 13B:
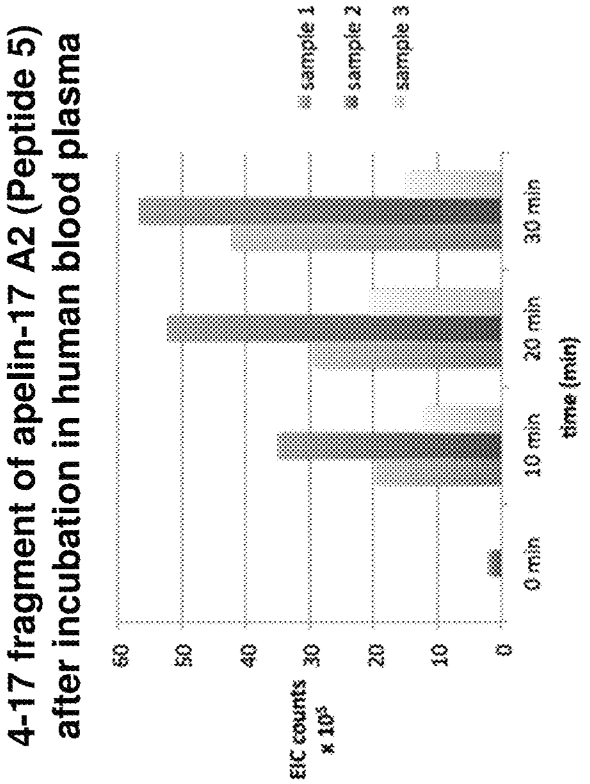
FIGS. 13 A-B show the breakdown-fragments 1-3 (FIG. 13A) and 4-17 FIG. 13B) after plasma incubation of apelin-17A2 (peptide 5).
Figure 13A:
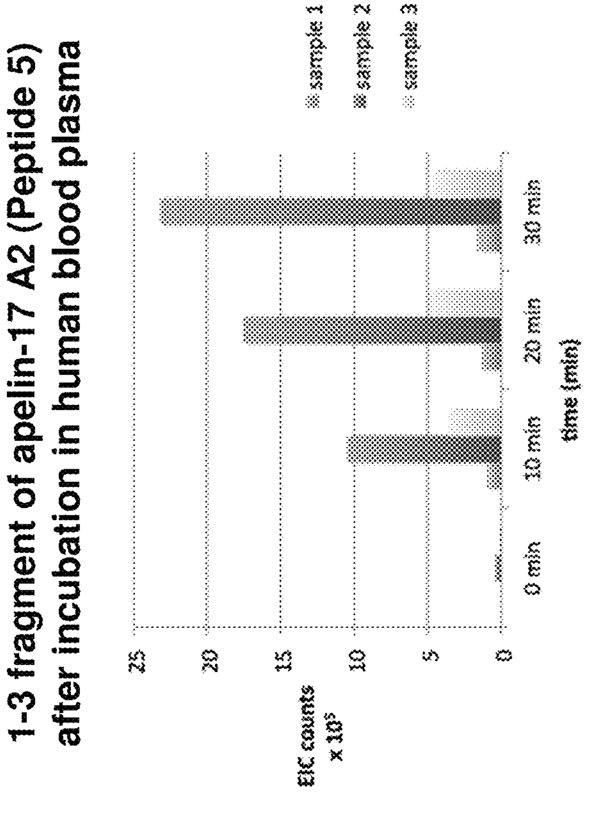
Figure 14A:
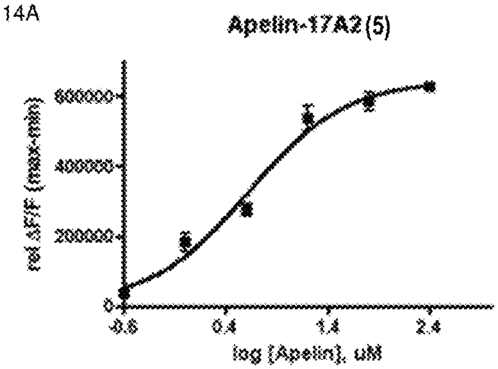
FIGS. 14A-G show the concentration response curves of apelin peptides of the certain embodiments of the disclosure.
Figure 14B:
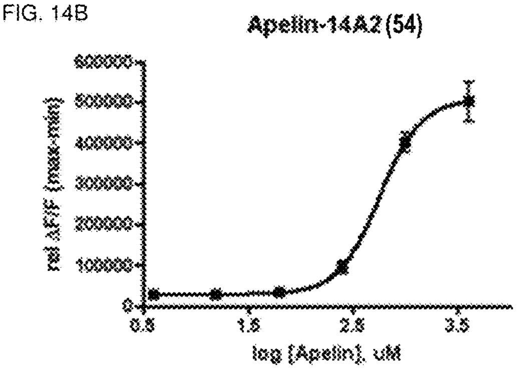
Figure 14C:
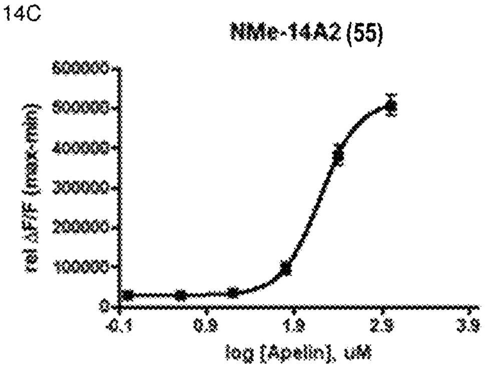
Figure 14D:
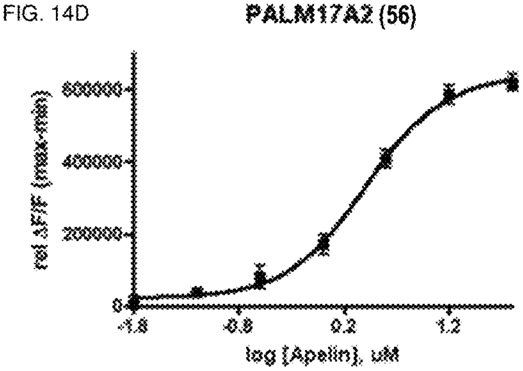
Figure 14E:
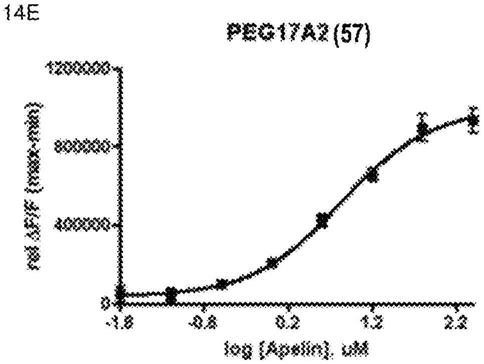
Figure 14F:
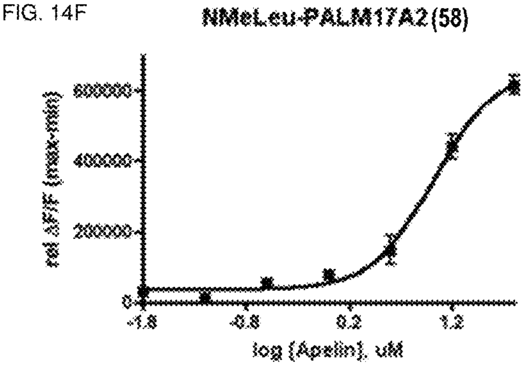
Figure 14G:
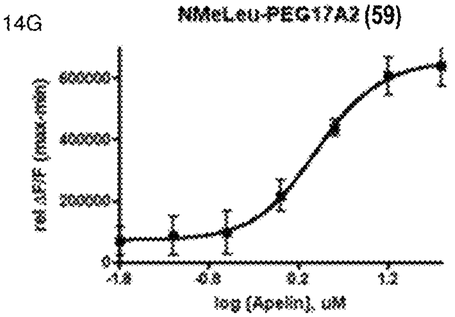
Figures 15A, 15B, 15C, 15D:
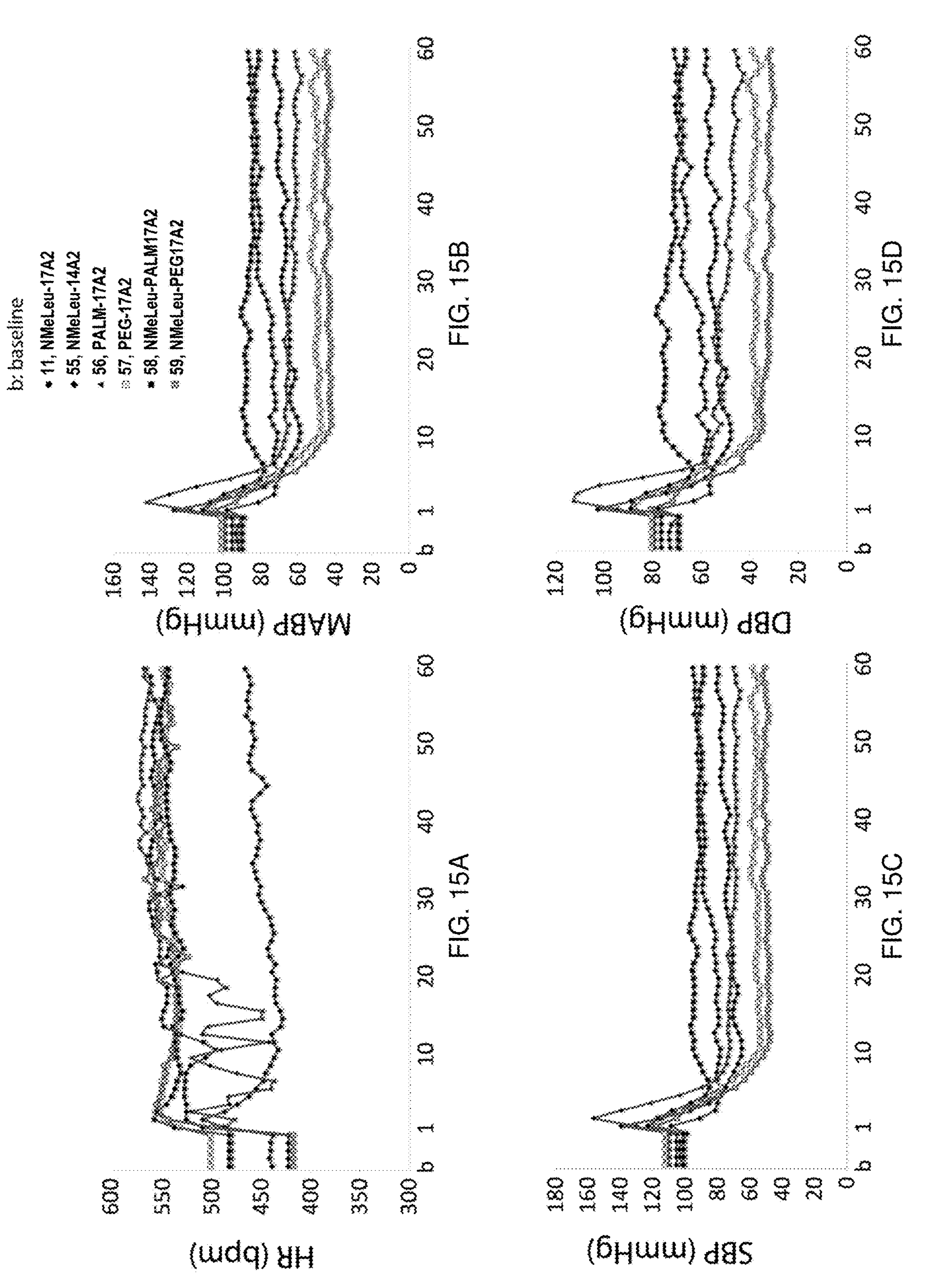
FIGS. 15A-D demostrates in vivo systolic (SBP, FIG. 15B), diastolic (DBP, FIG. 15C) and mean arterial blood pressure (MABP, FIG. 15A) and heart rate analyses (HR, FIG. 15D) following injection of Apelin-NMe17A2 (peptide 11), and apelin peptides 55-59 in anesthetized mice.

20 μL of plasma was portioned into microfuge tubes and prewarmed to 37° C. 5 μL of apelin peptide (400 μM) was added and incubated at 37° C. for varying lengths of time. Experiments were quenched by the addition of 20 μL of 10% aqueous TFA. 5 μL of internal standard (1 mM dansyl-Tyr-Val-Gly-OH) was added, and experiments were diluted up to 100 μL with 0.1% aqueous TFA. These assays were loaded onto a preequilibrated Harvard $C_{18}$-spin column (250 uL), which had previously been wet with 2×300 μL of 50% acetonitrile in 0.1% aqueous TFA and 2×300 μL of 0.1% aqueous TFA respectively, centrifuging at 300 g for 2 min between each 300 μL aliquot. Quenched plasma assays were centrifuged at 300 g until the sample was loaded. The resultant filtrate was reloaded onto the column along with 100 μL of 0.1% aqueous TFA and centrifuged at 300 g two additional times. The desired plasma peptide was washed by the addition of 2×300 μL of 0.1% aqueous TFA and centrifuged at 300 g for 2 min, discarding the filtrate after each wash. The desired peptide were eluted by the addition of 300 μL of 40% acetonitrile (human plasma) in 0.1% aqueous TFA and centrifugation at 300 g for 2 min. Eluted samples were diluted with 0.1% aqueous trifluoroacetic acid prior to analysis by $C_{18}$-RP-HPLC. To analyze the remaining percentage of 5 in plasma, incubations of 5 in plasma were immediately quenched, worked up, and analyzed by $C_{18}$ RP-HPLC, and the ratio of apelin peptide to internal standard was calculated based on the area under the peaks. This 0 min incubation ratio was used to compare the apelin peptide/internal standard ratios for the time experiments. FIG. 13 shows the breakdown-fragments (1-3 and 4-17) after plasma incubation of apelin-17A2 (compound 5).

Example 15

The kinetic parameters for the KLKB1 cleavage was determined by monitoring the decrease of parent peptide upon incubation of recombinant human KLKB1 (rhKLKB1) with native apelin-17 (2) as well as ACE2 and NEP-stabilized apelin A2 peptides 5 and 11, according to the Neprilysin Qualitative Cleavage Assays and Plasma Kallikrein KLKB1 Qualitative Cleavage Assays described herein.

Table 4 shows the kinetic parameters for NEP and KLKB1 cleavage of cardiovascular active peptides.

TABLE 4

| Substrate | Enzyme | $K_m$ (μM) | $k_{cat}$ (1/s) | $k_{cat}/K_m$ (1/Ms) |
|---|---|---|---|---|
| 2 | NEP | 190 ± 40 | 3.4 ± 0.3 | (1.8 ± 0.4) × $10^4$ |
| 2 | KLKB1 | 97 ± 21 | 13.7 ± 1.3 | (1.4 ± 0.3) × $10^5$ |
| 5 | KLKB1 | 30 ± 4 | 1.4 ± 0.2 | (4.7 ± 0.8) × $10^4$ |
| 11 | KLKB1 | 245 ± 75 | 16.5 ± 2.1 | (6.7 ± 1.0) × $10^4$ |
| Kininogen* | KLKB1 | 0.75 | 0.031 | 4.1 × $10^4$ |
| Factor XII* | KLKB1 | 2.4 | 0.001 | 4.2 × $10^2$ |

*Data obtained from Gozzo, A. J. et.al.; "Heparin modulation of human plasma kallikrein on different substrates and inhibitors;" *Biol. Chem.* 2006, 387, 1129-1138.

The KLKB1 cleavage kinetics are similar to those of neprilysin (NEP), which cleaves within the critical 'RPRL'-motif, thereby inactivating apelin. KLKB1 processes apelin-17 (2) and peptides 5 and 11 with moderate efficiency ($k_{cat}/K_m$~$10^5$), comparable to other cardiovascular active peptide substrates. As the potent peptide 11, which is resistant to ACE2 and neprilysin, is degraded quickly, this stimulated an endeavor to explore a stabilization strategy closer to the Arg3-Arg4 cleavage site.

Example 16

Synthesis of Apelin-14A2 (54)

Resin bound BrF was subjected to manual SPPS, introducing amino acids in the following order: Fmoc-Aib-OH, Fmoc-Nle-OH, Fmoc-Pro-OH, Fmoc-Gly-OH, Fmoc-Lys(Boc)-OH, Fmoc-His(Trt)-OH, Fmoc-Ser(t-Bu)-OH, Fmoc-Leu-OH, Fmoc-Arg(Pbf)-OH, Fmoc-Pro-OH, Fmoc-Arg(Pbf)-OH, Fmoc-Glu(Trt)-OH, Fmoc-Arg(Pbf)-OH). A portion (0.05 mmol) of resin-bound peptide was cleaved as previously described and purified using a C18 RP-HPLC analytical column (method A), eluting at 14.4 min. The desired peptide was isolated as a white solid after lyophilization (9.0 mg, 11%). Monoisotopic MW (MALDI-TOF) calculated for $C_{75}H_{124}BrN_{27}O_{17}$ 1753.9, found $[M+H]^+$ 1753.6.

Example 17

Synthesis of Apelin-NMe14A2 (55)

Resin bound BrF was subjected to manual SPPS, introducing amino acids in the following order: Fmoc-Aib-OH, Fmoc-Nle-OH, Fmoc-Pro-OH, Fmoc-Gly-OH, Fmoc-Lys(Boc)-OH, Fmoc-His(Trt)-OH, Fmoc-Ser(t-Bu)-OH, Fmoc-Arg($Boc_2$)-NMeLeu-OH,[12] Fmoc-Pro-OH, Fmoc-Arg(Pbf)-OH, Fmoc-Glu(Trt)-OH, Fmoc-Arg(Pbf)-OH). A portion (0.05 mmol) of resin-bound peptide was cleaved as previously described and purified using a C18 RP-HPLC analytical column (method A), eluting at 14.7 min. The desired peptide was isolated as a white solid after lyophilization (7.5 mg, 9%). Monoisotopic MW (MALDI-TOF) calculated for $C_{76}H_{127}BrN_{27}O_{17}$ 1768.9, found $[M+H]^+$ 1768.7.

Example 18

Synthesis of PALM-17A2 (56)

Compound 54 was extended by SPPS, introducing amino acids in the following order: Fmoc-Arg(Pbf)-OH, Fmoc-Phe-OH, Fmoc-Lys(Boc)-OH, palmitic acid. A portion (0.05 mmol) of resin-bound peptide was cleaved as previously described and purified using a BiPhe RP-HPLC analytical column (method A), eluting at 25.8 min. The desired peptide was isolated as a white solid after lyophilization (5.0 mg, 8%). Monoisotopic MW (MALDI-TOF) calculated for $C_{112}H_{188}BrN_{34}O_{21}$ 2424.4, found $[M+H]^+$ 2423.9.

Example 19

Synthesis of PEG-17A2 (57)

Compound 54 was extended by SPPS, introducing amino acids in the following order: Fmoc-Arg(Pbf)-OH, Fmoc-Phe-OH, Fmoc-Lys(Boc)-OH, Fmoc-$(PEG)_6$ propionic acid. A portion (0.05 mmol) of resin-bound peptide was cleaved as previously described and purified using a BiPhe RP-HPLC analytical column (method A), eluting at 25.6 min. The desired peptide was isolated as a white solid after lyophilization (6.5 mg, 9%). Monoisotopic MW (MALDI-TOF) calculated for $C_{126}H_{197}BrN_{35}O_{29}$ 2743.4, found $[M+H]^+$ 2743.2.

Example 20

Synthesis of PALM-NMe17A2 (58)

Compound 55 was extended by SPPS, introducing amino acids in the following order: Fmoc-Arg(Pbf)-OH, Fmoc-Phe-OH, Fmoc-Lys(Boc)-OH, palmitic acid. A portion (0.05 mmol) of resin-bound peptide was cleaved as previously described and purified using a BiPhe RP-HPLC analytical column (method A), eluting at 17.2 min. The desired peptide was isolated as a white solid after lyophilization (5.5 mg, 7%). Monoisotopic MW (MALDI-TOF) calculated for $C_{113}H_{190}BrN_{34}O_{21}$ 2438.4, found 2438.0.

Example 21

Synthesis of PEG-NMe17A2 (59)

Compound 55 was extended by SPPS, introducing amino acids in the following order: Fmoc-Arg(Pbf)-OH, Fmoc-Phe-OH, Fmoc-Lys(Boc)-OH, Fmoc-$(PEG)_6$ propionic acid. A portion (0.05 mmol) of resin-bound peptide was cleaved as previously described and purified using a BiPhe RP-HPLC analytical column (method A), eluting at 17.1 min. The desired peptide was isolated as a white solid after lyophilization (6.5 mg, 8%). Monoisotopic MW (MALDI-TOF) calculated for $C_{127}H_{199}BrN_{35}O_{29}$ 2757.4, found 2757.4.

Example 22

In Vitro Stability Tests

The in vitro KLKB1 and NEP stability of the PALM/PEG peptides 56-59 was compared to native apelin-17 (2), the A2 substituted peptide 5 and the NEP-resistant peptide 11. Peptides 56-59 were incubated with KLKB1 (rhKLKB1, Novoprotein) or recombinant human NEP (rhNEP, Sino Biological) at 37° C. for up to 72 h.

Plasma Kallikrein KLKB1 Qualitative Cleavage Assays

Native apelin-17 (2) and apelin peptides 5, 56, 57, 58 and 59 were dissolved in Milli-Q water (1 mM). Human plasma kallikrein KLKB1 were each reconstituted in Tris buffer (100 mM TrisHCl, 10 mM $CaCl_2$), 150 mM NaCl) and diluted with Tris buffer (50 mM TrisHCl, 250 mM NaCl) to give a KLKB1 concentration of 2 ng/pL. The KLKB1 enzyme was then preincubated at 37° C. for 10 minutes prior to the addition of 5 μL of apelin peptide (1 mM). Aliquots (1 μL) were taken at 1, 2, 4, 6, 12, 24, 36, and 48 hours and analyzed with MALDI-TOF mass spectrometry to qualitatively determine the time point at which degradation products could be observed (Table 4).

Neprilysin Qualitative Cleavage Assays

Native apelin-17 (2) and apelin peptides 5, 54, 56, 57, 58 and 59 were dissolved in Milli-Q water (1 mM). Recombinant Human Neprilysin (rhNEP, Sino Biological) was reconstituted in Tris buffer (100 mM Tris, 100 mM NaCl, 10 mM $ZnCl_2$, pH 7.5). To initiate the assays, rhNEP was diluted in Tris buffer to a 2 ng/μL final concentration, and pre-incubated at 37° C. for 10 minutes prior to the addition of 5 μL of apelin peptide (1 mM). Aliquots (1 μL) were taken at 1, 2, 4, 6, 12, 24, 36, and 48 hours and analyzed with MALDI-TOF mass spectrometry to qualitatively determine the time point at which degradation products could be observed. Table 5 shows the timepoints at which degradation products of apelin peptides could first be observed through MALDI-TOF after incubation with KLKB1 and Neprilysin.

TABLE 5

| Peptide | Modification | Degradation Onset Timepoint with NEP | Degradation Onset Timepoint with KLKB1 |
|---|---|---|---|
| 2 | Apelin-17 | <30 min | <30 min |
| 5 | Apelin-17A2 | <1 hr | <30 min |
| 54 | Apelin-14A2 | >36 hr | — |
| 56 | PALM-17A2 | 1 hr | 1 hr |
| 57 | PEG-17A2 | 12 hr | 1 hr |
| 58 | PALM-NMe17A2 | >36 hr | 2 hr |
| 59 | PEG-NMe17A2 | >36 hr | 2 hr |

Quantitative Degradation Assays (Kinetics)

The extent of degradation was analyzed via LC-MS because of the overlapping elution patterns of peptide fragments (NEP).

Native apelin-17 (2) and apelin peptides 5, 54, 56, 57, 58 and 59 were dissolved in Milli-Q water (1 mM). Recombinant human neprilysin (rhNEP, Sino Biological) was reconstituted in Tris buffer (100 mM Tris, 100 mM NaCl, 10 μM $ZnCl_2$, pH 7.5). To initiate the assay, rhNEP was diluted in Tris buffer (3.1 nM final concentration) and preincubated at 37° C. for 10 min prior to the addition of 5 μL of apelin peptide (1 mM) and 1.5 μL of internal standard dansyl-Tyr-Val-Gly-OH (1 mM). Aliquots (10 μL) were removed at 0, 1, 4, 24, and 72 h, quenched with 0.1 M EDTA (10 μL), diluted to 100 μL with Milli-Q water, and analyzed by LC-MS. Assays were performed in triplicate (n=3) for each time point. Integrated peak areas of the parent apelin peptide and internal standard derived from LC-MS analyses were extracted using Mass Hunter software (version B.04.00) and compared in positive extracted ion count modus (+EIC). The extent of proteolysis was determined by comparing the initial (0 h) ratio of the integrated extracted ions of the parent apelin peptide to the internal dansyl-YVG standard (apelin/dansyl-YVG) to the same ratio at the different assay time points. The decrease in apelin/dansyl-YVG ratio was converted to a percentage of cleaved peptide over time.

Ca2+ Mobilization Assay

To study the extent to which the newly derived peptides trigger APJ-receptor activation, a fluorescence coupled calcium release assay including a recombinant human APJ-Gα16 receptor cell line was used.

Chem-5-APJ cells (Millipore, USA) were seeded (30 000 cells/well) into Nunclon Delta Surface 96-well, clear-bottom microtitre plates (Thermo Scientific, Denmark) 24 hours prior to assay. Cells were loaded for 1 hour with FLIPR Calcium 6-QF fluorescent indicator dye (Molecular Devices, USA) in assay buffer [Hanks balanced salt solution (HBSS), 20 mM HEPES, 0.2% DMSO, 2.5 mM probenecid, pH 7.6], washed three times with assay buffer, then returned to the incubator for 10 min before assay on a fluorimetric imaging plate reader (FLIPR; Molecular Devices, Sunnyvale, Calif., USA). Maximum change in fluorescence over baseline was used to determine agonist response. Dose—response curve data were fitted to a four-parameter logistic equation using PRISM (Graph Pad, USA) from which pEC50 values were calculated. FIGS. 14A-G show the concentration response curves of apelin peptides. Table 6 shows the peptide half-life and receptor activation of studied Apelin peptides.

TABLE 6

| Apelin | Modification | $t_{1/2}$ (rhNEP, h) | $t_{1/2}$ (rhKLKB1, h) | $t_{1/2}$ (hplasma, h) | $EC_{50}$ (nM) |
|---|---|---|---|---|---|
| 2 | Apelin-17 | 0.4 | 0.4 | 0.02 | N.D. |
| 5 | Apelin-17A2 | 1.0 | 0.7 | 0.3 | 4.0 ± 0.2 |
| 11 | NMeLeu-17A2 | >30 | 0.9 | 1.2 | N.D. |
| 54 | Apelin-14A2 | — | — | — | 568 ± 34 |
| 55 | NMeLeu-14A2 | — | — | — | 176 ± 21 |
| 56 | PALM-17A2 | 1.5 | 1.0 | 4.5 | 2.6 ± 0.2 |
| 57 | PEG-17A2 | >30 | 1.4 | 18 | 6.3 ± 0.4 |
| 58 | NMeLeu-PALM17A2 | >30 | 2.1 | 20.5 | 11.3 ± 2.1 |
| 59 | NMeLeu-PEG17A2 | >30 | 2.9 | 27 | 2.5 ± 0.2 |

Compounds 56-59 feature EC50 values in the low nanomolar range comparable to the N-terminally free apelin-17A2 peptide (i.e., compound 5). Unlike palmitoylation within the apelin peptide sequence, which can be detrimental for receptor binding (Juhl, et al., "Development of potent and metabolically stable APJ ligands with high therapeutic potential;" *ChemMedChem* 2016, 11, 2378-2384.), N-terminal extension by a palmitoyl or PEG chain seems not to affect receptor binding and internalization. Surprisingly, the 14-mer left after the KLKB1 cut (i.e., compound 54 and 55), seems to be rather inactive featuring a 200-times higher EC50 than the 17-mers.

Example 23

Physiological Test—Blood Pressure Assays

Apelin peptides 11, 56-59 as well as the KLKB1-cleavage fragments 54 and 55 were tested for blood pressure lowering abilities in anesthetized mice.

Mice were anesthetized with 1.5% isoflurane/oxygen, and body temperature was monitored and maintained at 36° C. by a heating pad. The aorta was cannulated via the right carotid artery using a PV loop catheter (model 1.2F from Scisense, Transonic) in order to continuously record arterial blood pressure and heart rate (LabScribe 2.0, Scisense). Compounds 11, and 54-59 or 55-59 (1.4 μM/kg body weight) or the same volume of saline was injected via the right jugular vein. Results are reported as systolic blood pressure (SBP), diastolic blood pressure (DBP), mean arterial blood pressure (MABP), and heart rate (HR) shown in FIGS. 15A-D.

Figure 16A:
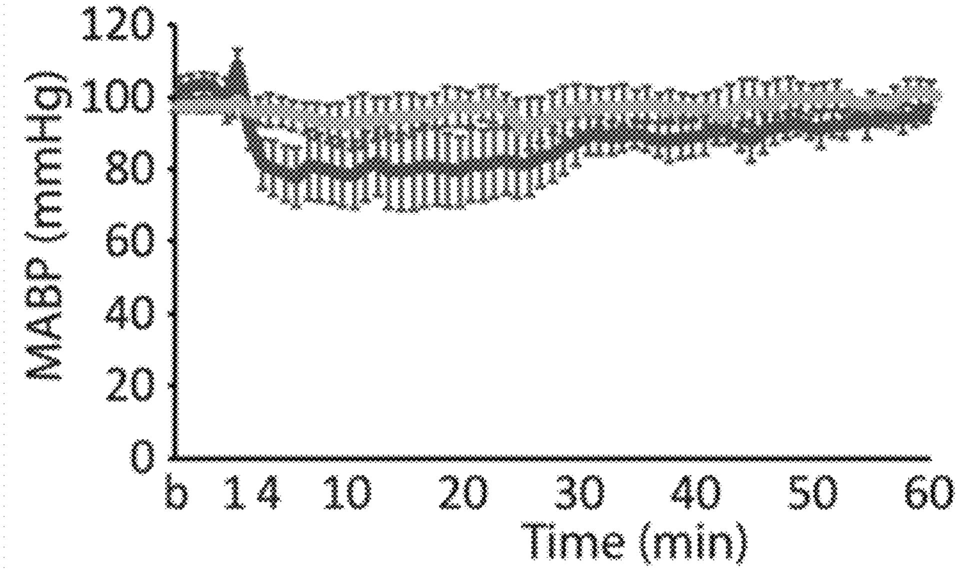
FIGS. 16A-B demostrates blood pressure data of KLKB1 fragments 54 and 55.
Figure 16B:
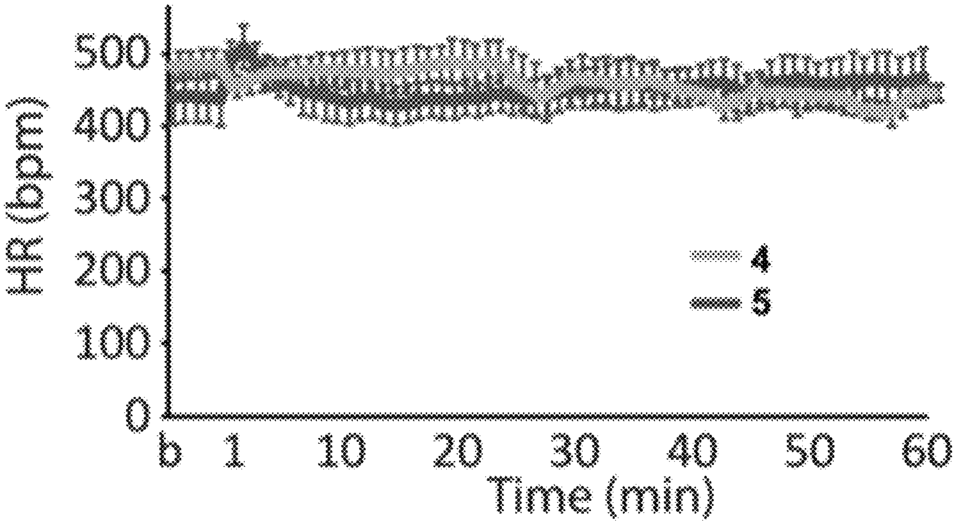

Apelin peptides were delivered systemically via the right internal jugular vein while blood pressure (BP) and heart rate (HR) were continuously monitored in the aorta cannulated via the right carotid artery. All N-terminally extended apelin peptides, except 58, show pronounced and time-stable blood pressure lowering effects (FIGS. 15*a-d*). Among the synthesized peptides 56-59, peptide 58 triggers also the lowest $Ca^{2+}$ mobilization (Table 5). Interestingly, the heart rate increasing effect is restored in this peptide 58, suggesting alternative activation pathways. In this regard, peptides 56, 57 and 59 are more potent than apelin-17 (2) and apelin-17A2 (5). Importantly, both PEGylated peptides 57 and 59 show the most stable and potent effect. In contrast, both the fragments left after KLKB1 cleavage (peptides 54 and 55) are inactive or nearly so in their cardio-physiological effects (FIGS. 16A-B). This correlates with the results obtained from the $Ca^{2+}$ mobilization assay.

Human plasma kallikrein (KLKB1) has been identified as human protease that cleaves apelin-17 relatively quickly between Arg3-Arg4. The resulting C-terminal 14-mer appears to be poor with regard to $Ca^{2+}$ mobilization (APJ receptor activation capacity) and is lacking beneficial cardio-physiological effects. Hence KLKB1 degradation inactivates apelin 17. N-terminally extension by a palmitoyl or $PEG_6$ chain yields apelin peptides that are more cleavage resistant towards both KLKB1 and NEP proteases and have prolonged plasma half-life. Combined with their potent and prolonged blood pressure lowering effect, these new apelin peptides present a promising new target for the development of cardiovascular active peptide drugs. Further physiological studies and other synthetic stabilization approaches are currently underway to obtain a better understanding of the impact of this new cleavage site for the design of novel drug targets.

Example 24

Cardiac Allograft Vasculopathy

Figure 17A:
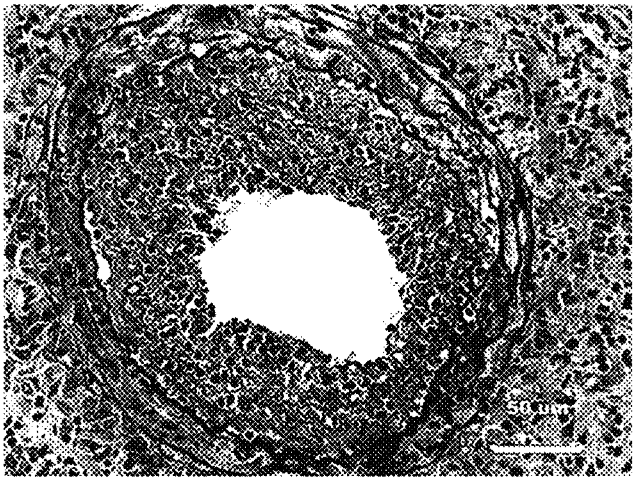
FIG. 17A-B are micrographs of the cross-sectional area of the intimal/lumen with Verhoeff-van Gieson-stained saline-treated control carrier compared to an apelin peptide (11) treated coronary arteries.
Figure 17B:
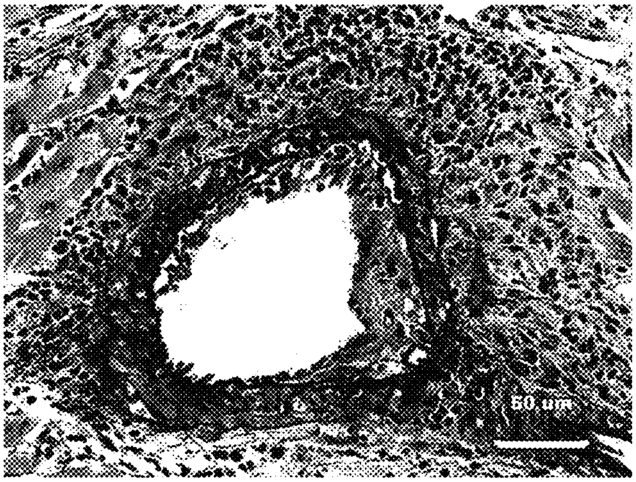
Figure 18:
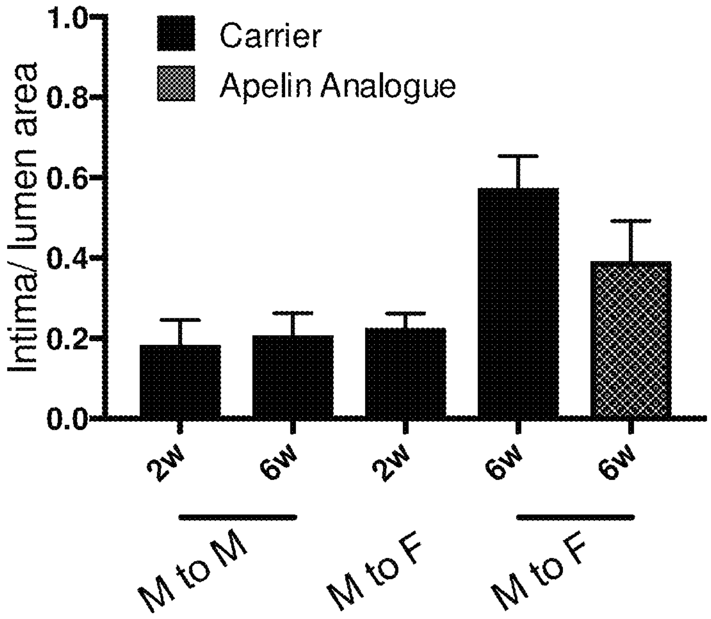
FIG. 18 is a bar chart of showing the ratio of luminal/lumen areas for coronary arteries 2 and 6 weeks after heart transplant of the model.
Figure 19:
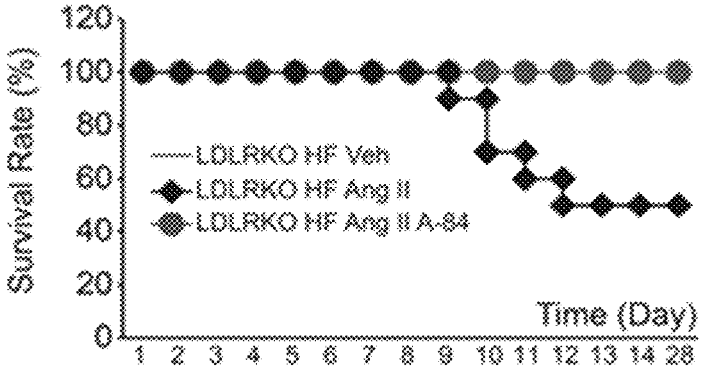
FIG. 19 is a curve showing the survival rate of mortality due to aortic rupture in the indicated groups.
Figure 20:
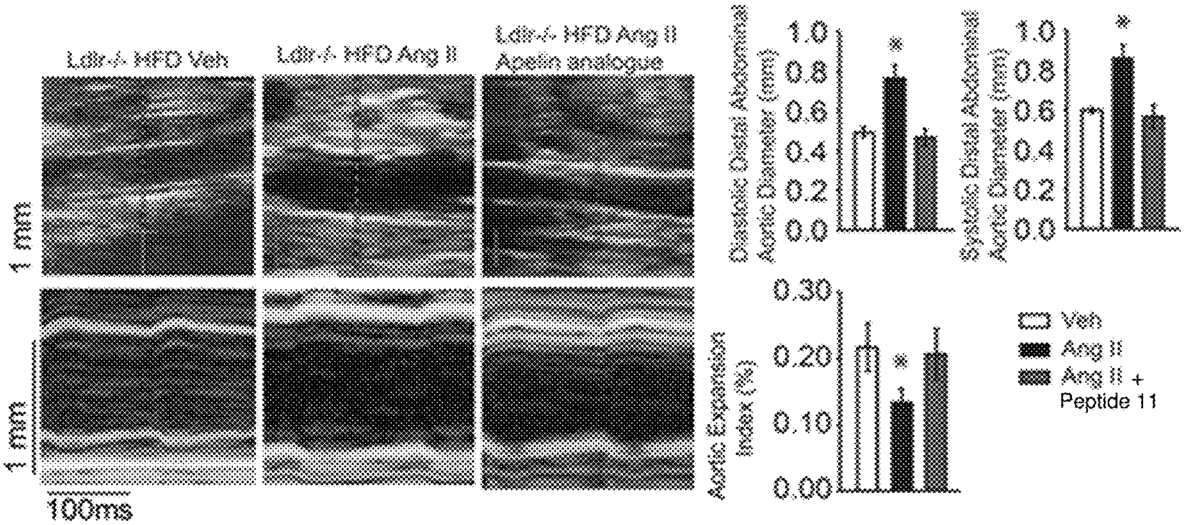
FIG. 20 shows representative ultrasound images of the abdominal aorta and averaged measurement for abdominal aorta diameter (during systole and diastole), and Aortic Expansion Index, a measure of aortic wall compliance in Ldlr$^{-/-}$ mice that received vehicle or Ang II for 4 weeks, or Ang II+ apelin peptide 11. n=8 per group.
Figure 21:
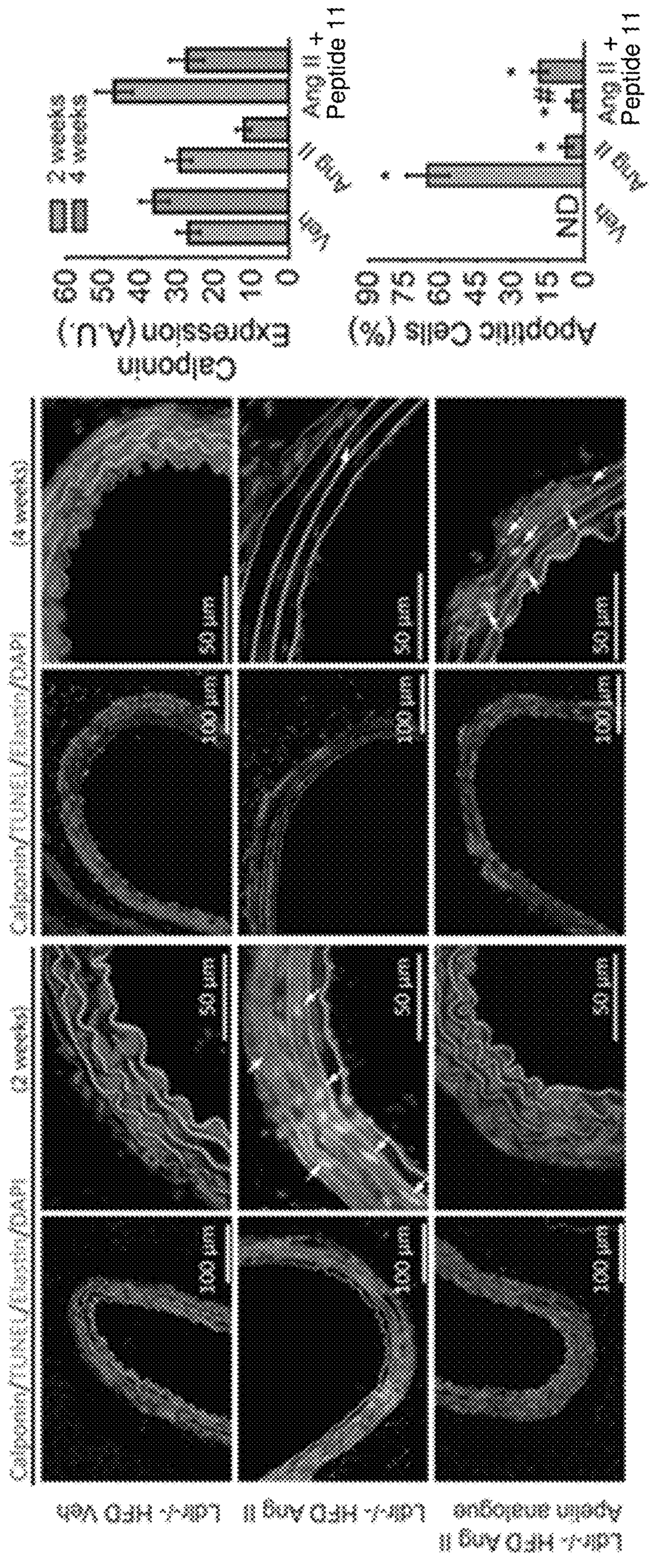
FIG. 21 shows representative images of immunostaining for abdominal aorta sections for calponin (SMC, red), TUNEL (green), DAPI (blue) and elastin fibers' autofluorescence (green) in the indicated group. Averaged quantification for Calponin levels (measure of viable SMCs), and apoptotic cells (TUNEL-positive) for each group is shown on the right.
Figure 22:
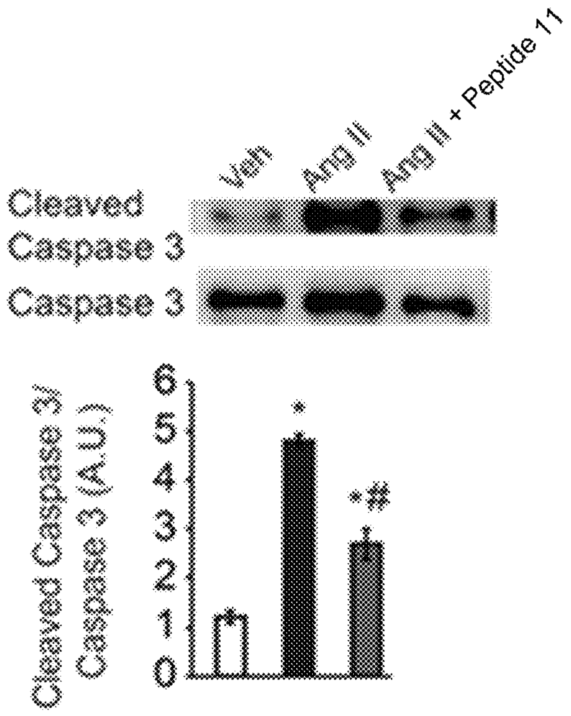
FIG. 22 shows representative Western blot for cleaved and total caspase 3, and averaged cleaved-to-total ratio for Caspase 3.
Figure 23:
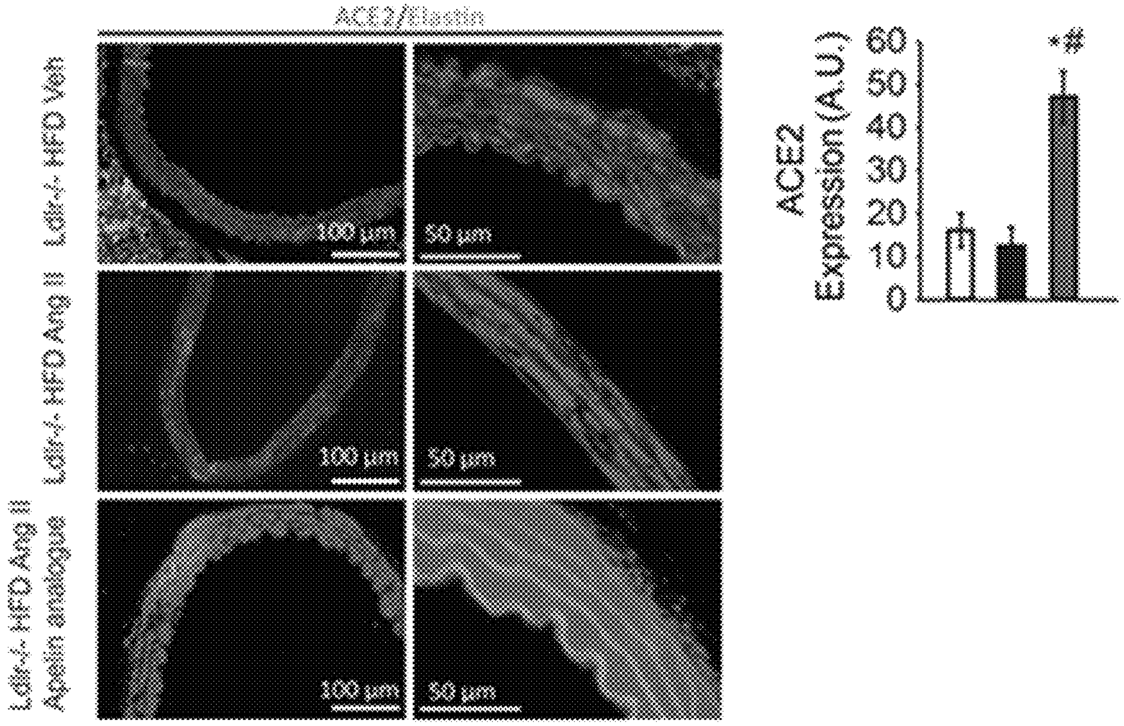
FIG. 23 shows representative immunostaining for ACE2 and averaged quantification in the abdominal aorta of Ldlr$^{-/-}$ mice receiving saline, Ang II or Ang II+ apelin peptide 11, n=6 per group.
Figure 24:
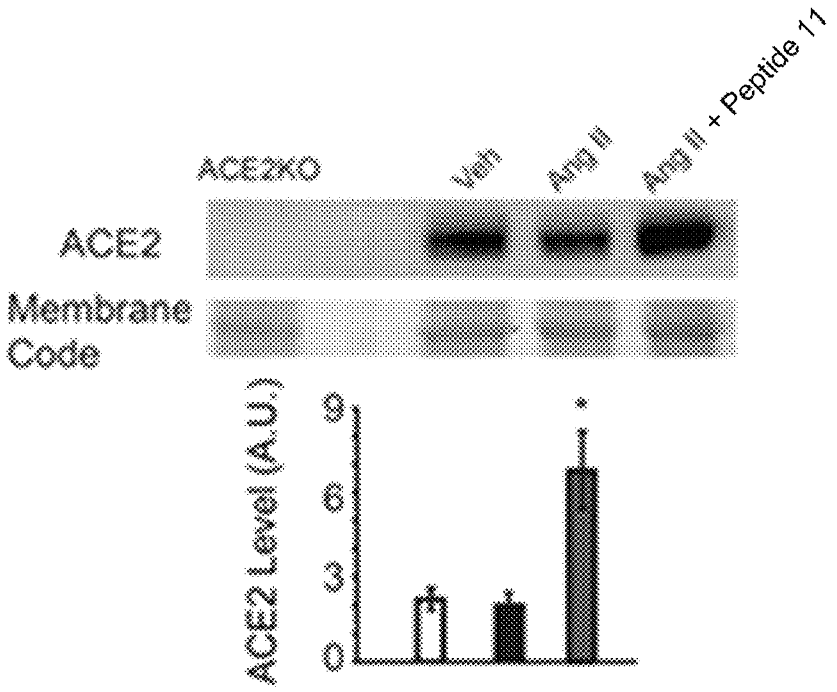
FIG. 24 shows DHE fluorescence and NADPH oxidase activity showing suppression of oxidative stress by the apelin peptide 11. *$p<0.05$ compared to vehicle group. A.U.=arbitrary units. Averaged values represent Mean±SEM.
Figure 25:
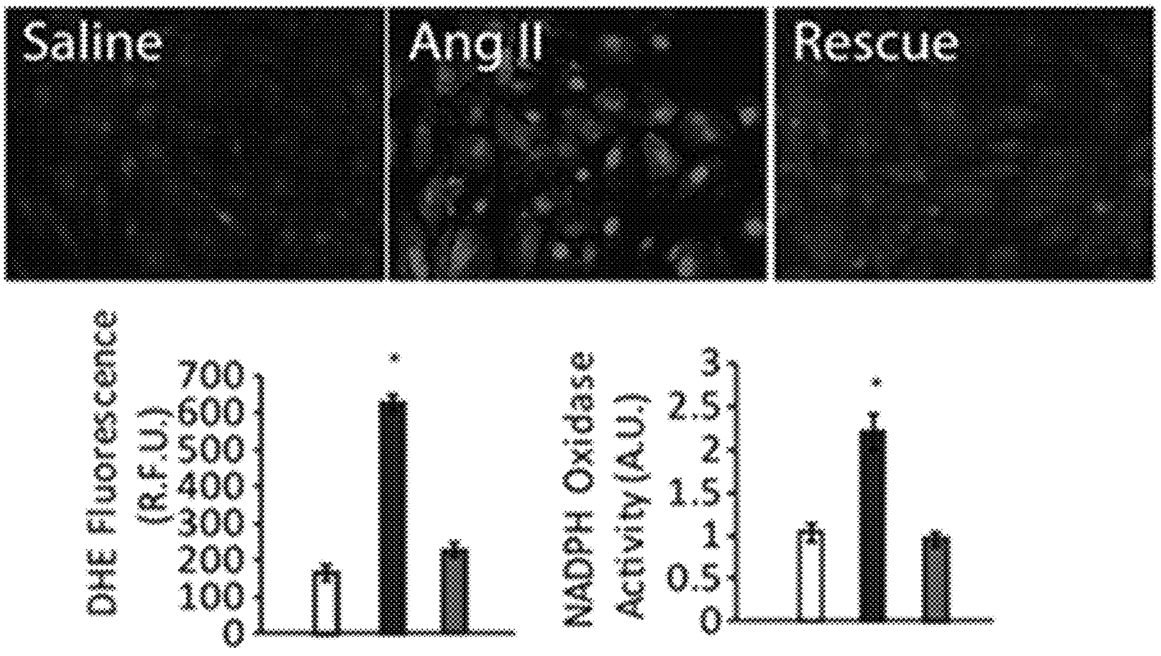

B6 male hearts were transplanted heterotopically into male or female B6 of the recipient mice, starting 2 weeks after transplant. Synthesized apelin peptide (Apelin-NMe17A2) (11), was given by daily intraperitoneal injection (3 mg/kg/d) for 4 weeks. Female mice raise immune response against the male HY antigen, injure the coronary arteries of the transplanted heart based on Verhoeff-Van Gieson staining (FIG. 17) leading to progressive expansion of the arterial intima occluding the arterial lumen (FIG. 18). Treatment with apelin peptide mitigates arteriopathy vs saline-treated carrier controls (a-b). *$p<0.05$ compared with carrier/placebo group. n=6; M=male; F=female. The results demonstrate that treatment with apelin peptides of the present invention may protect against transplant arteriopathy.

C57BL/6J mice were purchased from Jackson Laboratories. The C57BL/6 mice subjected to surgery were 11-14 weeks old. All animal experiments were carried out according to the Canadian Council on Animal Care Guidelines. Animal protocols were approved by the Animal Care and Use Committee at the University of Alberta. Hearts from 12-14 weeks male wild-type (WT) donors were transplanted heterotopically to the abdomen of the female WT recipients. The inferior and superior vena cavae, and the pulmonary veins of the donor heart were ligated. Then the donor aorta and pulmonary artery were anastomosed to the recipient's abdominal aorta and inferior vena cava, below the renal arteries. Cardiac allograft vasculopathy (CAV) was induced due to the presence of HY-minor histocompatibility antigen-directed, cell-mediated allo-immune response against the male donor hearts. The heart grafts were harvested six weeks after transplantation. Intima area, endothelial loss in medium to large-sized arteries, inflammatory cellular infiltration, microvasculature density and tip cell markers using Immunohistochemistry and qPCR were characterized.

Example 25

Apelin Peptide Prevents Angiotensin II-Induced Aortic Abdominal Aneurysm

Experimental Animals and Protocols. Male LDL receptor deficient ($Ldlr^{-/-}$) mice were generated and bred in C57BL/6 background. All animal experiments were carried out in accordance with the Canadian Council on Animal Care Guidelines, and animal protocols were reviewed and approved by the Animal Care and Use Committee at the University of Alberta.

Angiotensin II (Ang II) and Phenylephrine (PE) Infusion In Vivo.

Alzet micro-osmotic pump (model 1002 or 1004; Durect Co.) was implanted subcutaneously at the dorsum of the neck to infuse Ang II (1.5 $mg/kg^{-1}d^{-1}$) or vehicle (saline) for 28 days in high fat fed $Ldlr^{-/-}$ mice.

Histological Analyses, Terminal Deoxynucleotidyl Transferase dUTP Nick End Labeling (TUNEL) and Immunofluorescence Staining.

After 4 weeks of Ang II or saline infusion, mice underwent whole body perfuse-fixation, via the left ventricle, with 10% buffered formalin (80 mmHg, 20 min). Third order mesenteric arteries were dissected out carefully without being forced or over stretched, preserved in 10% buffered formalin for 48 hours and embedded in paraffin. Aortas were dissected, imaged for gross morphological assessment, then fixed in formalin and paraffin-embedded. Five micrometer thick formalin fixed paraffin embedded (FFPE) sections of aortas and mesenteric arteries were stained for Movat's pentachrome and Gomori Trichrome to evaluate morphological alternations. Collagen positive area was quantified by the morphometric analysis using the Metamorph Basic (version 7.7.0.0) software. In situ DNA fragmentation was detected in 5-μm thick FFPE sections of aorta using the commercially available terminal deoxynucleotidyl transferase-mediated dUTP nick-end labeling (TUNEL) assay kit according to manufacturer's instructions (Invitrogen) as previously described. Five-micrometer thick FFPE sections were also used for the immunofluorescence staining for ACE2, calponin and apelin. Thickness of the medial layer of the aorta was measured in calibrated images as the mean distance between the external elastin lamella and the internal elastin lamella from 8 randomly selected fields of the cross-section of an aorta using the Metamorph Basic software (version 7.7.0). Calponin positive cells in the aorta were quantified to estimate the VSMC density.

Dihydroethidium (DHE) Staining and Nicotinamide Adenine Dinucleotide Phosphate (NADPH) Oxidase Activity Assay.

For DHE and NADPH staining, fresh aortas were collected (without perfuse-fixation) and preserved in OCT at −80° C. Nicotinamide adenine dinucleotide phosphate (NADPH) oxidase activity in human or mice primary aortic VSMCs was quantified by lucigenin enhanced chemiluminescence using a single-tube luminometer (Berthold FB12, Berthold Technologies, Germany) modified to maintain the sample temperature at 37° C. as previously described. Briefly, after three times of wash in ice-cold phosphate buffered saline (PBS) with protease and, VSMCs or OCT-embedded aorta sections were lysed with RIPA buffer containing protease and phosphatase inhibitor cocktails. NADPH (1 mM) and Lucigenin (50 μM) were added to 100 μg of protein extracts in the presence or absence of diphenylene iodonium (DPI; 10 μM), a selective inhibitor of flavin-containing enzymes including NADPH Oxidase. Light emission was measured every 1 second during a 5-minute period using a single-tube luminometer (Berthold FB12, Berthold Technologies, Germany) at 37° C. The emission over a 3-minute period was averaged for each sample.

Dihydroethidium (DHE) staining was performed on aortic SMCs and OCT-embedded aorta sections and visualized under fluorescence microscope (Olympus IX81). For SMCs, after 1 hour of incubation with or without Ang II (1 μM), cells were incubated with DHE (20 μM DHE, final concentration in culture media; Sigma Aldrich) at 37° C. for 30 minutes in dark. Fluorescence images were subsequently captured with a fluorescence microscope (IX81, Olympus) after washing with PBS. Quantitative measurements of DHE fluorescence intensity were carried out using Metamorph Basic (version 7.7.0.0), regions congruent to the cell nuclei boundaries were drawn, the average pixel intensities were calculated and corrected by subtracting the background, and reported here as DHE fluorescence.

Ultrasonic Vasculography.

Ultrasonic images of the aortas were obtained in mice anesthetized with 1.5% isoflurane using a Vevo 2100 high resolution-imaging system equipped with a real time micro-visualization scan head (RMV 704, Visual Sonics, Toronto, Canada). The aortic diameters were measured by M-mode at thoracic aorta, aortic arch and abdominal aorta. The maximum aortic lumen diameter (corresponding to cardiac systole) and the minimum aortic lumen diameter (corresponding to cardiac diastole) recordings were measured and used to calculate the aortic expansion index [(systolic aortic diameter-diastolic aortic diameter)/systolic diameter×100].

Western Blot Analysis.

Protein was extracted from aorta using RIPA lysis buffer containing protease and phosphatase inhibitor cocktails, and quantified using the BCA Protein Array Kit (Pierce, Rockford, Ill.). Equal amounts of protein extracts were loaded and separated by SDS-PAGE gel and then transferred to polyvinylidene fluoride (PVDF) membranes. The membranes were blocked for 1 hour at room temperature with 5% skim milk in TBST, and then incubated with primary antibodies overnight at 4° C., followed by HRP-linked secondary antibodies. The probed proteins were detected with Amersham ECL Prime detection reagent and visualized with ImageQuant LAS 4000 Mini Biomolecular Imager (GE Healthcare, Baie-d'Urfé, QC, Canada). The expression levels of target proteins were quantified by densitometry using the equipped software. Equal loading of protein was confirmed by staining the membrane with Pierce™ Reversible Protein Stain Kit for PVDF Membranes (ThermoFisher Scientific, USA).

Apelin Peptide and Aortic Aneurysm.

Male $Ldlr^{-/-}$ mice (Jackson Lab) received high fat diet (Envigo TD.88137) at 8 weeks of age and throughout the study. One week after initiating high fat diet, osmotic pumps (Model 1004, Alzet) were implanted subcutaneously to deliver Angiotensin II (Sigma-Aldrich) at a rate of 1.5 mg/kg/d for 28 days. Synthesized apelin peptide 11 was given by daily intraperitoneal injection (3 mg/kg/d) for 28 days.

The data is shown in FIGS. 19-25. As shown in these Figures, NEP-resistant apelin peptide 11 (Apelin-NMe17A2) markedly prevented the formation of abdominal aortic aneurysm suggesting that apelin peptides represents a new class of drugs for this condition which currently has no current medical therapy.

What is claimed is:

1. A peptidomimetic of Formula (I):

Z1-pGlu-aa2-aa3-aa4-aa5-aa6-aa7-aa8-aa9-aa10-aa11-aa12-aa13, or pharmaceutically acceptable salts thereof, wherein Z1 is H or a long chain moiety;

wherein each of aa2, aa3, aa4, aa5, aa6, aa7, aa8, aa9, aa10, aa11, aa12, and aa13 is independently an amino acid, wherein:

aa2 comprises Arg or a conservative variant thereof;

aa3 comprises Pro or a conservative variant thereof;

aa4 comprises an amino acid or a conservative variant thereof selected from the group consisting of Arg, Arg-D, αMeArg and azaArg;

aa5 comprises an amino acid or a conservative variant thereof selected from the group consisting of Leu, NMeLeu, αMeLeu and azaLeu;

aa6 comprises Ser or a conservative variant thereof;

aa7 comprises His or a conservative variant thereof;

aa8 comprises Lys or a conservative variant thereof;

aa9 comprises Gly or a conservative variant thereof;

aa10 comprises Pro or a conservative variant thereof;

aa11 is comprises Nle or a conservative variant thereof, wherein Nle is norleucine;

aa12 is comprises Aib or a conservative variant thereof, wherein Aib is α-aminoisobutryic acid; and aa13 is comprises paraBrPhe or a conservative variant thereof.

2. The peptidomimetic of claim 1, wherein aa2-aa3-aa4-aa5-aa6-aa7-aa8-aa9-aa10-aa11-aa12-aa13 is Arg-Pro-Arg-D-Leu-Ser-His-Lys-Gly-Pro-Nle-Aib-paraBrPhe.

3. The peptidomimetic of claim 1, wherein aa2-aa3-aa4-aa5-aa6-aa7-aa8-aa9-aa10-aa11-aa12-aa13 is Arg-Pro-Arg-NMeLeu-Ser-His-Lys-Gly-Pro-Nle-Aib-paraBrPhe.

4. The peptidomimetic of claim 1, wherein aa2-aa3-aa4-aa5-aa6-aa7-aa8-aa9-aa10-aa11-aa12-aa13 is Arg-Pro-αMeArg-Leu-Ser-His-Lys-Gly-Pro-Nle-Aib-paraBrPhe.

5. The peptidomimetic of claim 1, wherein aa2-aa3-aa4-aa5-aa6-aa7-aa8-aa9-aa10-aa11-aa12-aa13 is Arg-Pro-Arg-αMeLeu-Ser-His-Lys-Gly-Pro-Nle-Aib-paraBrPhe.

6. The peptidomimetic of claim 1, wherein aa2-aa3-aa4-aa5-aa6-aa7-aa8-aa9-aa10-aa11-aa12-aa13 is Arg-Pro-azaArg-Leu-Ser-His-Lys-Gly-Pro-Nle-Aib-paraBrPhe.

7. The peptidomimetic of claim 1, wherein aa2-aa3-aa4-aa5-aa6-aa7-aa8-aa9-aa10-aa11-aa12-aa13 is Arg-Pro-Arg-azaLeu-Ser-His-Lys-Gly-Pro-Nle-Aib-paraBrPhe.

8. A peptidomimetic of Formula (II):

Z2-Lys-Phe-Arg-Arg-Gln-aa'6-aa'7-aa'8-aa'9-aa'10-aa11-aa'12-aa13-aa14-aa'15-aa'16-aa17, or pharmaceutically acceptable salts thereof, wherein Z2 is H or a long chain moiety;

wherein each of aa'6, aa'7, aa'8, aa'9, aa'10, aa'11, aa'12, aa'13, aa'14, aa'15, aa'16 and aa'17 is independently an amino acid, wherein:

aa'6 comprises Arg or a conservative variant thereof;

aa'7 comprises Pro or a conservative variant thereof;

aa'8 comprises an amino acid or a conservative variant thereof selected from the group consisting of Arg, Arg-D, αMeArg and azaArg;

aa'9 comprises an amino acid or a conservative variant thereof selected from the group consisting of Leu, NMeLeu, αMeLeu and azaLeu;

aa'10 comprises Ser or a conservative variant thereof;

aa'11 comprises His or a conservative variant thereof;

aa'12 comprises Lys or a conservative variant thereof;

aa'13 comprises Gly or a conservative variant thereof;

aa'14 comprises Pro or a conservative variant thereof;

aa'15 is comprises Nle or a conservative variant thereof, wherein Nle is norleucine;

aa'16 is comprises Aib or a conservative variant thereof, wherein Aib is α-aminoisobutryic acid; and aa'17 is comprises paraBrPhe or a conservative variant thereof.

9. The peptidomimetic of claim 8, wherein Z2 is selected from the consisting of H, PALM or PEG; wherein PALM is

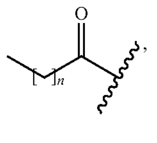

wherein n is from 8 to 20; and

PEG is

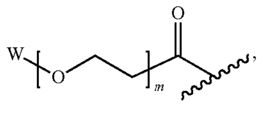

m is from 3 to 10, and W is H, a lower alkyl, or a protecting group.

10. The peptidomimetic of claim 8, wherein Z2 is H.

11. The peptidomimetic of claim 8, wherein Z2 is PALM.

12. The peptidomimetic of claim 9, wherein Z2 is PEG, and W is Fmoc-$NHCH_2CH_2$—.

13. The peptidomimetic of claim 8, wherein aa'6-aa'7-aa'8-aa'9-aa'10-aa'11-aa'12-aa'13-aa'14-aa'15-aa'16-aa'17 is Arg-Pro-Arg-D-Leu-Ser-His-Lys-Gly-Pro-Nle-Aib-paraBr-Phe.

14. The peptidomimetic of claim 8, wherein aa'6-aa'7-aa'8-aa'9-aa'10-aa'11-aa'12-aa'13-aa'14-aa'15-aa'16-aa'17 is Arg-Pro-Arg-NMeLeu-Ser-His-Lys-Gly-Pro-Nle-Aib-paraBrPhe.

15. The peptidomimetic of claim 8, wherein aa'6-aa'7-aa'8-aa'9-aa'10-aa'11-aa'12-aa'13-aa'14-aa'15-aa'16-aa'17 is Arg-Pro-αMeArg-Leu-Ser-His-Lys-Gly-Pro-Nle-Aib-paraBrPhe.

16. The peptidomimetic of claim 8, wherein aa'6-aa'7-aa'8-aa'9-aa'10-aa'11-aa'12-aa'13-aa'14-aa'15-aa'16-aa'17 is Arg-Pro-Arg-αMeLeu-Ser-His-Lys-Gly-Pro-Nle-Aib-paraBrPhe.

17. The peptidomimetic of claim 8, wherein aa'6-aa'7-aa'8-aa'9-aa'10-aa'11-aa'12-aa'13-aa'14-aa'15-aa'16-aa'17 is Arg-Pro-azaArg-Leu-Ser-His-Lys-Gly-Pro-Nle-Aib-paraBrPhe.

18. The peptidomimetic of claim 8, wherein aa'6-aa'7-aa'8-aa'9-aa'10-aa'11-aa'12-aa'13-aa'14-aa'15-aa'16-aa'17 is Arg-Pro-Arg-azaLeu-Ser-His-Lys-Gly-Pro-Nle-Aib-paraBrPhe.

19. A peptidomimetic having the following structure:

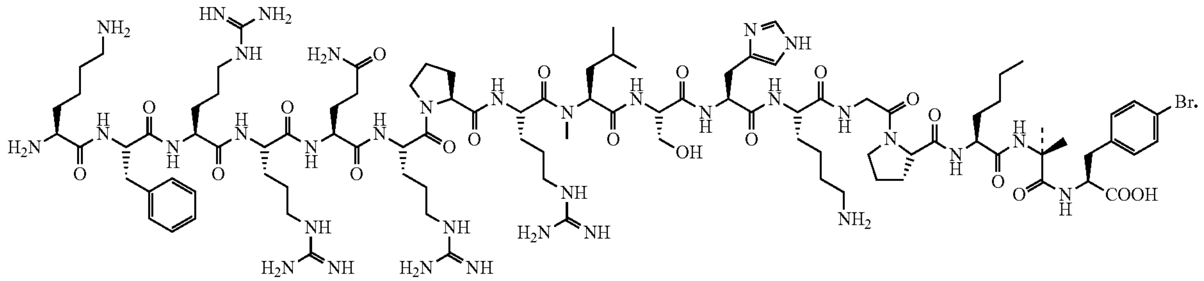

20. A peptidomimetic having the following structure:

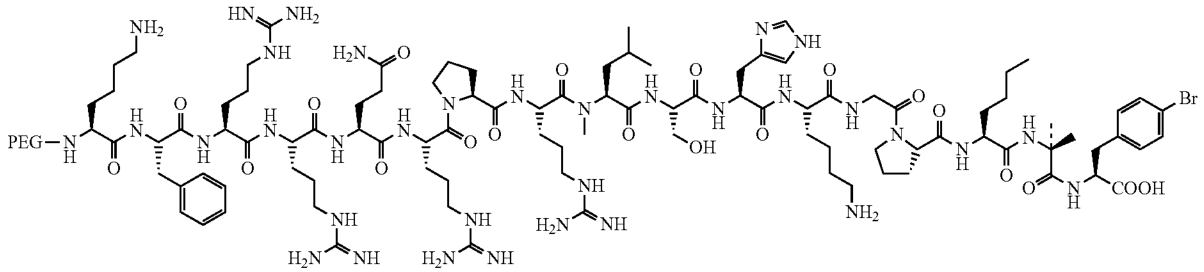

wherein PEG is

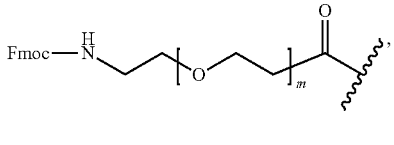

wherein m is from 3 to 10.

21. The peptidomimetic of claim 20, wherein PEG is

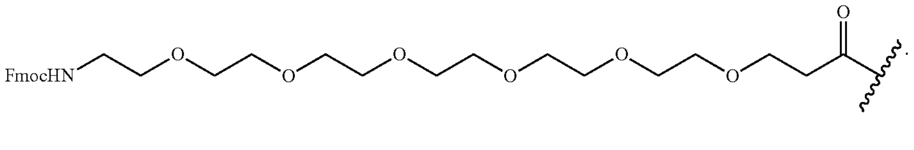

22. The peptidomimetic of claim 8 having the following structure:

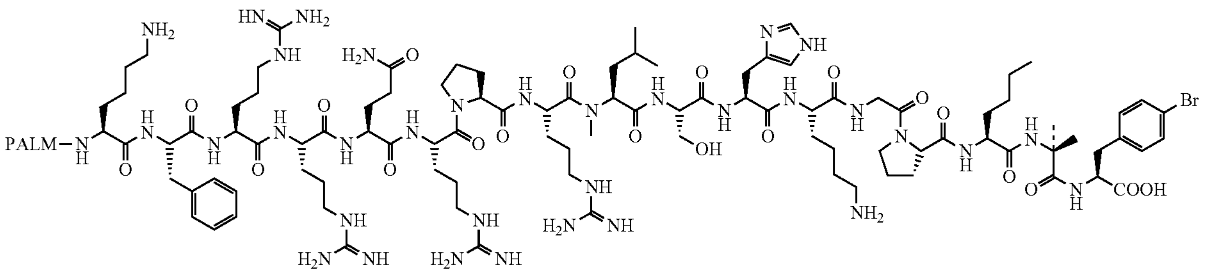

wherein PALM is

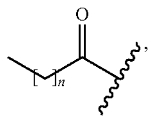

wherein n is from 8 to 20.

23. The peptidomimetic of claim 22, wherein PALM is

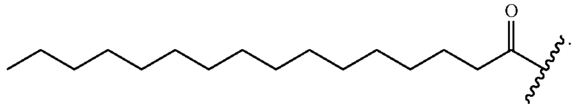 [SMILES: *C(=O)CCCCCCCCCCCCCCC]

24. A peptidomimetic comprising an amino acid sequence which is at least about 80% identical to an amino acid sequence in any of:

Arg-Pro-Arg-D-Leu-Ser-His-Lys-Gly-Pro-Nle-Aib-paraBrPhe;

Arg-Pro-Arg-NMeLeu-Ser-His-Lys-Gly-Pro-Nle-Aib-paraBrPhe;

Arg-Pro-αMeArg-Leu-Ser-His-Lys-Gly-Pro-Nle-Aib-paraBrPhe;

Arg-Pro-Arg-αMeLeu-Ser-His-Lys-Gly-Pro-Nle-Aib-paraBrPhe;

Arg-Pro-azaArg-Leu-Ser-His-Lys-Gly-Pro-Nle-Aib-paraBrPhe;

and

Arg-Pro-Arg-azaLeu-Ser-His-Lys-Gly-Pro-Nle-Aib-paraBrPhe.

25. A composition comprising the peptidomimetic of Formula (II): Z2-Lys-Phe-Arg-Arg-Gln-aa'6-aa'7-aa'8-aa'9-aa'10-aa'11-aa'12-aa'13-aa'14-aa'15-aa'16-aa'17, or pharmaceutically acceptable salts thereof;

wherein Z2 is H or a long chain moiety;

wherein each of aa'6, aa'7, aa'8, aa'9, aa'10, aa'11, aa'12, aa'13, aa'14, aa'15, aa'16 and aa'17 is independently an amino acid, wherein:

aa'6 comprises Arg or a conservative variant thereof;

aa'7 comprises Pro or a conservative variant thereof;

aa'8 comprises an amino acid or a conservative variant thereof selected from the group consisting of Arg, Arg-D, αMeArg and azaArg;

aa'9 comprises an amino acid or a conservative variant thereof selected from the group consisting of Leu, NMeLeu, αMeLeu and azaLeu;

aa'10 comprises Ser or a conservative variant thereof;

aa'11 comprises His or a conservative variant thereof;

aa'12 comprises Lys or a conservative variant thereof;

aa'13 comprises Gly or a conservative variant thereof;

aa'14 comprises Pro or a conservative variant thereof;

aa'15 is comprises Nle or a conservative variant thereof, wherein Nle is norleucine;

aa'16 is comprises Aib or a conservative variant thereof, wherein Aib is α-aminoisobutryic acid; and aa'17 is comprises paraBrPhe or a conservative variant thereof.

26. The composition of claim 25, wherein the composition is a pharmaceutical composition.

27. A method of modulating an apelin pathway disorder in a subject comprising administering to the subject a therapeutically effective amount of an apelin peptide comprising a peptidomimetic of Formula (I) of claim 1 or Formula (II) of claim 8, or pharmaceutically acceptable salts thereof.

28. The method of claim 27, wherein the apelin peptide is an apelin receptor agonist.

29. The method of claim 27, wherein the apelin pathway disorder is a cardiac disease.

30. The method of claim 27, wherein the cardiac disease is selected from the group consisting of systemic arterial hypertension, abdominal aortic aneurysm, pulmonary arterial hypertension, heart failure, myocardial ischemic-reperfusion injury, cardiac allograft vasculopathy, myocardial infarction, and high blood pressure.

31. The method of claim 30, wherein the cardiac disease is abdominal aortic aneurysm.

32. The method of claim 30, wherein the cardiac disease is cardiac allograft vasculopathy.

33. The method of claim 27, wherein the administering is carried out intravenously.

34. A method of modulating vascular tone in a subject comprising administering to the subject an effective amount of an apelin receptor agonist comprising a peptidomimetic of Formula (I) or Formula (II), or pharmaceutically acceptable salts thereof.

35. The method of claim 34, wherein the administering is carried out intravenously.

36. A method of reducing cardiac reperfusion injury following myocardial infarction in a subject comprising administering to the subject an effective amount of an apelin receptor agonist comprising an apelin peptide comprising a peptidomimetic of Formula (I) or Formula (II), or pharmaceutically acceptable salts thereof.

37. The method of claim 36, wherein the cardiac reperfusion injury is due to an ischemic condition.

38. The method of claim 36, wherein the ischemic condition is selected from the group consisting of acute coronary syndromes, thomboembolic events, surgery or resuscitation from cardiac arrest, and combinations thereof.

39. The method of claim 36, wherein the administering step is carried out intravenously.

40. A method of reducing blood pressure in a subject comprising administering to the subject an effective amount of an apelin receptor agonist comprising an apelin peptide comprising a peptidomimetic of Formula (I) or Formula (II), or pharmaceutically acceptable salts thereof.

41. The method of claim 40, wherein the administering step is carried out intravenously.

* * * * *